(12) United States Patent
Tikoo et al.

(10) Patent No.: US 6,849,446 B2
(45) Date of Patent: Feb. 1, 2005

(54) MODIFIED BOVINE ADENOVIRUS HAVING ALTERED TROPISM

(75) Inventors: Suresh K. Tikoo, Saskatoon (CA);
Lorne A. Babiuk, Saskatoon (CA);
Linong Zhang, North York (CA);
Qiaohua Wu, Denver, CO (US)

(73) Assignee: University of Saskatchewan, Saskatoon (CA)

( * ) Notice: Subject to any disclaimer, the term of this patent is extended or adjusted under 35 U.S.C. 154(b) by 0 days.

(21) Appl. No.: 09/871,212

(22) Filed: May 31, 2001

(65) Prior Publication Data

US 2002/0034519 A1 Mar. 21, 2002

Related U.S. Application Data

(60) Provisional application No. 60/208,678, filed on May 31, 2000.

(51) Int. Cl.[7] .............................................. C12N 15/00
(52) U.S. Cl. ................ 435/320.1; 424/93.2; 424/199.1; 424/233.1; 435/69.1; 435/173.3; 435/235.1; 536/23.72; 935/32; 935/57; 935/65
(58) Field of Search .............................. 424/93.2, 199.1, 424/233.1; 435/69.1, 173.3, 235.1, 320.1; 536/23.72; 935/32, 57, 65

(56) References Cited

U.S. PATENT DOCUMENTS

| | | | |
|---|---|---|---|
| 4,510,245 A | 4/1985 | Cousens et al. | 435/172.3 |
| 4,920,209 A | 4/1990 | Davis et al. | 435/235 |
| 5,151,267 A | 9/1992 | Babiuk et al. | 424/87 |
| 5,559,099 A | 9/1996 | Wickham et al. | 514/44 |
| 5,820,868 A | 10/1998 | Mittal et al. | 424/199.1 |
| 5,877,011 A | 3/1999 | Armentano et al. | 435/320.1 |
| 5,922,576 A | 7/1999 | He et al. | 435/91.41 |
| 6,001,591 A | 12/1999 | Mittal et al. | 435/69.1 |
| 6,210,946 B1 | 4/2001 | Curiel et al. | 435/235.1 |

FOREIGN PATENT DOCUMENTS

| | | |
|---|---|---|
| EP | 259149 A2 A3 B1 | 9/1987 |
| EP | 389286 A2 A3 B1 | 3/1990 |
| FR | 2642767 | 1/1989 |
| WO | WO 91/11525 | 8/1991 |
| WO | WO 95/16048 | 6/1995 |
| WO | WO 97/06826 A1 | 2/1997 |
| WO | WO 97/20575 | 6/1997 |
| WO | WO 98/40509 | 9/1998 |
| WO | WO 99/36545 * | 7/1999 |
| WO | WO 99/39734 | 8/1999 |
| WO | WO 99/41359 | 8/1999 |
| WO | WO 00/03029 A2 | 1/2000 |
| WO | WO 00/26395 A2 | 5/2000 |
| WO | WO 00/31285 | 6/2000 |
| WO | WO 00/70071 | 11/2000 |
| WO | WO 01/02431 | 1/2001 |
| WO | WO 01/21216 A1 | 3/2001 |

OTHER PUBLICATIONS

Berkner et al., (1983) "Genention of adenovirus by transfection of plasmids." *Nucleic Acid Research* 11(17):6003–6020.

(List continued on next page.)

*Primary Examiner*—Ulrike Winkler
(74) *Attorney, Agent, or Firm*—Morrison & Foerster LLP

(57) ABSTRACT

The present invention provides modified bovine adenoviruses comprising a modification in a capsid protein wherein said protein is associated with adenovirus tropism and wherein said modification is associated with altered tropism. The present invention provides adenovirus vectors and host cells comprising such vectors. The present invention also provides methods of making and using such adenoviruses.

64 Claims, 41 Drawing Sheets

OTHER PUBLICATIONS

Braun et al. (1988) "Immunogenic duplex nucleic acids are nuclease resistant." *J. Immunol.* 141:2084–2089.

Brennan et al., (1990) "Embryonic transcriptional activation of a Xenopus cytoskeletal actin gene does not require a serum response element." *Roux's Arch. Dev. Biol.* 199:89–96.

Chartier et al., (1996) "Efficient Generation of Recombinant Adenovinis Vectors by Homologous Recombination in Escherichia coli." *J. Virol.* 70(7):4805–4810.

Chaturvedi et al. (1996) "Stabilization of triple–stranded oligonucleotide complexes: use of probes containing alternating phosphodiester and stereo–uniform cationic phosphoramidate linkages." *Nucleic Acids Res.* 24:2318–2323.

Chow et al. (1977) "An Amazing Sequence Amngement at the 5' Ends of Adenovirus 2 Messenger RNA." *Cell* 12:I–8.

Darbyshire et al., (1965) "A new adenovirus serotype of bovine origin." *J. Comp. Pathol.* 75:327–330.

Darbyshire et al., (1966) "The Pathogenesis and Pathology of Infection in Calves with a Strain of Bovine Adenovirus Type 3." *Res. Vet. Sci* 7:81–93.

Darbyshire, (1966) "Oncogenicity of Bovine Adenovirus Type 3 in Hamsters." *Nature* 211:102.

Davison et al., (1993) "The DNA Sequence of Adenovirus Type 40." *J. Mol. Biol.* 234:1308–1316.

Derbyshire et al., (1975) "Serological and Pathogenicity Studies with same unclassified porcine adenoviruses." *J. Camp. Pathol.* 85:437–443.

Derbyshire, (1992) "Chapter 11. Adenovirus." in *Diseases of Swine*, Leman et al., ed., Seventh Edition, Iowa State Univer. Press, Ames, IA. pp. 225–227.

Foy H. M., (1989) "Chapter 3: Adenoviruses" in *Viral Infections of Humans Epidemiology and Control*, Third Edition, Evans A. S., ed., Plenum Medical Book Co., New York, pp. 77–94.

Gaydos and Gaydos, "Chapter 23: Adenovirus Vaccines" in *Vaccines*, Third Edition, Plotkin and Orenstein, eds., W. B. Saunders Company Philadelphia, pp. 609–628.

Graham et al., (1973) "A New Technique for the Assay of Infectivity of Human Adenovirus 5 DNA." *Virology* 52:456–467.

Graham (1984) "Covalently closed circles of human adenovirus DNA are infectious." *EMBO J* 3(12):2917–2922.

Hirahara et al., (1990) "Isolation of Porcine Adenovirus from the Respiratory Tract of Pigs in Japan." *Jpn. J. Vet. Sci.* 52:407–409.

Hu et al., (1984) "Sequence Homology Between Bovine and Human Adenoviruses." *J. Virol.* 49:604–608.

Idamakanti (1998) "Molecular characterization of E3 region of bovine adenovirus–3," M.Sc. thesis, University of Saskatchewan, Saskatoon, Saskatchewan.

Kleiboeker, (1994) "Sequence analysis of putative E3, pVIII, and fiber genornic regions of a porcine adenovirus." *Virus Res.* 31:17–25.

Kleiboeker, (1995) "Identification and sequence analysis of the E1 genomic region of a porcine adenovirus." *Virus Res.* 36:259–268.

Kleiboeker, (1995) "Sequence analysis of the fiber genomic region of a porcine adenovirus predicts a novel fiber protein." *Virus Res.* 39:299.309.

Krasnykh et al. (1996) "Generation of Recombinant Adenovirus Vectors with Modified Fibers for Altering Viral Tropism" *Journal of Virology*, 70(10):6839–6846.

Kunkel et al., (1981) "Rapid and Efficient Site–Specific Mutagenesis without Phenotypic Selection." *Meth. Enzymology* 154:367–382.

Kurokawa et al., (1978) "Biochemical Studies on Bovine Adenovirus Type 3 III. Cleavage Maps of Viral DNA by Restriction Endoncleases EcoRI, BamHl and HindIII." *J. Virol.* 28:212–218.

Latimer et al. (1995) "Specificity of monoclonal antibodies produced against phosphorothioate and ribo modified DNAs." *Molec. immunol* 32(14/15): 1057–1064.

Lee et al. (1998) "Genetic Organization and DNA Sequence of Early Region 4 of Bovine Adenovirus Type 3" *Virus Genes* 17(1):99–100.

Mattson et al., (1988) "Bovine adenovirus type–3 infection in feedlot calves." *Am. J. Vet Res* 49(1):67–69.

McCoy et al. (1996) "Genomic location and nucleotide sequence of a porcine adenovirus penton base gene." *Arch. Virol.* 141:1367–1375.

McCoy et al., (1996) "Nucleotide and amino acid sequence analysis of the porcine adenovinis 23K protein." *DNA Sequence* 6:251–254.

Mittal et al. (1992) "Sequence analysis of bovine adenovirus type 3 early region 3 and fibre protein genes." *J. Gen. Virol.* 73:3295–3300.

Mittal et al. (1993) "Corrigendum: Sequence analysis of bovine adenovirus type 3 early region 3 and fibre protein genes." *J. Gen. Virol.* 74(12):2825.

Morrison et al., (1997) "Complete DNA sequence of canine adenovinis type 1." *J. Gen. Virol.* 78:873–878.

Motoi et al., (1972) "Neoplastic transformation of hamster cells in vitro by bovine adenovirus type–3." *Gann* 63:415–418.

Niiyama et al. (1975) "Biochemical Studies on Bovine Adenovirus Type 3. I. Purification and Properties." *J. Virol.* 16(3):621–633.

Peyrottes et al. (1996) "Oligodeoxynucleoside phosphoramidates ($P-NH_2$): synthesis and thermal stability of duplexes with DNA and RNA targets." *Nucleic Acids Res.* 24(10):1841–1848.

Ausubel et al., (1987) Current Protocols in Molecualr Biology, supplement 30, section 7.7.18, Table 7.7.1.

Bartha, (1969) "Proposal for Subgrouping of Bovine Adenoviruses." *Acta Vet. Acad. Sci. Hung*, 19:319–321.

Bett et al. (1993) "Packaging Capacity and Stability of Human Adenovirus Type 5 Vectors." *J. Virology* 67:5911–5921.

Bett et al., (1994) "An efficient and flexible system for construction of adenovirus vectors with insertions or deletions in early regions 1 and 3." *Proc. Natl. Acad. Sci USA* 91:8802–8806.

Akalu, A. et al. (1999). "The Subgenus–Specific C–Terminal Region of Protein IX Is Located on the Surface of the Adenovirus Capsid," *Journal of Virology* 73(7):6182–6187.

Colby, W.W. and Shenk, T. (1981). "Adenovims Type 5 Virions Can Be Assembled In Vivo in the Absence of Detectable Polypeptide IX," *Journal of Virology* 39(3):977–980.

Fields, B.N. et al. eds. (1996). "Adenoviridae: The Viruses and Their Replication" Chapter 67 *In Fields Virology* Third Edition. Lippincott–Raven vol. 2, pp. 2115–2116.

Ghosh–Choudhury, G. et al. (1987). "Protein IX, A Minor Component of the Human Adenovirus Capsid, Is Essential for the Packaging of Full Length Genomes," *The EMBO Journal* 6(6):1733–1739.

Horwitz, M.S. (1991). "Adenoviridae and Their Replication: Structure of the Virus" Chapter 31 In *Fundamental Virology* Second Edition, Fields, B.N. et al. eds. Raven Press: New York, NY. pp 771–775.

Mathais, P. et al. (1994). "Multiple Adenovirus Serotypes Use αv Integrins for Infection," *Journal of Virology* 68(10):6811–6814.

Reddy, P.S. et al. (1999). "Characterization of Early Region 1 and pIX of Bovine Adenovirus–3," *Virology* 253:299–308.

Vigne, E. et al. (1999). "RGD Inclusion in the Hexon Monomer Provides Adenovirus Type 5–Based Vectors with a Fiber Knob–Independent Pathway for Infection," *Journal of Virology* 73(6):5156–5161.

Reddy et al., (1993) "Restriction Endonuclease Analysis and Molecular Cloning of Porcine Adenovirus Type 3" *Intervirology* 36:161–168.

Reddy et al., (1995) "Comparison of the Inverted Terminal Repetition Sequences from Five Porcine Adenovirus Serotypes." *Virology* 212:237–239.

Reddy et al., (1995) "Sequence analysis of putative pVIII, E3 and fibre regions of porcine adenovirus type 3." *Virus Res.* 36:97–106.

Reddy et al., (1995) "Molecular cloning and physical mapping of porcine adenovirus types I and 2." *Arch. Virol.* 140:195–200.

Reddy et al., (1996) "Porcine adenoviruses types 1, 2 and 3 have short and simple early E–3 regions." *Virus Res.* 43:99–109.

Reddy et al., (1997) "Characterization of the Early Region 4 of Porcine Adenovitus Type 3." *Virus Genes* 15:87–90.

Reddy et al., (1998) "Nucleotide Sequence, Genome Organization, and Transcription Map of Bovine Adenovirus Type 3" *J. Virol.*, 72:1394–1402.

Reddy at al., (1998) "Nucleotide Sequences and Transcription map of Porcine Adenovirus Type 3." *Virology* 251:414–426.

Reddy et al., (1999) "Replication–Defective Bovine Adenovirus Type 3 as an Expression Vector" *J. Virol.*, 73:9137–9144.

Rubin B.A., (1993) "Clinical picture and epidemiology of adenovirus infections." *Acta Microbiol. Hung* 40(4):303–323.

Schultz and Gryaznov, (1996) "Oligo–2'–fluoro–2'–deoxynucleotide N3'→P5' phosphoramidates: sythesis and properties." *Nucleic Acids Res.* 24(15):2966–2973.

Shayakhmetov et al., (2000) "Efficient Gene Transfer into Human CD34+ Cells by a Retargeted Adenovirus Vector" *J Virol*, 74:2567–2583.

Shenk and Horwitz, (1996). "Chapter 67. Adenoviridae: The Viruses and Their Replication and. Chaper 68. Adenoviruses" in *Fields Virology*, Third Edition, vol. 2; Fields, B.N. et al., eds; Lippincotz–Raven Publishers, pp. 2111–2171.

Sprengel et al., (1994) "Nucleotide Sequence of Human Adenovirus Type 12 DNA: Comparative Functional Analysis." *J. Virol.* 68(1):379–389.

Takiff et al., (1981) "Propagation and in vitro studies of previously non–cultivable enteral adenoviruses in 293 cells." *Lancet* 11:832–834.

Tsukamoto and Sugino, (1972) "Nonproductive Infection and Induction of Cellular Deoxyribonucleic Acid Synthesis by Bovine Adenovirus Type 3 in a Contact–Inhibited Mouse Cell Line." *J. Virol.* 9(3):465–473.

Tuboly et al., (1993) "Potential viral vectors for the stimulation of mucosal antibody responses against enteric viral antigens in pigs." *Res. In Vet. Sci.* 54:345–350.

Vrati et al. (1995) "Sequence of Ovine Adenovirus Homologs for 100k Hexon Assembly, 33k, pVIII, and Fiber Genes: Early Region E3 Is Not in the Expected Location." *Virology* 209:400–408.

Xu and Both, (1998) "Altered Tropism of an Ovine Adenovirus Carrying the Fiber Protein Cell Binding Domain of Human Adenovirus Type 5" *Virology* 248:156–163.

Zabner et al., (1999) "A Chimeric Type 2 Adenovirus Vector with a Type 17 Fiber Enhances Gene Transfer to Human Airway Epithelia" *J Virol.* 72:8689–8695.

Zakhartchouk et al., (1998) "Construction and Characterization of E3–Deleted Bovine Adenovirus Type 3 Expressing Full–Length and Truncated Form of Bovine Herpesvirus Type 1 Glycoprotein gD[1]." *Virology* 250:220–229.

Zheng et al., (1994) "The E1 sequence of bovine adenovirus type 3 and complementation of human adenovirus type 5 E1A function in bovine cells." *Virus Research* 31:163–186.

Zoller and Smith, (1982) "Oligonucleotide–directed mutagenesis using M13–derived vectors: an efficient and general procedure for the production of point mutations in any fragment of DNA." *Nucleic Acids Res.* 10(20):6487–6500.

* cited by examiner

FIGURE 1A

```
CATCATCAAT AATCTACAGT ACACTGATGG CAGCGGTCCA ACTGCCAATC ATTTTTGCCA      60
CGTCATTTAT GACGCAACGA CGGCGAGCGT GGCGTGCTGA CGTAACTGTG GGGCGGAGCG     120
CGTCGCGGAG GCGGCGGCGC TGGGCGGGGC TGAGGGCGGC GGGGGCGGCG CGCGGGGCGG     180
CGCGCGGGGC GGGGCGAGGG GCGGAGTTCC GCACCCGCTA CGTCATTTTC AGACATTTTT     240
TAGCAAATTT GCGCCTTTTG CAAGCATTTT TCTCACATTT CAGGTATTTA GAGGGCGGAT     300
TTTTGGTGTT CGTACTTCCG TGTCACATAG TTCACTGTCA ATCTTCATTA CGGCTTAGAC     360
AAATTTTCGG CGTCTTTTCC GGGTTTATGT CCCCGGTCAC CTTTATGACT GTGTGAAACA     420
CACCTGCCCA TTGTTTACCC TTGGTCAGTT TTTTCGTCTC CTAGGGTGGG AACATCAAGA     480
ACAAATTTGC CGAGTAATTG TGCACCTTTT TCCGCGTTAG GACTGCGTTT CACACGTAGA     540
CAGACTTTTT CTCATTTTCT CACACTCCGT CGTCCGCTTC AGAGCTCTGC GTCTTCGCTG     600
CCACCATGAA GTACCTGGTC CTCGTTCTCA ACGACGGCAT GAGTCGAATT GAAAAAGCTC     660
TCCTGTGCAG CGATGGTGAG GTGGATTTAG AGTGTCATGA GGTACTTCCC CCTTCTCCCG     720
CGCCTGTCCC CGCTTCTGTG TCACCCGTGA GGAGTCCTCC TCCTCTGTCT CCGGTGTTTC     780
CTCCGTCTCC GCCAGCCCCG CTTGTGAATC CAGAGGCGAG TTCGCTGCTG CAGCAGTATC     840
GGAGAGAGCT GTTAGAGAGG AGCCTGCTCC GAACGGCCGA AGGTCAGCAG CGTGCAGTGT     900
GTCCATGTGA GCGGTTGCCC GTGGAAGAGG ATGAGTGTCT GAATGCCGTA AATTTGCTGT     960
TTCCTGATCC CTGGCTAAAT GCAGCTGAAA ATGGGGGTGA TATTTTTAAG TCTCCGGCTA    1020
TGTCTCCAGA ACCGTGGATA GATTTGTCTA GCTACGATAG CGATGTAGAA GAGGTGACTA    1080
GTCACTTTTT TCTGGATTGC CCTGAAGACC CCAGTCGGGA GTGTTCATCT TGTGGGTTTC    1140
ATCAGGCTCA AAGCGGAATT CCAGGCATTA TGTGCAGTTT GTGCTACATG CGCCAAACCT    1200
ACCATTGCAT CTATAGTAAG TACATTCTGT AAAAGAACAT CTTGGTGATT TCTAGGTATT    1260
GTTTAGGGAT TAACTGGGTG GAGTGATCTT AATCCGGCAT AACCAAATAC ATGTTTTCAC    1320
AGGTCCAGTT TCTGAAGAGG AAATGTGAGT CATGTTGACT TTGGCGCGCA AGAGGAAATG    1380
TGAGTCATGT TGACTTTGGC GCGCCCTACG GTGACTTTAA AGCAATTTGA GGATCACTTT    1440
TTTGTTAGTC GCTATAAAGT AGTCACGGAG TCTTCATGGA TCACTTAAGC GTTCTTTTGG    1500
ATTTGAAGCT GCTTCGCTCT ATCGTAGCGG GGGCTTCAAA TCGCACTGGA GTGTGGAAGA    1560
GGCGGCTGTG GCTGGGACGC CTGACTCAAC TGGTCCATGA TACCTGCGTA GAGAACGAGA    1620
GCATATTTCT CAATTCTCTG CCAGGGAATG AAGCTTTTTT AAGGTTGCTT CGGAGCGGCT    1680
ATTTTGAAGT GTTTGACGTG TTTGTGGTGC CTGAGCTGCA TCTGGACACT CCGGGTCGAG    1740
TGGTCGCCGC TCTTGCTCTG CTGGTGTTCA TCCTCAACGA TTTAGACGCT AATTCTGCTT    1800
CTTCAGGCTT TGATTCAGGT TTTCTCGTGG ACCGTCTCTG CGTGCCGCTA TGGCTGAAGG    1860
```

FIGURE 1B

```
CCAGGGCGTT CAAGATCACC CAGAGCTCCA GGAGCACTTC GCAGCCTTCC TCGTCGCCCG    1920
ACAAGACGAC CCAGACTACC AGCCAGTAGA CGGGGACAGC CCACCCCGGG CTAGCCTGGA    1980
GGAGGCTGAA CAGAGCAGCA CTCGTTTCGA GCACATCAGT TACCGAGACG TGGTGGATGA    2040
CTTCAATAGA TGCCATGATG TTTTTTATGA GAGGTACAGT TTTGAGGACA TAAAGAGCTA    2100
CGAGGCTTTG CCTGAGGACA ATTTGGAGCA GCTCATAGCT ATGCATGCTA AAATCAAGCT    2160
GCTGCCCGGT CGGAGTATG AGTTGACTCA ACCTTTGAAC ATAACATCTT GCGCCTATGT     2220
GCTCGGAAAT GGGGCTACTA TTAGGGTAAC AGGGGAAGCC TCCCCGGCTA TTAGAGTGGG    2280
GGCCATGGCC GTGGGTCCGT GTGTAACAGG AATGACTGGG GTGACTTTTG TGAATTGTAG    2340
GTTTGAGAGA GAGTCAACAA TTAGGGGGTC CCTGATACGA GCTTCAACTC ACGTGCTGTT    2400
TCATGGCTGT TATTTTATGG GAATTATGGG CACTTGTATT GAGGTGGGGG CGGGAGCTTA    2460
CATTCGGGGT TGTGAGTTTG TGGGCTGTTA CCGGGGAATC TGTTCTACTT CTAACAGAGA    2520
TATTAAGGTG AGGCAGTGCA ACTTTGACAA ATGCTTACTG GGTATTACTT GTAAGGGGA     2580
CTATCGTCTT TCGGGAAATG TGTGTTCTGA GACTTTCTGC TTTGCTCATT TAGAGGGAGA    2640
GGGTTTGGTT AAAAACAACA CAGTCAAGTC CCCTAGTCGC TGGACCAGCG AGTCTGGCTT    2700
TTCCATGATA ACTTGTGCAG ACGGCAGGGT TACGCCTTTG GGTTCCCTCC ACATTGTGGG    2760
CAACCGTTGT AGGCGTTGGC CAACCATGCA GGGGAATGTG TTTATCATGT CTAAACTGTA    2820
TCTGGGCAAC AGAATAGGGA CTGTAGCCCT GCCCCAGTGT GCTTTCTACA AGTCCAGCAT    2880
TTGTTTGGAG GAGAGGGCGA CAAACAAGCT GGTCTTGGCT TGTGCTTTTG AGAATAATGT    2940
ACTGGTGTAC AAAGTGCTGA GACGGGAGAG TCCCTCAACC GTGAAAATGT GTGTTTGTGG    3000
GACTTCTCAT TATGCAAAGC CTTTGACACT GGCAATTATT TCTTCAGATA TTCGGGCTAA    3060
TGGATACATG TACACTGTGG ACTCAACAGA GTTCACTTCT GACGAGGATT AAAAGTGGGC    3120
GGGGCCAAGA GGGGTATAAA TAGGTGGGGA GGTTGAGGGG AGCCGTAGTT TCTGTTTTTC    3180
CCAGACTGGG GGGGACAACA TGGCCGAGGA AGGGCGCATT TATGTGCCTT ATGTAACTGC    3240
CCGCCTGCCC AAGTGGTCGG GTTCGGTGCA GGATAAGACG GGCTCGAACA TGTTGGGGGG    3300
TGTGGTACTC CCTCCTAATT CACAGGCGCA CCGGACGGAG ACCGTGGGCA CTGAGGCCAC    3360
CAGAGACAAC CTGCACGCCG AGGGAGCGCG TCGTCCTGAG GATCAGACGC CCTACATGAT    3420
CTTGGTGGAG GACTCTCTGG GAGGTTTGAA GAGGCGAATG GACTTGCTGG AAGAATCTAA    3480
TCAGCAGCTG CTGGCAACTC TCAACCGTCT CCGTACAGGA CTCGCTGCCT ATGTGCAGGC    3540
TAACCTTGTG GGCGGCCAAG TTAACCCCTT TGTTTAAATA AAAATACACT CATACAGTTT    3600
ATTATGCTGT CAATAAAATT CTTTATTTTT CCTGTGATAA TACCGTGTCC AGCGTGCTCT    3660
```

FIGURE 1C

```
GTCAATAAGG GTCCTATGCA TCCTGAGAAG GGCCTCATAT ACCATGGCAT GAATATTAAG    3720
ATACATGGGC ATAAGGCCCT CAGAAGGGTT GAGGTAGAGC CACTGCAGAC TTTCGTGGGG    3780
AGGTAAGGTG TTGTAAATAA TCCAGTCATA CTGACTGTGC TGGGCGTGGA AGGAAAAGAT    3840
GTCTTTTAGA AGAAGGGTGA TTGGCAAAGG GAGGCTCTTA GTGTAGGTAT TGATAAATCT    3900
GTTCAGTTGG GAGGGATGCA TTCGGGGGCT AATAAGGTGG AGTTTAGCCT GAATCTTAAG    3960
GTTGGCAATG TTGCCCCCTA GGTCTTTGCG AGGATTCATG TTGTGCAGTA CCACAAAAAC    4020
AGAGTAGCCT GTGCATTTGG GGAATTTATC ATGAAGCTTG GAGGGGAAGG CATGAAAAAA    4080
TTTTGAGATG GCTTTATGGC GCCCCAGGTC TTCCATGCAT TCGTCCATAA TAATAGCAAT    4140
AGGCCCGGTT TTGGCTGCCT GGGCAAACAC GTTCTGAGGG TGGGCGACAT CATAGTTGTA    4200
GTCCATGGTC AGGTCTTCAT AGGACATGAT CTTAAAGGCA GGTTTTAGGG TGCTGCTTTG    4260
AGGAACCAGA GTTCCTGTGG GGCCGGGGGT GTAGTTCCCT TCACAGATTT GGGTCTCCCA    4320
AGCAAGCAGT TCTTGCGGGG GTATCATGTC AACTTGGGGG ACTATAAAAA AAACAGTTTC    4380
GGGAGGTGGT TGAATGAGGC CCGTAGACAT AAGGTTTCTG AGGAGCTGGG ATTTTCCACA    4440
ACCGGTTGGT CCGTAGACCA CCCCAATAAC GGGTTGCATG GTAAAGTTTA AAGATTTGCA    4500
TGAACCGTCA GGGCGCAGAT ATGGCATGGT GGCATTCATG GCATCTCTTA TCGCCTGATT    4560
ATAGTCTGAG AGGGCATTGA GTAGGGTGGC GCCCCCCATA GCCAGTAGCT CGTCCAAGGA    4620
AGAAAAGTGT CTAAGAGGTT TGAGGCCTTC AGCCATGGGC ATGGACTCTA AGCACTGTTG    4680
CATGAGAGCA CATTTGTCCC AAAGCTCAGA GACGTGGTCT AGTACATCTC CATCCAGCAT    4740
AGCTCTTTGT TTCTTGGGTT GGGGTGGCTG TTGCTGTAGG GGGCGAGACG GTGACGGTCG    4800
ATGGCCCGCA GGGTGCGGTC TTTCCAGGGC CTGAGCGTCC TCGCCAGGGT CGTCTCGGTG    4860
ACCGTGAAGG GCTGCTGATG CGTCTGTCTG CTGACCAGCG AGCGCCTCAG GCTGAGCCTG    4920
CTGGTGCCGA ACTTTTCGTC GCCTAGCTGT TCAGTGGAAT AATAACAAGT CACCAGAAGG    4980
TCGTAGGAGA GTTGTGAGGT GGCATGGCCT TTGCTCGAAG TTTGCCAGAA CTCTCGGCGG    5040
CGGCAGCTTG GGCAGTAGAT GTTTTTAAGG GCATATAGTT TGGGGGCTAA GAAGACAGAT    5100
TCCTGGCTGT GGGCGTCTCC GTGGCAGCGG GGGCACTGGG TCTCGCATTC CACAAGCCAA    5160
GTCAGCTGAG GGTTGGTGGG ATCAAAGACC AGAGGACGGT TATTACCTTT CAGGCGGTGC    5220
TTGCCTCGGG TGTCCATGAG TTCCTTTCCC CTTTGGGTGA GAAACATGCT GTCCGTGTCT    5280
CCGTAGACAA ATTTGAGAAT CCGGTCTTCT AGGGGAGTGC CTCTGTCTTC TAAATAGAGG    5340
ATGTCTGCCC ATTCAGAGAC AAAGGCTCTA GTCCACGCGA GGACAAATGA AGCTATGTGT    5400
GAGGGTATC TGTTATTAAA TATGAGAGAG GATTTTTTTT GCAAAGTATG CAGGCACAGG    5460
GCTGAGTCAT CAGCTTCCAG AAAGGTGATT GGTTTGTAAG TGTATGTCAC GTGATGGTTC    5520
```

FIGURE 1D

```
TGGGGGTCTC CCAGGGTATA AAAGGGGGCG TCTTCGTCTG AGGAGCTATT GCTAGTGGGT    5580
GTGCACTGAC GGTGCTTCCG CGTGGCATCC GTTTGCTGCT TGACGGGTGA GTAGGTGATT    5640
TTTAGCTCTG CCATGACAGA GGAGCTCAGG TTGTCAGTTT CGACGAAGGC GGTGCTTTTG    5700
ATGTCGTAGG TGCCGTCTGA AATGCCTCTA ACATATTTGT CTTCCATTTG GTCAGAAAAG    5760
ACAGTGACTC TGTTGTCTAG CTTAGTGGCA AAGCTGCCAT ACAGGGCATT GGACAGCAGT    5820
TTGGCAATGC TTCTGAGAGT TTGGTTTTTC TCTTTATCCG CCCTTTCCTT GGGCGCAATG    5880
TTAAGTTGCA CGTAGTCTCT AGCCAGACAC TCCCACTGGG GAAATACTGT GGTGCGGGGG    5940
TCGTTGAGAA TTTGGACTCT CCAGCCGCGG TTATGAAGCG TGATGGCATC CAAACAAGTT    6000
ACCACTTCCC CCCGTAGTGT CTCGTTGGTC CAGCAGAGGC GACCTCCTTT TCTGGAGCAG    6060
AAGGGCGGTA TAACGTCCAA GAATGCTTCT GGGGTGGGT CTGCATCAAT GGTGAATATC     6120
GCGGGCAGTA GGGTGCGATC AAAATAGTCA ATGGGTCTGT GCAACTGGGT TAGGCGGTCT    6180
TGCCAGTTTT TAATTGCAAG CGCTCGATCA AAGGGGTTCA AAGGTTTTCC CGCTGGGAAA    6240
GGATGGGTGA GGGCGCTGGC ATACATGCCG CAGATGTCAT ACACATAGAT GGCTTCTGTT    6300
AGGACGCCTA TGTAGGTAGG ATAGCATCGG CCGCCCCGAA TACTTTCTCT AACGTAATCA    6360
TACATTTCAT TGGAAGGGGC TAGTAGAAAG TTGCCCAGAG AGCTCCTGTT GGGACGCTGG    6420
GATCGGTAGA CTACCTGTCT GAAGATGGCA TGGGAATTGG AGCTGATGGT GGGCCTTTGG    6480
AGGACATTGA AATTGCAGTG GGGCAGCCCC ACTGACGTGT GAACAAAGTC CAAATAAGAT    6540
GCTTGGAGTT TTTTAACCAA TTCGGCCGTA ACCAGCACGT CCATAGCACA GTAGTCCAAG    6600
GTGCGTTGCA CAATATCATA GGCACCTGAA TTCTCTTGCA GCCAGAGACT CTTATTGAGA    6660
AGGTACTCCT CGTCGCTGGA CCAGTAGTCC CTCTGAGGAA AAGAATCTGC GTCGGTTCGG    6720
TAGGTACCTA ACATGTAAAA TTCATTTACA GCTTTGTAAG GGCAGCAGCC TTTTTCCACG    6780
GGTAAAGCGT AAGCGGCAGC TGCGTTCCTG AGACTCGTGT GCGTGAGAGC AAAGGTATCT    6840
CGGACCATGA ACTTCACAAA CTGAAATTTA TAGTCTGCTG AGGTGGGAGT GCCTTCCTCC    6900
CAGTCTTTGA AGTCTTTTCG AGCAGCATGT GTGGGGTTAG GCAGAGCAAA AGTTAAGTCA    6960
TTGAAAAGAA TCTTGCCACA ACGAGGCATG AAATTTCTAC TGACTTTAAA AGCAGCTGGA    7020
ATACCTTGTT TGTTGTTAAT GACTTGTGCG GCTAGAACAA TCTCATCAAA GCCGTTTATG    7080
TTGTGCCCTA CGACATAGAC TTCCAAGAAA GTCGGTTGCC CTTTGAGTTC AAGCGTACAC    7140
AGTTCCTCGA AAGGAATGTC GCTGGCATGG ACATAGCCCA GTTTGAGGCA GAGGTTTTCT    7200
AAGCACGGAT TATCTGCCAG GAACTGGCGC CAAAGCAAAG TGCTGGCAGC TTCTTGAAGG    7260
GCATCCCGAT ACTGTTTAAA CAAGCTGCCT ACTTTGTTTC TTTGCGGGTT GAGGTAGTAG    7320
```

FIGURE 1E

```
AAGGTATTTG CTTGCTTTGG CCAGCTTGAC CACTTTTGCT TTTTAGCTAT GTTAACAGCC    7380
TGTTCGCATA GCTGCGCGTC ACCAAACAAA GTAAACACGA GCATAAAAGG CATGAGTTGC    7440
TTGCCAAAGC TACCGTGCCA AGTGTATGTT TCCACATCAT AGACGACAAA GAGGCGCCGG    7500
GTGTCGGCGT GAGCGGCCCA GGGGAAAAAC TTTATTTCTT CCCACCAGTC CGAAGATTGG    7560
GTGTTTATGT GGTGAAAGTA AAAGTCCCGG CGGCGAGTGC TGCAGGTGTG CGTCTGCTTA    7620
AAATACGAAC CGCAGTCGGC ACATCGCTGG ACCTCTGCGA TGGTGTCTAT GAGATAGAGC    7680
TTTCTCTTGT GAATAAGAAA GTTGAGGGGG AAGGGAAGGC GCGGCCTGTC AGCGCGGGCC    7740
GGGATGCTTG TAATTTTCAG CTTCCCCTTG TATGTTTTGT AAACGCACAT ATTTGCGTTG    7800
CAGAACCGGA CGAGCGTGTC TTGGAATGAA AGGATATTTT CTGGTTTTAA ATCAAATGGG    7860
CAGTGCTCCA AGTGCAGTTC AAAAAGGTTT CGGAGACTGC TGGAAACGTC TGCGTGATAC    7920
TTGACTTCCA GGGTGGTCCC GTCTTCAGTC TGACCGTGCA GCCGTAGGGT ACTGCGTTTG    7980
GCGACCAGGG GCCCCCTTGG GGCTTTCTTT AAAGGGGACG TCGAGGGCCG AGGGCGGCC    8040
TTTGCCTTTC GGGCCTGAGG GGCGGTAGCT GGACCGGATC GTTGAGTTCG GCATGGGTT    8100
GCAGCTGTTG GCGCAGGTCT GATGCGTGCT GCACGACTCT GCGGTTGATT CTCTGAATCT    8160
CCGGGTGTTG GGTGAATGCT ACTGGCCCCG TCACTTTGAA CCTGAAAGAG AGGTCGACAG    8220
AGTTAATAGA TGCATCGTTA AGCTCCGCCT GTCTAATAAT TTCTTCCACG TCACCGCTGT    8280
GGTCTCGGTA AGCAATGTCT GTCATAAACC GTTCGATCTC TTCCTCGTCC AGTTCTCCGC    8340
GACCAGCTCG GTGGACCGTG GCTGCCAAGT CCGTGCTAAT GCGTCGCATG AGCTGGGAAA    8400
AGGCATTGGT TCCCGGTTCA TTCCACACTC TGCTGTATAT AACAGCGCCA TCTTCGTCTC    8460
GGGCTCGCAT GACCACCTGG CCCAAGTTTA GCTCCACGTG GCGAGCAAAG ACGGGCTGA    8520
GGCGGAGGTG GTGGTGCAGA TAATTGAGAG TGGTGGCTAT GTGCTCCACG ATGAAGAAGT    8580
AGATGACCCA TCTGCGGATG GTCGACTCGT TAATGTTGCC CTCTCGCTCC AGCATGTTTA    8640
TGGCTTCGTA AAAGTCCACA GCGAAGTTAA AAAACTGCTC GTTGCGGGCG GAGACTGTCA    8700
GCTCTTCTTG CAGGAGACGA ATGACTTCGG CTACGGCGGC GCGGACTTCT TCGGCAAAGG    8760
AGCGCGGCGG CACGTCCTCC TCCTCCTCTT CTTCCCCCTC CAGCGGGGGC ATCTCCAGCT    8820
CTACCGGTTC CGGGCTGGGG GACAGGGAAG GCGGTGCGGG CCGAACGACC CGTCGGCGTC    8880
GGGTGGGCAA GGGGAGACTC TCTATGAATC GCTGCACCAT CTCGCCCGG CGTATCCGCA    8940
TCTCCTGGGT AACGGCACGC CCGTGTTCTC GGGGTCGGAG CTCAAAAGCT CCGCCCGCA    9000
GTTCGGTCAG AGGCCGCGCC GCGGGCTGGG GCAGGCTGAG TGCGTCAATA ACATGCGCCA    9060
CCACTCTCTC CGTAGAGGCG GCTGTTTCGA ACCGAAGAGA CTGAGCATCC ACGGGATCGC    9120
TGAAGCGTTG CACAAAAGCT TCTAACCAGT CGCAGTCACA AGGTAGGCTG AGCATAGGTG    9180
```

FIGURE 1F

```
AGGCTCGCTC GGTGTTGTTT CTGTTTGGCG GCGGGTGGCT GAGGAGAAAA TTAAAGTACG   9240
CGCACCGCAG GCGCCGGATG GTTGTCAGTA TGATGAGATC CCTGCGACCC GCTTGTTGGA   9300
TTCTGATGCG GTTTGCAAAG CCCCAGGCTT GGTCTTGGCA TCGCCCAGGT TCATGCACTG   9360
TTCTTGGAGG AATCTCTCTA CGGGCACGTT GCGGCGCTGC GGGGGCAGGG TCAGCCATTT   9420
CGGTGCGTCC AAACCCACGC AATGGTTGGA TGAGAGCCAA GTCCGCTACT ACGCGCTCTG   9480
CTAGGACGGC TTGCTGGATC TGCCGCAGCG TTTCATCAAA GTTTTCCAAG TCAATGAAGC   9540
GGTCGTAGGG GCCCGCGTTT ATGGTGTAGG AGCAGTTTGC CATGGTGGAC CAGTCCACAA   9600
TCTGCTGATC TACCCGCACC GTTTCTCGGT ACACCAGTCG GCTATAGGCT CGCGTCTCGA   9660
AAACATAGTC GTTGCAAACG CGCACCACGT ATTGGTAGCC GATTAGGAAG TGCGGCGGCG   9720
GGTATAAGTA GAGCGGCCAG TTTTGCGTGG CCGGCTGTCT GGCGCCAGA TTCCGTAGCA    9780
TGAGTGTGGG GTATCGGTAC ACGTGACGCG ACATCCAGGA GATGCCCGCG GCCGAAATGG   9840
CGGCCCTGGC GTACTCCCGG GCCCGGTTCC ATATATTCCT GAGAGGACGA AAGATTCCAT   9900
GGTGTGCAGG GTCTGCCCCG TAAGACGCGC GCAATCTCTC GCGCTCTGCA AAAACATAC    9960
AGATGAAACA TTTTTGGGGC TTTTCAGATG ATGCATCCCG CTTTACGGCA AATGAAGCCC  10020
AGATCCGCGG CAGTGGCGGG GGTTCCTGCT GCGGCCGCCG GCGCGAGCGT TGACTCAGGC  10080
GGTACTACCG CGCCCCCTGG TGTCGAGTGC GGCGAGGGGG AAGGGTTAGC TCGGCTGTAC  10140
GCGCACCCGG ACACACACCC GCGCGTGTGC GTGAAGCGCG ATGCGGCGGA GGCGTACGTT  10200
CCCCGGGAGA ACTTATTCCG CGACCGCAGC GGGGAGGAAC CCGAAGGGAG CCGAGACCTA  10260
AAGTACAAGG CCGGTCGGCA GTTGCGCGCC GGCATGCCCC GAAAGCGGGT GCTGACCGAA  10320
GGGGACTTTG AGGTGGATGA GCGCACTGGC ATCAGCTCAG CCAAAGCCCA CATGGAGGCG  10380
GCCGATCTAG TGCGGGCTTA CGAGCAAACG GTGAAGCAAG AGGCTAATTT TCAAAAGTCA  10440
TTTAATAACC ACGTGCGGAC ACTGATCTCC CGCGAGGAGA CCACCCTGGG TTTGATGCAC  10500
TTGTGGGACT TTGCGGAGGC ATACGCGCAG AACCCCGGCA GCAAGACCCT TACGGCCCAA  10560
GTCTTTCTCA TCGTGCAGCA CTTGCAAGAT GAGGGCATTT TTGGGGAAGC TTTCTTAAGC  10620
ATAGCAGAGC CCGAGGGACG ATGGATGCTA GATCTGCTAA ACATATTGCA GTCCATTGTG  10680
GTGCAAGAGC GCCAGCTTTC GCTATCTGAA AAGGTAGCCG CGGTGAACTA CTCCGTAGTT  10740
ACCCTGGGCA AACATTATGC CCGCAAGATC TTTAAGAGCC CCTTTGTGCC GCTTGACAAG  10800
GAGGTGAAGA TCAGTACATT TTATATGCGC GCGGTGCTTA AGGTCCTGGG TCTAAGTCAC  10860
GACCTGGGCA TGTACAGAAA CGAAAAGGTG GAGAAGCTAG CTAGCATAGG CAGGCGTTCG  10920
GGAGATGAGC GACGCGGAGC TGCTGTTCAA CCTCCGCCGC GCACTAACCA CTGGCGATTC  10980
```

FIGURE 1G

```
TGAAGCATTC GATGAAGGCG GGGACTTTAC CTGGGCTCCG CCAACTCGCG CGACCGCGGC    11040
GGCCGCTTTG CCGGGGCCCG AGTTTGAGAG TGAAGAGACG GACGATGAAG TCGACGAATG    11100
AGTGATGCGG ACCCCCGTAT CTTTCAGCTG GTCAGTCGGC AAGAGACCGT AGCCATGGCG    11160
GAAGCGCCCC GAAGCCTGGG CCCCGCCCCT TCCAATCCTA GTTTGCAGGC TTTATTCCAA    11220
AGCCAGCCCA GCGCCGAGCA GGAGTGGCAC GGCGTGCTGG AGAGAGTCAT GGCCCTTAAC    11280
AAAAATGGAG ACTTTGGCTC GCAGCCCCAG GCGAACCGGT TTGGAGCCAT CCTCGAAGCC    11340
GTGGTGCCCC CGCGCTCCGA TCCCACCCAT GAAAAAGTGC TAGCTATTGT GAATGCGCTC    11400
TTGGAGACTC AGGCCATCCG TCGCGATGAG GCCGGACAGA TGTACACCGC GCTGTTGCAG    11460
CGGGTGGCCA GATACAACAG TGTGAATGTG CAGGGCAATT TGGACAGGCT GATTCAGGAC    11520
GTGAAGGAGG CTCTGGCGCA GCGCGAGCGC ACCGGGCCGG GGCCGGCCT AGGGTCTGTG    11580
GTAGCCTTGA ATGCCTTCCT GAGCACACAG CCAGCGGTGG TGGAGAGGGG CCAGGAGAAC    11640
TATGTGGCCT TTGTGAGCGC CTTAAAACTC ATGGTGACCG AGGCGCCGCA GTCTGAGGTT    11700
TACCAGGCCG GACCTAGTTT CTTTTTTCAA ACCAGCCGGC ACGGTTCGCA GACGGTAAAC    11760
CTCAGTCAGG CCTTTGATAA CTTGCGACCC CTCTGGGGCG TGCGCGCGCC AGTACACGAG    11820
CGTACTACCA TCTCCTCTCT GCTCACACCA AACACCCGCT TGCTCTTGCT CCTCATTGCG    11880
CCCTTTACGG ACAGCGTGGG CATATCCCGG GACAGTTACC TGGGGCATCT GCTGACCCTT    11940
TACCGGGAGA CCATAGGTAA CACTCGAGTT GATGAGACCA CGTACAACGA GATCACGGAA    12000
GTGAGTCGGG CCCTGGGCGC CGAAGACGCG TCTAACTTGC AAGCCACTCT CAACTACTTA    12060
CTCACAAATA AGCAGAGCAA GTTGCCACAG GAGTTTTCTC TGAGTCCCGA AGAGGAGCGG    12120
GTGCTGCGCT ACGTGCAGCA ATCTGTCAGT TTATTTTTAA TGCAGGATGG ACACACGGCC    12180
ACCACTGCTC TAGATCAGGC TGCGGCCAAC ATAGCGCCCT CGTTTTACGC GTCCACCGC    12240
GACTTTATAA ACCGACTGAT GGACTATTTC CAGCGAGCTG CGGCTATGGC CCCTGACTAC    12300
TTTTTACAGG CTGTTATGAA TCCCCACTGG CTCCCGCCGC CGGGTTTCTT TACTCAGGAG    12360
TTTGACTTTC CGGAGCCCAA CGGAGGCTTC CTGTGGGATG ATTTGGACAG CGCGCTCCTA    12420
CGCGCGCACG TAAAAGAAGA GGAGGATCAA GGAGCTGTGG GCGGCACGCC GGCGGCTTCG    12480
GCGCCCGCGT CTCGCGCGCA CACACCACCG CCGCCGCCCG GTGCCGCGGA CCTCTTTGCT    12540
CCTAACGCCT TCCGCAATGT GCAAAATAAC GGCGTGGATG AACTTATTGA CGGCTTAAGC    12600
AGATGGAAGA CTTACGCCCA GGAGAGGCAG GAAGTCGTTG AGCGGCACAG GCGCAGAGAG    12660
GCGCGTCGCC GGGCGCGCGA GGCGCGTCTA GAGTCGAGCG ATGATGACGA CAGCGACCTA    12720
GGGCCGTTTC TACGGGCAC GGGGCACCTC GTTCACAACC AGTTTATGCA TCTGAAGCCC    12780
CGGGGTCCCC GCCAGTTTTG GTAACCGCAC TGTATTAAGC TGTAAGTCCT CTCATTTGAC    12840
```

FIGURE 1H

```
ACTTACCAAA GCCATGGTCT TGCTTCGCCT CTGACACTTT CTCTCCCCCC ACACGCGGCA    12900
CCCTACAGCC TAGGGGCGAT GCTCCAGCCC GAACTGCAGC CAATTCCGCT GTCCCGCCGC    12960
CGGCTTATGA GGCGGTGGTG GCTGGGGCCT TCCAGACGCT TTCTCTTCGA CGAGATCCAC    13020
GTCCCGCCGC GATATGCTGC CGCGTCTGCG GGGAGAAACA GTATCCGTTA TTCCATGCTG    13080
CCCCCGTTGT ATGACACCAC GAAGATATAC CTTATCGACA ACAAATCTTC AGACATCCAA    13140
ACTCTGAATT ACCAAAACGA CCACTCAGAT TACCTCACTA CCATCGTGCA GAACAGCGAC    13200
TTCACGCCCC TGGAGGCTAG CAACCACAGC ATCGAGCTAG ACGAGCGGTC CCGCTGGGGC    13260
GGAAACCTTA AAACCATCCT TTATACAAAC CTGCCTAATA TCACCCAGCA CATGTTTTCT    13320
AACTCTTTTC GGGTAAAGAT GATGGCCTCA AAAAAAGACG GCGTGCCCCA GTACGAGTGG    13380
TTCCCCCTAA GGCTGCCCGA GGGTAACTTT TCTGAGACTA TGGTCATTGA CCTCATGAAC    13440
AATGCCATCG TAGAGCTGTA CTTGGCTTTG GGGCGCCAGG AGGGCGTGAA GGAAGAGGAC    13500
ATCGGGGTAA AGATCGATAC GCGCAACTTT AGTCTGGGCT ATGACCCGCA GACCCAGTTA    13560
GTGACGCCCG GCGTATACAC CAATGAAGCT ATGCATGCGG ACATCGTGTT GCTGCCGGGC    13620
TGTGCTATAG ACTTTACGCA CTCCCGATTA AACAACCTCT TGGGCATACG CAAGCGTTTT    13680
CCGTACCAAG AGGGCTTCGT CATCTCCTAT GAGGACCTTA AGGGGGGTAA CATCCCCGCT    13740
TTGATGGACG TGGAGGAGTT TAACAAGAGC AAGACGGTTC GAGCTTTGCG GGAGGACCCC    13800
AAGGGGCGCA GTTATCACGT GGGCGAAGAC CCAGAAGCCA GAGAAACGA AACCGCCTAC    13860
CGCAGCTGGT ACCTGGCTTA CAATTACGGG GACCCAGAAA AAGGGGTGCG GGCCACCACA    13920
CTGCTGACTA CCGGCGACGT GACCTGCGGG GTGGAACAGA TCTACTGGAG CTTGCCGGAC    13980
ATGGCACTGG ACCCAGTCAC .TTTCAAGGCT TCGCTGAAAA CTAGCAATTA CCCCGTGGTG    14040
GGCACAGAAC TTTTGCCACT GGTGCCGCGT AGCTTTTATA ACGCTCAGGC TGTGTACTCA    14100
CAGTGGATAC AAGAAAAAAC TAACCAGACC CACGTTTTCA ATCGCTTTCC CGAAAATCAG    14160
ATCTTGGTGC GGCCCCCTGC GCCTACCATC ACGTCCATAA GTGAAAATAA GCCCAGCTTG    14220
ACAGATCACG GAATCGTGCC GCTCCGGAAC CGCTTGGGGG GCGTGCAACG TGTGACTTTG    14280
ACTGACGCGC GGCGAAGATC CTGCCCCTAC GTCTACAAGA GCTTAGGCAT TGTGACGCCG    14340
CAAGTGCTAT CTAGCCGCAC GTTTTAAGCA GACAGGGGCA CAGCAGCCGT TTTTTTTTTT    14400
TTTTTTTCGC TCCACCAGGG ACTGTCAGGA ACATGGCCAT TCTAATCTCT CCTAGCAATA    14460
ACACGGGCTG GGGCCTGGGA TGCAATAAGA TGTACGGGGG CGCTCGCATA CGTTCAGACT    14520
TGCATCCAGT GAAGGTGCGG TCGCATTATC GGGCCGCCTG GGGCAGCCGC ACCGGTCGGG    14580
TGGGTCGCCG CGCAACCGCA GCTTTAGCCG ATGCCGTCGC GGCCACCGGT GATCCGGTGG    14640
```

FIGURE 11

```
CCGACACAAT CGAGGCGGTG GTGGCTGACG CCCGCCAGTA CCGGCGCCGC AGACGGCGAG   14700
GGGTGCGCCG AGTCAGAAGG TTGCGTCGGA GCCCCCGCAC TGCCCTGCAG CGACGGGTTC   14760
GTAGCGTACG CCGACAAGTG GCGAGGGCCC GCAGGGTGGG CCGGCGCGCG GCCGCTATCG   14820
CAGCAGACGC GGCCATGGCC ATGGCGGCGC CAGCTCGGCG ACGCCGTAAC ATCTACTGGG   14880
TACGCGATGC GGCAACCGGA GCCCGCGTTC CGGTGACAAC CCGGCCTACG GTCAGCAACA   14940
CCGTTTGAAA TGTCTGCTAC TTTTTTTTGC TTCAATAAAA GCCCGCCGAC TGATCAGCCA   15000
CACCTTGTCA CGCAGAATTC TTTCAAACCA TTGCGCTCTC AGCGCGCGCG CCGATAAACC   15060
CACTGTGATG GCCTCCTCTC GGTTGATTAA AGAAGAAATG TTAGACATCG TGGCGCCTGA   15120
GATTTACAAG CGCAAACGGC CCAGGCGAGA ACGCGCAGCA CCGTATGCTG TGAAGCAGGA   15180
GGAGAAGCCT TTAGTAAAGG CGGAGCGCAA AATTAAGCGC GGCTCCAGAA AGCGGGCCTT   15240
GTCAGGCGTT GACGTTCCTC TGCCCGATGA CGGCTTTGAG GACGACGAGC CCCACATAGA   15300
ATTTGTGTCT GCGCCGCGTC GGCCCTACCA GTGGAAGGGC AGGCGGGTGC GCCGGGTTTT   15360
GCGTCCCGGC GTGGCCGTTA GTTTCACGCC CGGCGCGCGC TCCCTCCGTC CGAGTTCCAA   15420
GCGGGTGTAT GACGAGGTGT ACGCAGACGA CGACTTCTTA GAAGCGGCCG CGGCCCGTGA   15480
GGGGGAGTTT GCTTACGGAA AGCGGGGACG CGAGGCGGCC CAGGCCCAGC TGCTACCGGC   15540
TGTGGCCGTG CCGGAACCGA CTTACGTAGT TTTGGATGAG AGCAACCCCA CCCCGAGCTA   15600
CAAGCCTGTA ACCGAGCAGA AAGTTATTCT TTCCCGCAAG CGGGGTGTGG GGAAGGTAGA   15660
GCCTACCATC CAGGTTTTAG CTAGCAAGAA GCGGCGCATG GCCGAGAATG AGGATGACCG   15720
CGGGGCCGGC TCCGTGGCCG AAGTGCAGAT GCGAGAAGTT AAACCGGTAA CCGCTGCCTT   15780
GGGTATTCAG ACCGTGGATG TTAGCGTGCC CGACCACAGC ACTCCCATGG AGGTCGTGCA   15840
GAGTCTCAGT CGGGCGGCTC AAGTAGCTCA ACGCCTGACC CAACAACAGG TGCGGCCTTC   15900
GGCTAAGATT AAAGTGGAGG CCATGGATCT TTCTGCTCCC GTAGACGCAA AGCCTCTTGA   15960
CTTAAAACCC GTGGACGTAA AGCCGACCCC GACCTTCGTG CTTCCAGCT  TTCGTTCACT   16020
CAGCACCCAA ACTGACTCTT TGCCCGCGGC AGTGGTCGTG CCGCGCAAGC CCGCGTGCA   16080
CCGTGCTACT AGGCGTACTG CGCGCGGCTT GCTGCCCTAT TACCGCCTGC ATCCTAGCAT   16140
CACGCCGACA CCGGGTTACC GAGGATCTGT CTACACGAGC TCGGGTGTGC GCCTGCCCGC   16200
CGTCCGGGCG CCGCCGTCGC CGCCGTACCC GCAGGGCGAC TCCCGCCTC  AGCGCTGCCG   16260
CGGCCGCGGC GCTGCTGCCC GGCGTGCGCT ATCACCCTAG CATCCGCCAA GCGGCCACAG   16320
TAACCCGGCT CGGCCGTTAA GCGCTGTGAA ACTGCAACAA CAACAACAAA AATAAAAAAA   16380
AGTCTCCGCT CCACTGTGCA CCGTTGTCCA TCGGCTAATA AAGTCCCGCT TTGTGCGCCG   16440
CAGGAACCAC TATCCGTAAC CTGCGAAAAT GAGTCCCCGC GGAAATCTGA CTTACAGACT   16500
```

FIGURE 1J

```
GAGAATACCG GTCGCCCTCA GTGGCCGGCG CCGGCGCCGA ACAGGCTTGC GAGGAGGGTC  16560
TGCGTACCTG CTCGGCCGCC GCAGAAGGCG CGCGGGCGGC GGCCGCCTGC GCGGGGGCTT  16620
CCTTCCCCTC CTGGCTCCCA TCATTGCAGC CGCCATCGGC GCAATCCCCG GCATCGCATC  16680
AGTGGCCATT CAGGCGGCCC ACAACAAATA GGGACAGTGT AAAGAAAGCT CAATCTCAAT  16740
AAAACAAACC GCTCGATGTG CATAACGCTC TCGGCCTGCA ACTTCTGCTG CTTACGTCTT  16800
TGACCAAAGT CACTACTGTT TTCCTTTTAC CCAGAGCCGG CGCCAGCCCC ACACAGCTTG  16860
TTAACACGCC ATGGACGAAT ACAATTACGC GGCTCTTGCT CCCCGGCAAG GCTCCCGACC  16920
CATGCTGAGC CAGTGGTCCG GCATCGGCAC GCACGAAATG CACGGCGGAC GTTTTAATCT  16980
GGGCAGTTTG TGGAGCGGGA TCAGGAATGT GGGCAGCGCG TTAAGAACTG GGGCTCTCGG  17040
GCCTGGCACA GCAATGCGGG CAAGCGTTGC GCGCCCAGCT GAAAAAGACG GCTTGCAAG   17100
AAAAGATATT GAGGGCGTTA GCGCCGGTAT CCACGGAGCC GTGGATCTGG GCCGTCAGCA  17160
GCTAGAGAAA GCTATTGAGC AGCGCCTAGA GCGTCGCCCC ACCGCTGCCG GTGTGGAAGA  17220
CCTTCCGCTT CCCCCGGGAA CAGTCTTAGA AGCTGATCGT TTACCGCCCT CCTACGCCGA  17280
AGCGGTGGCT GAGCGCCCGC CGCCGGCTGA CGTTCTCCTG CCCGCATCCT CAAAGCCGCC  17340
GGTGGCGGTG GTGACCTTGC CCCCGAAAAA GAGAGTGTCT GAAGAGCCTG TGGAGGAAGT  17400
TGTGATTCGT TCCTCCGCAC CGCCGTCGTA CGACGAGGTT ATGGCACCGC AGCCGACTCT  17460
GGTAGCCGAG CAGGGCGCCA TGAAAGCAGT GCCCGTGATT AAGCCGGCTC AACCTTTTAC  17520
CCCAGCTGTG CACGAAACGC AACGCATAGT GACCAACTTG CCAATCACCA CAGCTGTGAC  17580
ACGGCGACGC GGGTGGCAGG GCACTCTGAA TGACATCGTG GGCCTCGGCG TTCGTACCGT  17640
GAAGCGCCGG CGGTGCTATT GAGGGGGCGC GCAGCGGTAA TAAAGAGAAC ATAAAAAAGC  17700
AGGATTGTGT TTTTTGTTTA GCGGCCACTG ACTCTCCCTC TGTGTGACAC GTCCTCCGCC  17760
AGAGCGTGAT TGATTGACCG AGATGGCTAC CCCGTCGATG CTGCCGCAAT GGTCCTACTG  17820
CACATCGCCG GTCAGGACGC GTCCGAGTAC CTGTCCCCCG GCTTGGTGCA ATTCGCACAA  17880
GCCACCGAAT CCTACTTTAA CATTGGGAAC AAGTTTAGAA ACCCCACCGT CGCCCCGACG  17940
CACGATGTCA CCACGGAGCG TTCGCAGCGT CTGCAGCTCC GCTTCGTGCC CGTAGACCGG  18000
GAGGACACAC AGTACTCCTA CAAAACCCGC TTCCAGCTAG CCGTGGGCGA CAACCGGGTG  18060
CTGGACATGG CCAGCACGTA TTTTGACATC CGCGGTACGC TGGAGAGGGG CGCCAGTTTC  18120
AAGCCTTACA GCGGCACGGC CTACAACTCC TTTGCCCCCA ACAGTGCCCC TAACAATACG  18180
CAGTTTAGGC AGGCCAACAA CGGTCATCCT GCTCAGACCA TAGCTCAAGC TTCTTACGTG  18240
GCTACCATCG GCGGTGCCAA CAATGACTTG CAAATGGGTG TGGACGAGCG TCAGCAGCCG  18300
```

FIGURE 1K

```
GTGTATGCGA ACACTACGTA CCAGCCGGAA CCTCAGCTCG GCATTGAAGG TTGGACAGCT    18360
GGATCCATGG CGGTCATCGA TCAAGCAGGC GGGCGGGTTC TCAGGAACCC TACTCAAACT    18420
CCCTGCTACG GGTCCTATGC TAAGCCGACT AACGAGCACG GGGGCATTAC TAAAGCAAAC    18480
ACTCAGGTGG AGAAAAAGTA CTACAGAACA GGGGACAACG GTAACCCGGA AACAGTGTTT    18540
TATACTGAAG AGGCTGACGT GCTAACGCCC GACACCCACC TTGTTCACGC GGTACCGGCC    18600
GCGGATCGGG CAAAGGTGGA GGGGCTATCT CAGCACGCAG CTCCCAACAG GCCGAACTTT    18660
ATCGGCTTTC GGGACTGCTT TGTAGGCTTG ATGTATTATA ACAGCGGGGG CAACCTGGGC    18720
GTCTTAGCGG GTCAATCCTC TCAGCTGAAT GCCGTGGTAG ACCTGCAAGA CCGCAACACT    18780
GAGCTTTCCT ATCAGATGCT TCTTGCAAAC ACGACGGACA GATCCCGCTA TTTTAGCATG    18840
TGGAACCAAG CCATGGACTC GTACGACCCG GAGGTCAGGG TGATAGATAA CGTGGGCGTA    18900
GAGGACGAGA TGCCTAATTA CTGCTTTCCG TTGTCGGGGG TTCAGATTGG AAACCGTAGC    18960
CACGAGGTTC AAAGAAACCA ACAACAGTGG CAAAATGTAG CTAATAGTGA CAACAATTAC    19020
ATAGGCAAGG GGAACCTACC GGCCATGGAG ATAAATCTAG CGGCCAATCT CTGGCGTTCC    19080
TTTTTGTACA GTAATGTGGC GTTGTACTTG CCAGACAACC TTAAATTCAC CCCTCACAAC    19140
ATTCAACTCC CGCCTAACAC GAACACCTAC GAGTACATGA ACGGGCGAAT CCCCGTTAGC    19200
GGCCTTATTG ATACGTACGT AAATATAGGC ACGCGGTGGT CGCCCGATGT GATGGACAAC    19260
GTGAATCCCT TTAACCACCA CCGCAACTCG GGCCTGCGTT ACCGCTCCCA GCTGCTGGGC    19320
AACGGCCGCT TCTGCGACTT TCACATTCAG GTGCCACAAA AGTTTTTTGC TATTCGAAAC    19380
CTGCTTCTCC TGCCCGGCAC GTACACTTAC GAGTGGTCCT TTAGAAAGGA CGTAAACATG    19440
ATCCTTCAGA GCACTCTGGG CAATGATCTG CGGGTCGATG GGGCCACTGT TAATATTACC    19500
AGCGTCAACC TCTACGCCAG CTTCTTTCCC ATGTCACATA ACACCGCTTC CACTTTGGAA    19560
GCTATGCTCC GCAACGACAC TAATGACCAG TCTTTTAATG ACTATCTCTC GGCGGCTAAC    19620
ATGTTGTATC CCATTCCGCC CAATGCCACC CAACTGCCCA TCCCCTCACG CAACTGGGCA    19680
GCGTTCCGTG GCTGGAGTCT CACCCGGCTA AAACAGAGGG AGACACCGGC GCTGGGGTCC    19740
CCGTTCGATC CCTATTTCAC CTATTCGGGC ACCATCCCGT ACCTGGACGG CACTTTTTAC    19800
CTCAGCCACA CCTTTCGCAA GGTGGCCATC CAGTTTGACT CTTCTGTGAC CTGGCCCGGC    19860
AATGACAGGC TTTTAACCCC TAACGAGTTC GAAATAAAAA TAAGTGTGGA CGGTGAAGGC    19920
TACAACGTGG CTCAGAGCAA TATGACTAAG GACTGGTTCC TGGTGCAGAT GCTAGCGAAT    19980
TACAACATAG GCTACCAGGG ATATCACCTG CCCCCGGACT ACAAGGACAG GACATTTTCC    20040
TTCCTGCATA ACTTCATACC CATGTGCCGA CAGGTTCCCA ACCCAGCAAC CGAGGGCTAC    20100
TTTGGACTAG GCATAGTGAA CCATAGAACA ACTCCGGCTT ATTGGTTTCG ATTCTGCCGC    20160
```

FIGURE 1L

```
GCTCCGCGCG AGGGCCACCC CTACCCCCAA CTGGCCTTAC CCCCTCATTG GGACCCACGC   20220
CATGCCCTCC GTGACCCAGA GAGAAAGTTT CTCTGCGACC GCACCCTCTG GCGAATCCCC   20280
TTCTCCTCGA ACTTCATGTC CATGGGGTCC CTCACAGATC TCGGACAGAA CCTACTGTAT   20340
GCCAATGCCG CGCATGCCCT AGACATGACT TTTGAGATGG ATCCCATCAA TGAGCCCACT   20400
CTGCTGTACG TTCTGTTTGA GGTGTTTGAC GTGGCCCGCG TTCACCAGCC CCACAGAGGC   20460
GTGATCGAAG TGGTGTACTT GAGAACGCCA TTCTCAGCCG GCAACGCTAC CACATAAGTG   20520
CCGGCTTCCC TCTCAGGCCC CGCGATGGGT TCTCGGGAAG AGGAGCTGAG ATTCATCCTT   20580
CACGATCTCG GTGTGGGGCC ATACTTCCTC GGCACTTTCG ATAAACACTT TCCGGGGTTC   20640
ATCTCCAAAG ACCGAATGAG CTGTGCCATA GTCAACACTG CCGGACGCGA AACCGGGGGC   20700
GTGCATTGGC TGGCCATGGC TTGGCACCCA GCCTCGCAGA CCTTTTACAT GTTTGACCCT   20760
TTCGGTTTCT CGGATCAAAA GCTAAAGCAA ATTTACAACT TTGAGTATCA GGGCCTCCTA   20820
AAGCGCAGCG CCCTGACTTC CACTGCTGAC CGCTGCCTGA CCCTTATTCA AAGCACTCAA   20880
TCTGTCCAGG GACCCAACAG CGCCGCCTGC GGTCTGTTCT GCTGCATGTT CCTCCACGCC   20940
TTTGTCCGCT GGCCGCTTAG GGCCATGGAC AACAATCCCA CCATGAACCT CATCCACGGA   21000
GTTCCCAACA ACATGTTGGA GAGCCCCAGC TCCCAAAATG TGTTTTTGAG AAACCAGCAA   21060
AATCTGTACC GTTTCCTAAG ACGCCACTCC CCCCATTTTG TTAAGCATGC GGCTCAAATT   21120
GAGGCTGACA CCGCCTTTGA TAAAATGTTA ACAAATTAGA CCGTGAGCCA TGATTGCAGA   21180
AGCATGTCAT TTTTTTTTTA TTGTTTAAAA TAAAAACAAC ACATAACATC TGCCGCCTGT   21240
CCTCCCGTGA TTTCTTCTGC TTTATTTGCA AATGGGGGGC ACCTTAAAAC AAAGAGTCAT   21300
CTGCATCGTA CTGATCGATG GGCAGAATAA CATTCTGATG CTGGTACTGC GGGTCCCAGC   21360
GGAATTCGGG AATGGTAATG GGGGGCTCT GTTTAACCAG CGCGGACCAC ATCTGCTTAA   21420
CCAGCTGCAA GGCTGAAATC ATATCTGGAG CCGAAATCTT GAAATCGCAG TTTCGCTGGG   21480
CATTAGCCCG CGTCTGCCGG TACACAGGGT TACAGCACTG AAATACTAAC ACCGATGGGT   21540
GTTCTACGCT GGCCAGGAGT TTGGGATCTT CTACGAGGCT CTTATCTACC GCAGAGCCCG   21600
CGTTGATATT AAAGGGCGTT ATCTTGCATA CCTGACGGCC TAGGAGGGGC AATTGGGAGT   21660
GACCCCAGTT ACAATCACAC TTTAAAGGCA TAAGCAGATG AGTTCCGGCA CTTTGCATCC   21720
TGGGGTAACA GGCTTTCTGA AAGGTCATGA TCTGCCAGAA AGCCTGCAAA GCCTTGGGCC   21780
CCTCGCTGAA AAACATACCA CAAGACTTTG AGGTAAAGCT GCCGGCCGGC AAAGCGGCGT   21840
CAAAGTGACA GCAAGCCGCG TCTTCATTCT TTAGCTGCAC TACGTTCATA TTCCACCGGT   21900
TGGTGGTGAT CTTTGTCTTA TGCGGGGTCT CTTTTAAAGC CCGCTGCCCA TTTTCGCTGT   21960
```

FIGURE 1M

```
TCACATCCAT CTCTATCACT TGGTCTTTGG TAAGCATAGG CAGGCCATGC AGGCAGTGAA   22020
GGGCCCCGTC TCCCCCCTCG GTACACTGGT GGCGCCAGAC CACACAGCCC GTGGGGCTCC   22080
ACGAGGTCGT CCCCAGGCCT GCGACTTTTA ACACAAAATC ATACAAGAAG CGGCCCATAA   22140
TAGTTAGCAC GGTTTTCTGA GTACTGAAAG TAAGAGGCAG GTACACTTTA GACTCATTAA   22200
GCCAAGCTTG TGCAACCTTC CTAAAACACT CGAGCGTGCC AGTGTCGGGC AGCAAGGTTA   22260
AGTTTTTAAT ATCCACTTTC AAAGGCACAC ACAGCCCCAC TGCTAATTCC ATGGCCCGCT   22320
GCCAAGCAAC TTCGTCGGCT TCCAGCAAGG CCCGGCTGGC CGCCGGCAGG GCGGGAGCGG   22380
CGGCCTCAGC GGCTGGGGCT GAAGGTTTGA AAATCTTGGC GCGCTTAACG GCTGTGACAT   22440
CTTCGGCGGG GGGCTCAGCG ATCGGCGCGC GCCGTTTGCG GCTGACTTTT TTCCGGGGCG   22500
TCTCATCTAT CACTAAGGGG TTCTCGTCCC CGCTGCTGTC AGCCGAACTC GTGGCTCGCG   22560
TTAAGTCACC GCTGCGATTC ATTATTCTCT CCTAGATAAC GACAACAAAT GGCAGAGAAA   22620
GGCAGTGAAA ATCAGCGGCC AGAGAACGAC ACTGAGCTAG CAGCGGTTTC AGAAGCCCTA   22680
GGCGCGGCCG CTTCGGCCCC CTCACGTAAC TCCCGACTG ACACGGATTC AGGGGTGGAA   22740
ATGACGCCCA CCAGCAGCCC CGAGCCGCCC GCCGCTCCCC CAAGTTCGCC TGCCGCAGCA   22800
CCTGCCCCTC AGAAGAACCA GGAGGAGCTC TCTTCCCCCG AGCCCGCGGT AGCAGCAGCG   22860
GAGCCAGAAG CCGCTTCGCG GCCCAGACCA CCCACACCCA CCGTTCAGGT CCCGCGGGAG   22920
CCGAGCGAGG ATCAACCTGA CGGACCCGCG ACGAGGCCTT CGTACGTGAG CGAGGATTGC   22980
CTCATCGGCC ATATCTCTCG CCAGGCTAAC ATTGTTAGAG ACAGCCTGGC AGACCGCTGG   23040
GAGTTAGAGC CCACCGTGTC GGCTCTCTCC GAGGCTTACG AAAAGCTCCT CTTTTGTCCC   23100
AAGGTACCAC CCAAGAAGCA AGAGAATGGC ACTTGCGAAC CTGAACCTCG CGTTAATTTT   23160
TTCCCCACCT TTGTAGTGCC CGAAACTTTA GCCACGTAGC ACATCTTTTT CCAAAACCAA   23220
AAAATCCCCC TGTCTTGTCG CGCCAACCGC ACCCACACAG ACACCATCAT GCACCTCTAC   23280
TGGGGGACT CCTTACCGTG CTTCCCCACG CTGCAGCTGG TCAACAAAAT CTTTGAAGGC   23340
TTGGGCTCAG AGGAGCGGCG CGCAGCCAAC TCGCTGAAAG ATCAAGAGGA TAACAGCGCG   23400
TTAGTTGAGC TCGAAGGGGA CAGTCCCCGA CTGGCTGTGG TTAAGCGCAC ACTGTCTTTG   23460
ACACATTTCG CCTACCCTGC CATAACACTA CCGCCTAAGG TGATGGCAGC TGTCACTGGC   23520
AGCCTCATTC ATGAATCAGC AGCGACCGCC GAACCGGAAG CTGAGGCGCT GCCAGAAGCC   23580
GAGGAGCCCG TGGTTAGTGA CCCTGAACTT GCTCGCTGGT TGGGGCTCAA CTTACAACAG   23640
GAGCCCGAGG CCACGGCCCA GGCTTTGGAA GAAAGACGCA AGATTATGTT GGCAGTATGC   23700
TTAGTCACAC TTCAGCTCGA GTGCCTGCAC AAGTTTTTTT CTTCAGAGGA TGTCATCAAA   23760
AAGCTGGGAG AGAGCCTCCA CTACGCCTTT CGCCACGGCT ACGTGCGCCA AGCCTGCTCC   23820
```

FIGURE 1N

```
ATTTCTAACG TGGAACTAAC GAACATCGTC TCATACCTGG GTATCTTGCA CGAAAACCGC  23880
TTGGGACAGA GTACCCTACA CGCCACCCTT AAAGACGAGA ACCGCAGAGA CTACATCAGA  23940
GACACAGTCT TTCTCTTTCT GGTTTATACT TGGCAGACTG CCATGGGCAT TTGGCAGCAG  24000
TGCCTCGAGA CTGAGAACGT AAAAGAACTT GAAAAGCTCT TGCAAAAAAG CAAGAGGGCT  24060
CTCTGGACGG GCTTCGACGA GCTCACCATA GCTCAAGACC TAGCTGACAT AGTGTTCCCC  24120
CCCAAATTCT TGCACACCTT GCAAGCCGGC CTGCCAGACC TTACATCCCA GAGTCTCCTT  24180
CACAACTTTC GCTCCTTCAT TTTCGAACGC TCGGGCATTC TACCCGCCAT GTGCAATGCA  24240
CTGCCCACCG ACTTCATCCC TATCAGCTAC CGGGAGTGCC CTCCAACTTT CTGGGCCTAC  24300
ACCTACCTCT TTAAACTGGC CAATTACCTC ATGTTTCACT CCGACATCGC TTACGATCGG  24360
AGCGGCCCCG GTCTCATGGA ATGCTACTGT CGCTGCAACC TGTGCAGTCC TCACCGCTGC  24420
TTGGCGACCA ACCCCGCCCT GCTCAGCGAG ACCCAAGTTA TCGGTACCTT CGAGATTCAG  24480
GGCCCTCCTG CTCAAGACGG ACAGCCGACC AAACCGCCCC TCAGGCTGAC TGCAGGTCTC  24540
TGGACTTCCG CCTACCTGCG CAAATTTGTA CCGCAAGACT TCAACGCCCA CAAAATAGCC  24600
TTCTACGAAG ACCAATCCAA AAAGCCGAAA GTGACCCCCA GCGCTTGTGT CATCACTGAA  24660
GAAAAAGTTT TAGCCCAATT GCATGAAATT AAAAAAGCGC GGGAAGACTT TCCTCTTAAA  24720
AAGGGGCACG GAGTGTATCT GGACCCTCAG ACCGGCGAGG AGCTGAACGG ACCCGCACCC  24780
TCCGCAGCTA GGAATGAAAC CCCGCAGCAT GTCGGCAGCC GGGCCTTCCG CGGCTCAGGC  24840
TTCGGAGGGC CAACAGCTGC CGCCACAGAC AGCGGGGCTG CAGCCGAGCA AGAGGGCTGT  24900
GAGGAAGGTA GTAGCTTCTC TGAATCCCAC CGCCGCCCTG GAAGACATAT CCGAGGGGGA  24960
GGAAGGCTTC CCCCTGACGG ACGAGGAAGA CGGGGACACC CTGGAGAGCG ATTTCAGCGA  25020
CTTCACGGAC GAAGACGTCG AGGAGGAGGA TATGATTTCG ATACCCCGCG ACCAGGGGCA  25080
CTCCGGCGAG CTCGAGGAGG GCGAAATTCC CGCAACGGTA GCGGCGACGG CGGTCAAGAA  25140
GGGCCAGGGC AAGAAGAGTA GGTGGGACCA GCAGGTCCGC TCCACAGCGC CTCTAAAGGG  25200
CGCTAGAGGT AAGAGGAGCT ACAGCTCCTG GAAACCCCTC AAGCCCACTA TCCTTTCATG  25260
CTTACTGCAG AGCTCCGGCA GCACTGCCTT CACTCGCCGC TATCTGCTTT TTCGCCATGG  25320
CGTGTCCGTT CCCTCCAGGG TAATTCATTA CTATAATTCT TACTGCAGAC CCGAAGCTGA  25380
CCAAAACCGC CACTCAGAGC AAAAAGAGCC GCCGGAGTGC CAGCGCGGCG CGCCCTCGCC  25440
CTCCTCCTCT TCCTCCCAAG CGTGCTCGGG CGCCCCGCCG CCCCAAAGGC CAGCGCCATC  25500
AGGCCGACGA CGCAAGCACC GAGGGCCGCG ACAAGCTTCG GGAGCTGATC TTTCCCACTC  25560
TCTATGCCAT ATTCCAACAA AGTCGCGCTC AGCGGTGTCA CCTCAAAGTG AAAAATAGAT  25620
```

FIGURE 10

| | | | | | |
|---|---|---|---|---|---|
|CCTTACGTTC|ACTGACGCGC|AGCTGCCTCT|ACCACAACAA|GGAGGAACAG|CTCCAGCGAA 25680|
|CCCTAGCAGA|CTCCGAGGCG|CTTCTCAGTA|AATACTGCTC|TGCAGCTCCG|ACACGATTCT 25740|
|CGCCGCCCTC|TTATACCGAG|TCTCCGCCA|AGGACGAATC|CGGACCCGCC|TAAACTCTCA 25800|
|GCATGAGCAA|AGAAATTCCC|ACACCTTATG|TTTGGACCTT|TCAACCTCAG|ATGGGAGCGG 25860|
|CCGCAGGTGC|CAGTCAAGAT|TACTCGACCC|GCATGAATTG|GTTCAGCGCG|GGACCTGATA 25920|
|TGATCCACGA|CGTTAACAAC|ATTCGTGACG|CCCAAAACCG|CATCCTTATG|ACTCAGTCGG 25980|
|CCATTACCGC|CACTCCCAGG|AATCTGATTG|ATCCCAGACA|GTGGGCCGCC|CACCTCATCA 26040|
|AACAACCCGT|GGTGGGCACC|ACCCACGTGG|AAATGCCTCG|CAACGAAGTC|CTAGAACAAC 26100|
|ATCTGACCTC|ACATGGCGCT|CAAATCGCGG|GCGGAGGCGC|TGCGGGCGAT|TACTTTAAAA 26160|
|GCCCCACTTC|AGCTCGAACC|CTTATCCCGC|TCACCGCCTC|CTGCTTAAGA|CCAGATGGAG 26220|
|TCTTTCAACT|AGGAGGAGGC|TCGCGTTCAT|CTTTCAACCC|CCTGCAAACA|GATTTGCCT 26280|
|TCCACGCCCT|GCCCTCCAGA|CCGCGCCACG|GGGGCATAGG|ATCCAGGCAG|TTTGTAGAGG 26340|
|AATTTGTGCC|CGCCGTCTAC|CTCAACCCCT|ACTCGGGACC|GCCGGACTCT|TATCCGGACC 26400|
|AGTTTATACG|CCACTACAAC|GTGTACAGCA|ACTCTGTGAG|CGGTTATAGC|TGAGATTGTA 26460|
|AGACTCTCCT|ATCTGTCTCT|GTGCTGCTTT|TCCGCTTCAA|GCCCCACAAG|CATGAAGGGG 26520|
|TTTCTGCTCA|TCTTCAGCCT|GCTTGTGCAT|TGTCCCCTAA|TTCATGTTGG|GACCATTAGC 26580|
|TTCTATGCTG|CAAGGCCCGG|GTCTGAGCCT|AACGCGACTT|ATGTTTGTGA|CTATGGAAGC 26640|
|GAGTCAGATT|ACAACCCCAC|CACGGTTCTG|TGGTTGGCTC|GAGAGACCGA|TGGCTCCTGG 26700|
|ATCTCTGTTC|TTTTCCGTCA|CAACGGCTCC|TCAACTGCAG|CCCCCGGGGT|CGTCGCGCAC 26760|
|TTTACTGACC|ACAACAGCAG|CATTGTGGTG|CCCAGTATT|ACCTCCTCAA|CAACTCACTC 26820|
|TCTAAGCTCT|GCTGCTCATA|CCGGCACAAC|GAGCGTTCTC|AGTTTACCTG|CAAACAAGCT 26880|
|GACGTCCCTA|CCTGTCACGA|GCCCGGCAAG|CCGCTCACCC|TCCGCGTCTC|CCCCGCGCTG 26940|
|GGAACTGCCC|ACCAAGCAGT|CACTTGGTTT|TTTCAAAATG|TACCCATAGC|TACTGTTTAC 27000|
|CGACCTTGGG|GCAATGTAAC|TTGGTTTTGT|CCTCCCTTCA|TGTGTACCTT|TAATGTCAGC 27060|
|CTGAACTCCC|TACTTATTTA|CAACTTTTCT|GACAAAACCG|GGGGCAATA|CACAGCTCTC 27120|
|ATGCACTCCG|GACCTGCTTC|CCTCTTTCAG|CTCTTTAAGC|CAACGACTTG|TGTCACCAAG 27180|
|GTGGAGGACC|CGCCGTATGC|CAACGACCCG|GCCTCGCCTG|TGTGGCGCCC|ACTGCTTTTT 27240|
|GCCTTCGTCC|TCTGCACCGG|CTGCGCGGTG|TTGTTAACCG|CCTTCGGTCC|ATCGATTCTA 27300|
|TCCGGTACCC|GAAAGCTTAT|CTCAGCCCGC|TTTTGGAGTC|CCGAGCCCTA|TACCACCCTC 27360|
|CACTAACAGT|CCCCCCATGG|AGCCAGACGG|AGTTCATGCC|GAGCAGCAGT|TTATCCTCAA 27420|
|TCAGATTTCC|TGCGCCAACA|CTGCCCTCCA|GCGTCAAAGG|GAGGAACTAG|CTTCCCTTGT 27480|

FIGURE 1P

```
CATGTTGCAT GCCTGTAAGC GTGGCCTCTT TTGTCCAGTC AAAACTTACA AGCTCAGCCT    27540
CAACGCCTCG GCCAGCGAGC ACAGCCTGCA CTTTGAAAAA AGTCCCTCCC GATTCACCCT    27600
GGTCAACACT CACGCCGGAG CTTCTGTGCG AGTGGCCCTA CACCACCAGG GAGCTTCCGG    27660
CAGCATCCGC TGTTCCTGTT CCCACGCCGA GTGCCTCCCC GTCCTCCTCA AGACCCTCTG    27720
TGCCTTTAAC TTTTTAGATT AGCTGAAAGC AAATATAAAA TGGTGTGCTT ACCGTAATTC    27780
TGTTTTGACT TGTGTGCTTG ATTTCTCCCC CTGCGCCGTA ATCCAGTGCC CCTCTTCAAA    27840
ACTCTCGTAC CCTATGCGAT TCGCATAGGC ATATTTTCTA AAAGCTCTGA AGTCAACATC    27900
ACTCTCAAAC ACTTCTCCGT TGTAGGTTAC TTTCATCTAC AGATAAAGTC ATCCACCGGT    27960
TAACATCATG AAGAGAAGTG TGCCCCAGGA CTTTAATCTT GTGTATCCGT ACAAGGCTAA    28020
GAGGCCCAAC ATCATGCCGC CCTTTTTTGA CCGCAATGGC TTTGTTGAAA ACCAAGAAGC    28080
CACGCTAGCC ATGCTTGTGG AAAAGCCGCT CACGTTCGAC AAGGAAGGTG CGCTGACCCT    28140
GGGCGTCGGA CGCGGCATCC GCATTAACCC CGCGGGGCTT CTGGAGACAA ACGACCTCGC    28200
GTCCGCTGTC TTCCCACCGC TGGCCTCCGA TGAGGCCGGC AACGTCACGC TCAACATGTC    28260
TGACGGGCTA TATACTAAGG ACAACAAGCT AGCTGTCAAA GTAGGTCCCG GGCTGTCCCT    28320
CGACTCCAAT AATGCTCTCC AGGTCCACAC AGGCGACGGG CTCACGGTAA CCGATGACAA    28380
GGTGTCTCTA AATACCCAAG CTCCCCTCTC GACCACCAGC GCGGGCCTCT CCCTACTTCT    28440
GGGTCCCAGC CTCCACTTAG GTGAGGAGGA ACGACTAACA GTAAACACCG GAGCGGGCCT    28500
CCAAATTAGC AATAACGCTC TGGCCGTAAA AGTAGGTTCA GGTATCACCG TAGATGCTCA    28560
AAACCAGCTC GCTGCATCCC TGGGGACGG TCTAGAAAGC AGAGATAATA AAACTGTCGT    28620
TAAGGCTGGG CCGGACTTA CAATAACTAA TCAAGCTCTT ACTGTTGCTA CCGGGAACGG    28680
CCTTCAGGTC AACCCGGAAG GGCAACTGCA GCTAAACATT ACTGCCGGTC AGGGCCTCAA    28740
CTTTGCAAAC AACAGCCTCG CCGTGGAGCT GGGCTCGGGC CTGCATTTTC CCCTGGCCA    28800
AAACCAAGTA AGCCTTTATC CCGGAGATGG AATAGACATC CGAGATAATA GGGTGACTGT    28860
GCCCGCTGGG CCAGGCCTGA GAATGCTCAA CCACCAACTT GCCGTAGCTT CCGGAGACGG    28920
TTTAGAAGTC CACAGCGACA CCCTCCGGTT AAAGCTCTCC CACGGCCTGA CATTTGAAAA    28980
TGGCGCCGTA CGAGCAAAAC TAGGACCAGG ACTTGGCACA GACGACTCTG GTCGGTCCGT    29040
GGTTCGCACA GGTGAGGAC TTAGAGTTGC AAACGGCCAA GTCCAGATCT TCAGCGGAAG    29100
AGGCACCGCC ATCGGCACTG ATAGCAGCCT CACTCTCAAC ATCCGGCGC CCCTACAATT    29160
TTCTGGACCC GCCTTGACTG CTAGTTTGCA AGGCAGTGGT CCGATTACTT ACAACAGCAA    29220
CAATGGCACT TTCGGTCTCT CTATAGGCCC CGGAATGTGG GTAGACCAAA ACAGACTTCA    29280
```

FIGURE 1Q

```
GGTAAACCCA GGCGCTGGTT TAGTCTTCCA AGGAAACAAC CTTGTCCCAA ACCTTGCGGA  29340
TCCGCTGGCT ATTTCCGACA GCAAAATTAG TCTCAGTCTC GGTCCCGGCC TGACCCAAGC  29400
TTCCAACGCC CTGACTTTAA GTTTAGGAAA CGGGCTTGAA TTCTCCAATC AAGCCGTTGE  29460
TATAAAAGCG GGCCGGGGCT TACGCTTTGA GTCTTCCTCA CAAGCTTTAG AGAGCAGCCT  29520
CACAGTCGGA AATGGCTTAA CGCTTACCGA TACTGTGATC CGCCCCAACC TAGGGACGG   29580
CCTAGAGGTC AGAGACAATA AAATCATTGT TAAGCTGGGC GCGAATCTTC GTTTTGAAAA  29640
CGGAGCCGTA ACCGCCGGCA CCGTTAACCC TTCTGCGCCC GAGGCACCAC CAACTCTCAC  29700
TGCAGAACCA CCCCTCCGAG CCTCCAACTC CCATCTTCAA CTGTCCCTAT CGGAGGGCTT  29760
GGTTGTGCAT AACAACGCCC TTGCTCTCCA ACTGGGAGAC GGCATGGAAG TAAATCAGCA  29820
CGGACTTACT TTAAGAGTAG GCTCGGGTTT GCAAATGCGT GACGGCATTT TAACAGTTAC  29880
ACCCAGCGGC ACTCCTATTG AGCCCAGACT GACTGCCCCA CTGACTCAGA CAGAGAATGG  29940
AATCGGGCTC GCTCTCGGCG CCGGCTTGGA ATTAGACGAG AGCGCGCTCC AAGTAAAAGG  30000
TGGGCCCGGC ATGCGCCTGA ACCCTGTAGA AAAGTATGTA ACCCTGCTCC TGGGTCCTGG  30060
CCTTAGTTTT GGGCAGCCGG CCAACAGGAC AAATTATGAT GTGCGCGTTT CTGTGGAGCC  30120
CCCCATGGTT TTCGGACAGC GTGGTCAGCT CACATTTTTA GTGGGTCACG GACTACACAT  30180
TCAAAATTCC AAACTTCAGC TCAATTTGGG ACAAGGCCTC AGAACTGACC CCGTCACCAA  30240
CCAGCTGGAA GTGCCCCTCG GTCAAGGTTT GGAAATTGCA GACGAATCCC AGGTTAGGGT  30300
TAAATTGGGC GATGGCCTGC AGTTTGATTC ACAAGCTCGC ATCACTACCG CTCCTAACAT  30360
GGTCACTGAA ACTCTGTGGA CCGGAACAGG CAGTAATGCT AATGTTACAT GGCGGGCTA   30420
CACTGCCCCC GGCAGCAAAC TCTTTTTGAG TCTCACTCGG TTCAGCACTG GTCTAGTTTT  30480
AGGAAACATG ACTATTGACA GCAATGCATC CTTTGGGCAA TACATTAACG CGGGACACGA  30540
ACAGATCGAA TGCTTTATAT TGTTGGACAA TCAGGGTAAC CTAAAAGAAG GATCTAACTT  30600
GCAAGGCACT TGGGAAGTGA AGAACAACCC CTCTGCTTCC AAAGCTGCTT TTTTGCCTTC  30660
CACCGCCCTA TACCCCATCC TCAACGAAAG CCGAGGGAGT CTTCCTGGAA AAAATCTTGT  30720
GGGCATGCAA GCCATACTGG GAGGCGGGGG CACTTGCACT GTGATAGCCA CCCTCAATGG  30780
CAGACGCAGC AACAACTATC CCGCGGGCCA GTCCATAATT TTCGTGTGGC AAGAATTCAA  30840
CACCATAGCC CGCCAACCTC TGAACCACTC TACACTTACT TTTTCTTACT GGACTTAAAT  30900
AAGTTGGAAA TAAAGAGTTA AACTGAATGT TTAAGTGCAA CAGACTTTTA TTGGTTTTGG  30960
CTCACAACAA ATAACAACAG CATAGACAAG TCATACCGGT CAAACAACAC AGGCTCTCGA  31020
AAACGGGCTA ACCGCTCCAA GAATCTGTCA CGCAGACGAG CAAGTCCTAA ATGTTTTTTC  31080
ACTCTCTTCG GGGCCAAGTT CAGCATGTAT CGGATTTTCT GCTTACACCT TTTAGACAG   31140
```

FIGURE 1R

```
CAGTTTACAC TCATTTCCGT TAAAGGATTA CAACTGCGGC ATATGAGAAT TAAGTATATA   31200
CAACTATTGC CCTTTACCCA CAAACACTCC CCCCACGGGG TGCACCTGAT GTAGCTGCCC   31260
TCCTCAATCA TGAAAGTGCT ATTAAAGTAA ATTAAATGAA CATTATTCAC ATACACGCTT   31320
CCCACATAGG GCAAAAAAAC AGAGGACAAC TTTGACAGCT CCCGCCTGAA ATACCAATAC   31380
ACTCTATCAA ACTGCGCACC GTGCACGCAC TGCTTTACCA GGCCTTGAAA GTAAACAGCG   31440
GCGGACCGAC ACTGCAAGCT TCTAGGCTTT GGGCAGTGGC AGTGAATATA TAGCCACTCC   31500
TCCCCATGCA CGTAGTAGGA ACGCCGCTTC CCGGGAATCA CAAATGACAA GCAGTAGTCA   31560
CAGAGGCAAC TAGTCAAGTG AGCGTCCTCC TGAGGCATGA TTACCTTCCA TGGAATGGGC   31620
CAGTGAATCA TAGTGGCAAA GCCAGCTGCA TCTGGAGCGC TGCGAACCTT GGCTACATGT   31680
GGTGATTGGC GACGCAGATG GAGACAGGAC CTTGCATTCT GAAGACCACT GCAACAGCTT   31740
CTGCGTACGC TTGTATTTAC AGTACATAAA AAAGCACTTT TGCCACAGAG CGGTCTTACT   31800
CAACCGACAG CTTTTTTCTT TCTGACGCTG CCTTCTGCTA CTCAGGTAGT ACAAGTCCAA   31860
AAGAGCCAAA CGGACACTCA AATCCGGGTT ATCTCGATGC TGAAGCCAGA GTCCAAAAGT   31920
AACCACGCTA AAAGCCTGCA TCCATATTTT GTAACTGCTG TAACTCCATC CCAGAGCCGG   31980
GCACCGCACT TGGTCCACCA TAGCTGCAAA CAAACGGGAC AATTAAGGAA AGTAAAATGA   32040
GCGCTGGGGG CGGACTCTTC TCCCGTTCGT AGGAAACAGC CACGTATCAA ACACCCTTTT   32100
CAACACTGGC TCTCCAGCCG CTACTCGTTG AATTAATTTG TCCCTGTGCT CAAACAACCC   32160
ACACTGGTAA CGGTGGTCGC TAGGCAAACA TGTCAAATAG CACATAATCA TTTCCTTCAC   32220
TTTAAGCAAA CATCGACTAG CAGACACTTC ACTTAATTCA GCACAGTCAT AGCAAGGAAT   32280
GATTATACAC TTGTCATCTA ATCCACTGCC CATGTACACA TTGCCCCAGG CAAAAGTGGG   32340
CAGGGACTTT AAGAGCTGAT TGCTCGCCCC GACATAGTTG GTAAAATACA GCAAATGCAC   32400
CTTGTTAACA TACACACTCC CCACATAGTA AATATACCGA GTAGACAGCT TAGAAAGCTC   32460
CCTCCGAAAA AATGGGAACA TGGTATCAAA GGCAGTGCCC GCAACACACA TCTTGAACAG   32520
ATCCATCAGG ATAGTAGCTC GACACAGCCC CTGCAGACTT TGGTCAGCTT GCTTGCTGCA   32580
GCAGTACACT CTCCACGTAG CATCTCCGCT GATGAAGTAT TCGCTATCGC AGCGACCAAA   32640
AATACAGCAA TCACAAGGCA GACGCAACAG TCTTTCATCC AGACTGTTCA TGAGAGGCTT   32700
TAGAGGTATG GGAAAAAATC CAAAGTGCTC AAAATAAGCA GCGCTGGGCT CATTCTGACA   32760
TTCCCCCAAC ATGCTGAGTC GAACCATAGC ACAGTCATAC AAACTCAGCT GTCGGAATTG   32820
ATCTTCCATG ATTGAGTTTC TACTGAGATA TTATCTCAAA CTTAAAACTG TTGCTCACCA   32880
ACTCTATGCG AACTTGCTCA AGAAGCTCTT GGTTTAGGGC GACCTCTTCT GGTCGTCGGA   32940
```

FIGURE 1S

```
AGTTACTGAT GGAACAACAA GCGCCGCCCA ACTTCAAATT TCCAGCCGAC CCAATCCAGT      33000
GGTCTCTCAA CTCACGCGCA CAAGCTACTA TGCAGTCCTC ACTTTCGTCA AAGTCAGCAG      33060
CGCCTATAGA AATCAACACA CTGAGTCCAC CATCTTCAGC TTTTAAGGGA TAACAGCTGA      33120
TAGCAAACTG GTTCTGAGAC CACGGCAAAG CACGTAGGAA TTGCTGTTAA GTTAATTTCC      33180
AAACACCGCT GAAGCAGCTC TATGGTTGCT GGACATATGT CCTCTGCATA GAAGCTTTGA      33240
ACATAACTTA AGACAGGGCC GGGCACATGA AACACAAACA GAGAACTATA CACAATCTGG      33300
GCCATGATCA CTCACATTTA AATAGCAGCT GAAAAGTGGC TTTCTTCACT TGGGAGCAAA      33360
ATTAGCGAAG ACTGTGCCAG AATGCTCACG TCGAAAGGCG GTGGGTCTCG CAGAGGCAGG      33420
TTCGGAGCTC TAATTAAACA CAGGTGGGTA ATCCAGTCAA CGATGAGGAC CAGCTGAAAA      33480
GTGGCTTTCT TCACTTGGGA GCAAAATTAG CGAAGACTGT GCCAGAATGC TCACGTCGAA      33540
AGGCGGTGGG TCTCGCAGAG GCAGGTTCGG AGCTCTAATT AAACACAGGT GGGTAATCCA      33600
GTCAACGATG AGGACTTTTA AAAAACTGTC TAAAACTGAA GCAGTTAAGT TAGAGGCAGA      33660
CACAGAAAAA ACTACAGTTA AACTATCAGT TGCTGAAATT GAAAAGCACC CAATAATTAT      33720
GCGCGAGGGC ACAGGCAATA AAAGTGTTAG CCCCTCGGCT AACGCGTCAG CTAAAAAATC      33780
TTTAGCTAAA GTATCTACTG GCCGCGTGGT AAAAGTTTGA ATATAATTTA CGACAGGAGC      33840
TGGCAAGTGA AACTCCACAA AAAAAGTAAA TGGCTGCACA CACGCCATTA TTTTGAAAAT      33900
AAGAAGTACT CACAAAATCA GCTGGAGCTG CCGCAAGTGA AAAAGACCAG CTGAAGTCTT      33960
ATTTTAAACT GTAAAATATA AAAAAAAAAA TAGGGCGTGA ACAAAAATGA GAAAATAATA      34020
CCGGATATGA CTATTAAGGG CGTACACTGA AACTGGGTAA TATTTGAGAA AAAGATTAAG      34080
ATAATAGCTG AACAAATGTT GTGTGCAGAA CACGGAAGAA TGGTGGCGAA AAAAAAAAAC      34140
AGTGTAAGCA CATGGCGCGC ACGTACTTCC GTGAGAAAAA TTAAAAAAAT TTACCCAGTA      34200
TAAGGTGCGT CATTAGACCC GCCTTGTGGC GCGGTTGTAG CCCTGCCCTT TGCCCCGCCC      34260
CGCGCGCCGC CCCGCGCGCC GCCCCGCCGG CCCTCAGCCC CGCCCAGCGC CGCCGCCTCC      34320
GCGACGCGCT CCGCCCCACA GTTACGTCAG CACGCCACGC TCGCCGTCGT TGCGTCATAA      34380
ATGACGTGGC AAAAATGATT GGCAGTTGGA CCGCTGCCAT CAGTGTACTG TAGATTATTG      34440
ATGATG                                                               34446
```

Analysis of BAV600 by Restriction Enzyme *Bgl* II Digestion
1  2  3                                    1  2  3
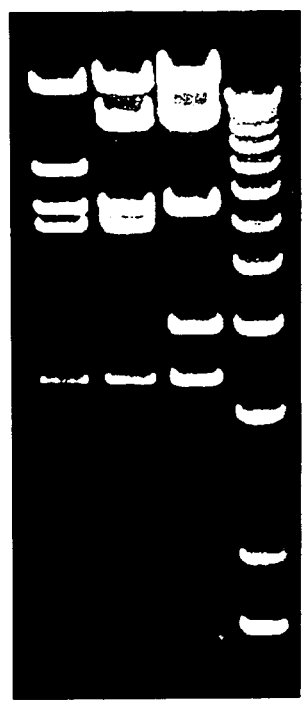                       
Lane 1. BAV302
     2. BAV304
     3. BAV600
Figure 5A                                  Figure 5B

Expression of HAV-5 Fiber Knob by BAV600

Mab against HAV5 knob
1 2 3 4 5

Ab against BAV3 knob
6 7 8 9

Lane 1. Mock
2. HAV-5
3. BAV3
4. BAV304
5. BAV600
6. Mock
7. BAV3
8. BAV304
9. BAV600

Figure 6

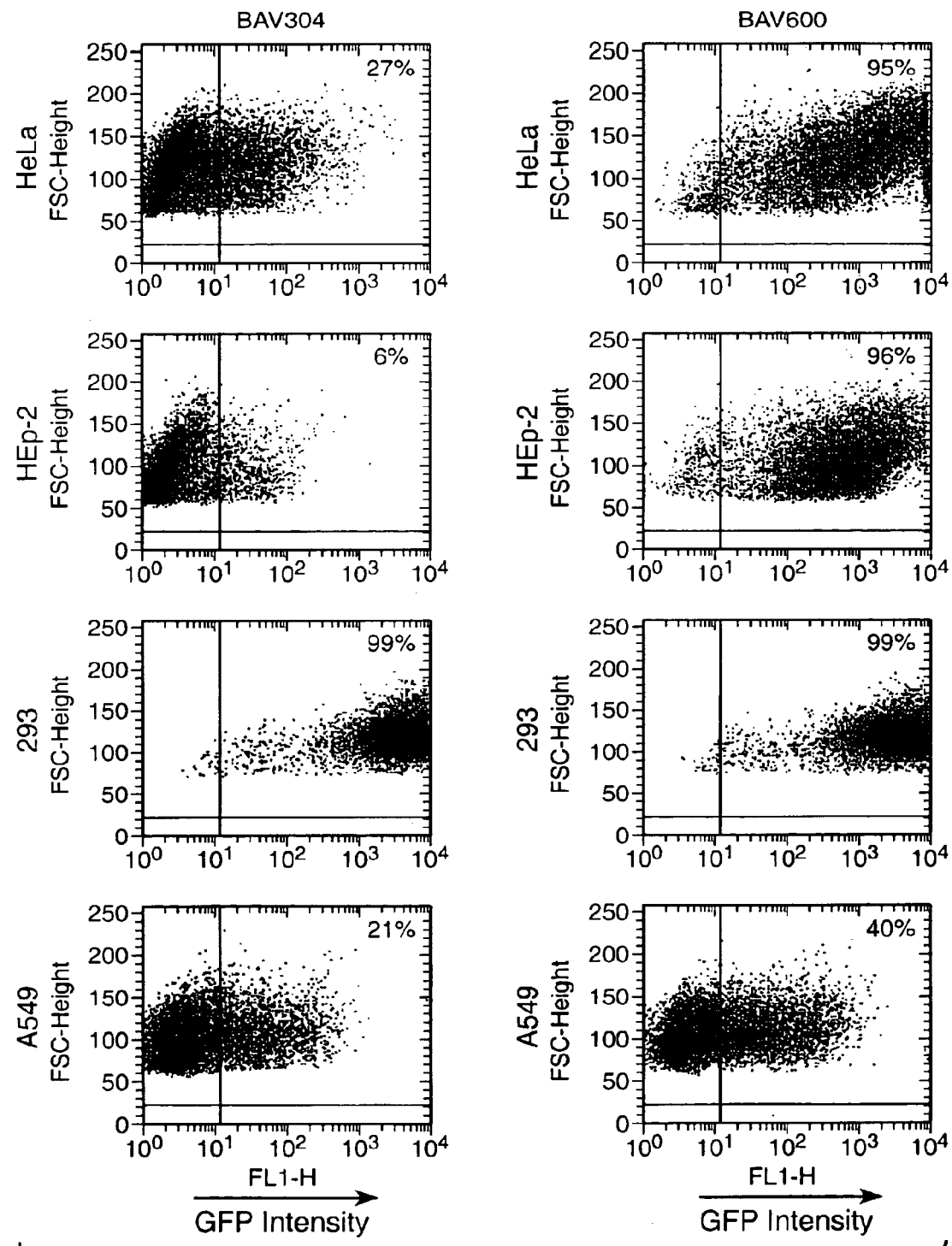
FIG._8

|  | Virus | |
|---|---|---|
|  | BAV-3 | BAV600 |
| Normal Rabbit Serum | <1:50 | <1:50 |
| Rabbit Antiserum against BAV3 FK | 1:800 | <1:50 |
| Monoclonal Ab against BHV gD (2C8) | <1:50 | <1:50 |
| Monoclonal Ab against HAd5 FK (1D6.14) | <1:50 | 1:3,200 |

```
          10        20        30        40
          |         |         |         |
MSVSSCSCPSAPTIFMLLQMKRARPSEDTFNPVYPYDTET    40
GPPTVPFLTPPFVSPNGFQESPPGVLSLRLSEPLVTSNGM    80
LALKMGNGLSLDEAGNLTSQNVTTVSPPLKKTKSNINLEI   120
SAPLTVTSEALTVAAAAPLMVAGNLTMQSQAPLTVHDSK    160
LSIATQGPLTVSEGKLALQTSGPLTTTDSSTLTITASPPL   200

210       220       230       240
          |         |         |         |
TTATGSLGIDLKEPIYTQNGKLGLKYGAPLHVTDDLNTLT   240
VATGPGVTINNTSLQTKVTGALGFDSQGNMQLNVAGGLRI   280
DSQNRRLILDVSYPFDAQNQLNLRLGQGPLFINSAHNLDI   320
NYNKGLYLFTASNNSKKLEVNLSTAKGLMFDATAIAINAG   360
DGLEFGSPNAPNTNPLKTKIGHGLEFDSNKAMVPKLGTGL   400

410       420       430       440
          |         |         |         |
SFDSTGAITVGNKNNDKLTLWTTPAPSPNCRLNAEKDAKL   440
TLVLTKCGSQILATVSVLAVKGSLAPISGTVQSAHLIIRF   480
DENGVLLNNSFLDPEYWNFRNGDLTEGTAYTNAVGFMPNL   520
SAYPKSHGKTAKSNIVSQVYLNGDKTKPVTLTITLNGTQE   560
TGDTTPSAYSMSFSWDWSGHNYINEIFATSSYTFSYIAQE   600
```

FIGURE 13

```
         10        20        30        40
MKRSVPQDFNLVYPYKAKRPNIMPPFFDRNGFVENQEATL  40
AMLVEKPLTFDKEGALTLGVGRGIRINPAGLLETNDLASA  80
VFPPLASDEAGNVTLNMSDGLYTKDNKLAVKVGPGLSLDS 120
NNALQVHTGDGLTVTDDKVSLNTQAPLSTTSAGLSLLLGP 160
SLHLGEEERLTVNTGAGLQISNNALAVKVGSGITVDAQNQ 200
        210       220       230       240
LAASLGDGLESRDNKTVVKAGPGLTITNQALTVATGNGLQ 240
VNPEGQLQLNITAGQGLNFANNSLAVELGSGLHFPPGQNQ 280
VSLYPGDGIDIRDNRVTVPAGPGLRMLNHQLAVASGDGLE 320
VHSDTLRLKLSHGLTFENGAVRAKLGPGLGTDDSGRSVVR 360
TGRGLRVANGQVQIFSGRGTAIGTDSSLTLNIRAPLQFSG 400
        410       420       430       440
PALTASLQGSGPITYNSNNGTFGLSIGPGMWVDQNRLQVN 440
PGAGLVFQGNNLVPNLADPLAISDSKISLSLGPGLTQASN 480
ALTLSLGNGLEFSNQAVAIKAGRGLRFESSSQALESSLTV 520
GNGLTLTDTVIRPNLGDGLEVRDNKIIVKLGANLRFENGA 560
VTAGTVNPSAPEAPPTLTAEPPLRASNSHLQLSLSEGLVV 600
        610       620       630       640
HNNALALQLGDGMEVNQHGLTLRVGSGLQMRDGILTVTPS 640
GTPIEPRLTAPLTQTENGIGLALGAGLELDESALQVKVGP 680
GMRLNPVEKYVTLLLGPGLSFGQPANRTNYDVRVSVEPPM 720
VFGQRGQLTFLVGHGLHIQNSKLQLNLGQGLRTDPVTNQL 760
EVPLGQGLEIADESQVRVKLGDGLQFDSQARITTAPNMVT 800
        810       820       830       840
ETLWTGTGSNANVTWRGYTAPGSKLFLSLTRFSTGLVLGN 840
MTIDSNASFGQYINAGHEQIECFILLDNQGNLKEGSNLQG 880
TWEVKNNPSASKAAFLPSTALYPILNESRGSLPGKNLVGM 920
QAILGGGGTCTVIATLNGRRSNNYPAGQSIIFVWQEFNTI 960
ARQPLNHSTLTFSYWT 976
```

FIGURE 14

```
            10         20         30         40
    ....|....|....|....|....|....|....|....|
MKRARWDPVYPFSEERLVPLPPFIEAGKGLKSEGLILSLN    40
FTDPITINQTGFLTVKLGDGIFINGEGGLSSTAPKVKVPL    80
TVSDETLQLLLSNSLTTESDSLALKQPQLPLKINDEGSLV   120
LNLNTPLNLQNERLSLNVSNPLKIAADSLTINLKEPLGLQ   160
NESLGLNLSDPMNITPEGNLGIKLKNPMKVEESSLALNYK   200
           210        220        230        240
    ....|....|....|....|....|....|....|....|
NPLAISNDALSINIANPLTVNTSGSLGISYSTPLRISNNA   240
LSLFIGKPLGLGTDGSLTVNLTRPLVCRQNTLAINYSAPL   280
VSLQDNLTLSYAQPLTVSDNSLRLSLNSPLNTNSDGKLSV   320
NYSNPLVVTDSNLTLSVKKPVMINNTGNVDLSFTAPIKLN   360
DAEQLTLETTEPLEVADNALKLKLGKGLTVSNNALTLNLG   400
           410        420        430        440
    ....|....|....|....|....|....|....|....|
NGLTFQQGLLQIKTNSSLGFNASGELSTATKQGTITVNFL   440
STTPIAFGWQIIPTTVAFIYILSGTQFTPQSPVTSLGFQP   480
PQDFLDFFVLSPFVTSVTQIVGNDVKVIGLTISKNQSTIT   520
MKFTSPLAENVPVSMFTAHQFRQ                    544
```

FIGURE 15

```
          10         20         30         40
    |....|....|....|....|....|....|....|....|
    MGPKKQKRELPEDFDPVYPYDVPOLQINPPFVSGDGFNQS   40
    VDGVLSLHIAPPLVFQNTRALTLAFGGGLQLSGKQLVVAT   80
    EGSGLTTNPDGKLVLKVKSPITLTAEGISLSLGPGLSNSE  120
    TGLSLQVTAPLQFQGNALTLPLAAGLQNTDGGMGVKLGSG  160
    LTTDNSQAVTVQVGNGLQLNGEGQLTVPATAPLVSGSAGI  200
         210        220        230        240
    |....|....|....|....|....|....|....|....|
    SFNYSSNDFVLDNDSLSLRPKAISVTPPLQSTEDTISLNY  240
    SNDFSVDNGALTLAPTFKPYTLWTGASPTANVILTNTTTP  280
    NGTFFLCLTRVGGLVLGSFALKSSIDLTSMTKKVNFIFDG  320
    AGRLQSDSTYKGRFGFRSNDSVIEPTAAGLSPAWLMPSTF  360
    IYPRNTSGSSLTSFVYINQTYVHVDIKVNTLSTNGYSLEF  400
         410        420        430        440
    |....|....|....|....|....|....|....|....|
    NFQNMSFSAPFSTSYGTFCYVPRRTTHRPRHGPFSLRERR  440
    HLFQLLQQ                                  448
```

FIGURE 16

```
            10        20        30        40
MKRTRRALPANYDPVYPYDAPGSSTQPPFFNNKQGLTESP  40
PGTLAVNVSPPLTFSTLGAIKLSTGPGLTLNEGKLQASLG  80
PGLITNTEGQITVENVNKVLSFTSPLHKNENTVSLALGDG  120
LEDENGTLKVTFPTPPPLQFSPPLTKTGGTVSLPLQDSM   160
QVTNGKLGVKPTTYAPPLKKTDQQVSLQVGSGLTVINEQL  200
           210       220       230       240
QAVQPPATTYNEPLSKTDNSVSLQVGAGLAVQSGALVATP  240
PPPLTFTSPLEKNENTVSLQVGAGLSVQNNALVATPPPPL  280
TFAYPLVKNDNHVALSAGSGLRISGGSLTVATGPGLSHQN  320
GTIGAVVGAGLKFENNAILAKLGNGLTIRDGAIEATQPPA  360
APITLWTGPGPSINGFINDTPVIRCFICLTRDSNLVTVNA  400
           410       420       430       440
SFVGEGGYRIVSPTQSQFSLIMEFDQFGQLMSTGNINSTT  440
TWGEKPWGNNTVQPRPSHTWKLCMPNREVYSTPAATISRC  480
GLDSIAVDGAPSRSIDCMLIINKPKGVATYTLTFRFLNFN  520
RLSGGTLFKTDVLTFTYVGENQ                    542
```

```
         M K R S R X X X P X P X D P X X L Y P X P X X X P Q X D X F    Majority
                    10              20              30
1        M S V S S C S C P S A P T I F M L L Q M K R A R P S E D T F    HAd5F.PRO
1        M K R S V P Q D F N L V Y P Y K A K R P N I M P P F F D R N    BAV3F.pro
1        M G P K K Q K R E L P E D F D P V Y P Y D V P Q L Q I N P P    PAV3F.pro
1        M K R T R R A L P A N Y D P V Y P Y D A P G S S T Q P P F F    CAV2F.pro
1        M K R A R W D P V Y P F S E E R L V P L P P F I E A G K G L    OAd287.PRO N X V G X X X X X X X X X V X X X L T P P F L X X X L G X X    Majority
                    40              50              60
31       N P V Y P Y D T E T G P P T V P F L T P P F V S P N G F Q E    HAd5F.PRO
31       G F V E N Q E A T L A M L V E K P L T F D K E G A L T L G V    BAV3F.pro
31       F V S G D G F N Q S V D G V L S L H I A P P L V F D N T R A    PAV3F.pro
31       N N K Q G L T E S P P G T L A V N V S P P L T F S T L G A I    CAV2F.pro
31       K S E G L I L S L N F T D P I T I N Q T G F L T V K L G D G    OAd287.PRO X X X X G X G G L L L E G K X X X V X X X G L X L T T X L X    Majority
                    70              80              90
61       S P P G V L S L R L S E P L V T S N G M L A L K M G N G L S    HAd5F.PRO
61       G R G I R I N P A G L L E T N D L A S A V F P P L A S D E A    BAV3F.pro
61       L T L A F G G G L Q L S G K Q L V V A T E G S G L T T N P D    PAV3F.pro
61       K L S T G P G L T L N E G K L Q A S L G P G L I T N T E G Q    CAV2F.pro
61       I F I N G E G G L S S T A P K V K V P L T V S D E T L Q L L    OAd287.PRO G X V X L N X K S X S X T T X X P X L X K T G S G L S L D X    Majority
                    100             110             120
91       L D E A G N L T S Q N V T T V S P P L K K T K S N I N L E I    HAd5F.PRO
91       G N V T L N M S D G L Y T K D N K L A V K V G P G L S L D S    BAV3F.pro
91       G K L V L K V K S P I T L T A E G I S L S L G P G L S N S E    PAV3F.pro
91       I T V E N V N K V L S F T S P L H K N E N T V S L A L G D G    CAV2F.pro
91       L S N S L T T E S D S L A L K Q P Q L P L K I N D E G S L V    OAd287.PRO L N L L T V T T X X L X X X X X A P L X P L X X A L X S T T    Majority
                    130             140             150
121      S A P L T V T S E A L T V A A A A P L M V A G N T L T M Q S    HAd5F.PRO
121      N N A L Q V H T G D G L T V T D D K V S L N T Q A P L S T T    BAV3F.pro
121      T G L S L Q V T A P L Q F Q G N A L T L P L A A G L Q N T D    PAV3F.pro
121      L E D E N G T L K V T F P T P P P L Q F S P P L T K T G G      CAV2F.pro
121      L N L N T P L N L Q N E R L S L N V S N P L K I A A D S L T    OAd287.PRO
```

*FIG._17A*

```
        X A X L X L L G S X L X T L G X X X V T V X N G X P X L Q X    Majority
                    160             170             180
151     Q A P L T V H D S K L S I A T Q G P L T V S E G K L A L Q T    HAd5F.PRO
151     S A G L S L L L G P S L H L G E E E R L T V N T G A G L Q I    BAV3F.pro
151     G G M G V K L G S G L T T D N S Q A V T V Q V G N G L Q L N    PAV3F.pro
151     T V S L P L Q D S M Q V T N G K L G V K P T T Y A P P L K K    CAV2F.pro
151     I N L K E P L G L Q N E S L G L N L S D P M N I T P E G N L    OAd287.PRO G X X L L T V X V G S G L T V A S X X L X A A X X S N G X X    Majority
                    190             200             210
181     S G P L T T T D S S T L T I T A S P P L T T A T G S L G I D    HAd5F.PRO
181     S N N A L A V K V G S G I T V D A Q N Q L A A S L G D G L E    BAV3F.pro
181     G E G Q L T V P A T A P L V S G S A G I S F N Y S S N D F V    PAV3F.pro
181     T D Q Q V S L Q V G S G L T V I N E Q L A V Q P P A T T Y      CAV2F.pro
181     G I K L K N P M K V E E S S L A L N Y K N P L A I S N D A L    OAd287.PRO L X N X S X T L N X X G L V X G X L A S T X D T L S X L X      Majority
                    220             230             240
211     L K E P I Y T Q N G K L G L K Y G A P L H V T D D L N T L T    HAd5F.PRO
211     S R D N K T V V K A G P G L T I T N Q A L T V A T G N G L Q    BAV3F.pro
211     L D N D S L S L R P K A I S V T P P L Q S T E D T I S L N Y    PAV3F.pro
211     N E P L S K T D N S V S L Q V G A G L A V Q S G A L V A T P    CAV2F.pro
211     S I N I A N P L T V N T S G S L G I S Y S T P L R I S N N A    OAd287.PRO V N P F X G X X L N L T X X Q T L X X X X L X X L V X X N N    Majority
                    250             260             270
241     V A T G P G V T I N N T S L Q T K V T G A L G F D S Q G N M    HAd5F.PRO
241     V N P E G Q L Q L N I T A G Q G L N F A N N S L A V E L G S    BAV3F.pro
241     S N D F S V D N G A L T L A P T F K P Y T L W T G A S P T A    PAV3F.pro
241     P P P L T F T S P L E K N E N T V S L Q V G A G L S V Q N N    CAV2F.pro
241     L S L F I G K P L G L G T D G S L T V N L T R P L V C R Q N    OAd287.PRO X L X X T P G X P L V S L Y P L L X L D V X X P L X A S X A    Majority
                    280             290             300
271     Q L N V A G G L R I D S Q N R R L I L D V S Y P F D A Q N Q    HAd5F.PRO
271     G L H F P P G Q N Q V S L Y P G D G I D I R D N R V T V P A    BAV3F.pro
271     N V I L T N T T T P N G T F F L C L T R V G G L V L G S F A    PAV3F.pro
271     A L V A T P P P P L T F A Y P L V K N D N H V A L S A G S G    CAV2F.pro
271     T L A I N Y S A P L V S L Q D N L T L S Y A Q P L T V S D N    OAd287.PRO
```

FIG._17B

```
      L X X L X G L X P L X T N S X G X L D X N Y S X X L V L T X    Majority
                    310           320           330
301   L N L R L G Q G P L F I N S A H N L D I N Y N K G L Y L F T    HAd5F.PRO
301   G P G L R M L N H Q L A V A S G D G L E V H S D T L R L K L    BAV3F.pro
301   L K S S I D L T S M T K K V N F I F D G A G R L Q S D S T Y    PAV3F.pro
301   L R I S G G S L T V A T G P G L S H Q N G T I G A V V G A G    CAV2F.pro
301   S L R L S L N S P L N T N S D G K L S V N Y S N P L V V T D    OAd287.PRO S X X X X F X X X A V L I N X T G X X D X A X X X A X I X X X  Majority
                    340           350           360
331   A S N N S K K L E V N L S T A K G L M F D A T A I A I N A G    HAd5F.PRO
331   S H G L T F E N G A V R A K L G P G L G T D D S G R S V V R    BAV3F.pro
331   K G R F G F R S N D S V I E P T A A G L S P A W L M P S T F    PAV3F.pro
331   L K F E N N A I L A K L G N L T I R D G A I E A T Q P P A      CAV2F.pro
331   S N L T L S V K K P V M I N N T G N V D L S F T A P I K L N    OAd287.PRO D G X X L T S G N G P X X N V X I N X T X V G L D F X L T T    Majority
                    370           380           390
361   D G L E F G S P N A P N T N P L K T K I G H G L E F D S N K    HAd5F.PRO
361   T G R G L R V A N G Q V Q I F S G R G T A I G T D S S L T L    BAV3F.pro
361   I Y P R N T S G S S L T S F V Y I N Q T Y V H V D I K V N T    PAV3F.pro
361   A P I T L W T G P G P S I N G F I N D T P V I R G F I C L T    CAV2F.pro
361   D A E Q L T L E T T E P L E V A D N A L K L K L G K G L T V    OAd287.PRO X X X A L L X X X G S P L T X G X X X X G S K T N S S L X L    Majority
                    400           410           420
391   A M V P K L G T G L S F D S T G A I T V G N K N N D K L T L    HAd5F.PRO
391   N I R A P L Q F S G P A L T A S L Q G S G P I T Y N S N N G    BAV3F.pro
391   L S T N G Y S L F N F Q N M S F S A P F S T S Y G T F C Y      PAV3F.pro
391   R D S N L V T V N A S F V G E G G Y R I V S P T Q S Q F S L    CAV2F.pro
391   S N N A L T L N L G N G L T F Q Q G L L Q I K T N S S L G F    OAd287.PRO X X X X X X S P X X X X X X N X X X X L T L X X L X F G X N    Majority
                    430           440           450
421   W T T P A P S P N C R L N A E K D A K L T L V L T K C G S Q    HAd5F.PRO
421   T F G L S I G P G M W V D Q N R L Q V N P G A G L V F Q G N    BAV3F.pro
421   V P R R T T H R P R H G P F S L R E R R H L F Q L L Q Q        PAV3F.pro
421   I M E F D Q F G Q L M S T G N I N S T T T W G E K P W G N N    CAV2F.pro
421   N A S G E L S T A T K Q G T I T V N F L S T T P I A F G W Q    OAd287.PRO
```

FIG._17C

```
            I L X T X X A X X X K L S X X X I S X X S X P A X L I X R X    Majority
                     460             470             480
     451    I L A T V S V L A V K G S L A P I S G T V Q S A H L I I R F    HAd5F.PRO
     451    N L V P N L A D P L A I S D S K I S L S L G P G L T Q A S N    BAV3F.pro
     448                                                                   PAV3F.pro
     451    T V Q P R P S H T W K L C M P N R E V Y S T P A A T I S R C    CAV2F.pro
     451    I I P T T V A F I Y I L S G T Q F T P Q S P V T S L G F Q P    OAd287.PRO X L D X X L X N G L X X X X X X V X X I X G X X X X V X X Y    Majority
                     490             500             510
     481    D E N G V L L N N S F L D P E Y W N F R N G D L T E G T A Y    HAd5F.PRO
     481    A L T L S L G N G L E F S N Q A V A I K A G R G L R F E S S    BAV3F.pro
     448                                                                   PAV3F.pro
     481    G L D S I A V D G A P S R S I D C M L I I N K P K G V A T Y    CAV2F.pro
     481    P Q D F L D F F V L S P F V T S V T Q I V G N D V K V I G L    OAd287.PRO T X A X X F S X X X X X X X X X L X K T X X X N X X X X E      Majority
                     520             530             540
     511    T N A V G F M P N L S A Y P K S H G K T A K S N I V S Q V Y    HAd5F.PRO
     511    S Q A L E S S L T V G N G L T L T D T V I R P N L G D G L E    BAV3F.pro
     448                                                                   PAV3F.pro
     511    T L T F R F L N F N R L S G G T L F K T D V L T F T Y V G E    CAV2F.pro
     511    T I S K N Q S T I T M K F T S P L A E N V P V S M F T A H Q    OAd287.PRO X R - - - - - - - - - - - - - - - - - - - - - - - - - - -      Majority
                     550             560             570
     541    L N G D K T K P V T L T I T L N G T Q E T G D T T P S A Y S    HAd5F.PRO
     541    V R D N K I I V K L G A N L R F E N G A V T A G T V N P S A    BAV3F.pro
     448                                                                   PAV3F.pro
     541    N Q                                                            CAV2F.pro
     541    F R Q                                                          OAd287.PRO

- - - - - - - - - - - - - - - - - - - - - - - - - - - - -      Majority
                     580             590             600
     571    M S F S W D W S G H N Y I N E I F A T S S Y T F S Y I A Q E    HAd5F.PRO
     571    P E A P P T L T A E P P L R A S N S H L Q L S L S E G L V V    BAV3F.pro
     448                                                                   PAV3F.pro
     542                                                                   CAV2F.pro
     544                                                                   OAd287.PRO
```

FIG._17D

|      | 610              | 620              | 630        | Majority     |
|------|------------------|------------------|------------|--------------|
| 600  |                  |                  |            | HAd5F.PRO    |
| 601  | H N N A L A L Q L G D G M E V N Q H G L T L R V G S G L Q M | | | BAV3F.pro |
| 448  |                  |                  |            | PAV3F.pro    |
| 542  |                  |                  |            | CAV2F.pro    |
| 544  |                  |                  |            | OAd287.PRO   |

|      | 640              | 650              | 660        | Majority     |
|------|------------------|------------------|------------|--------------|
| 600  |                  |                  |            | HAd5F.PRO    |
| 631  | R D G I L T V T P S G T P I E P R L T A P L T Q T E N G I G | | | BAV3F.pro |
| 448  |                  |                  |            | PAV3F.pro    |
| 542  |                  |                  |            | CAV2F.pro    |
| 544  |                  |                  |            | OAd287.PRO   |

|      | 670              | 680              | 690        | Majority     |
|------|------------------|------------------|------------|--------------|
| 600  |                  |                  |            | HAd5F.PRO    |
| 661  | L A L G A G L E L D E S A L Q V K V G P G M R L N P V E K Y | | | BAV3F.pro |
| 448  |                  |                  |            | PAV3F.pro    |
| 542  |                  |                  |            | CAV2F.pro    |
| 544  |                  |                  |            | OAd287.PRO   |

|      | 700              | 710              | 720        | Majority     |
|------|------------------|------------------|------------|--------------|
| 600  |                  |                  |            | HAd5F.PRO    |
| 691  | V T L L L G P G L S F G Q P A N R T N Y D V R V S V E P P M | | | BAV3F.pro |
| 448  |                  |                  |            | PAV3F.pro    |
| 542  |                  |                  |            | CAV2F.pro    |
| 544  |                  |                  |            | OAd287.PRO   |

|      | 730              | 740              | 750        | Majority     |
|------|------------------|------------------|------------|--------------|
| 600  |                  |                  |            | HAd5F.PRO    |
| 721  | V F G Q R G Q L T F L V G H G L H I Q N S K L Q L N L G Q G | | | BAV3F.pro |
| 448  |                  |                  |            | PAV3F.pro    |
| 542  |                  |                  |            | CAV2F.pro    |
| 544  |                  |                  |            | OAd287.PRO   |

FIG._17E

```
                    - - - - - - - - - - - - - - - - - - - - - - - - - - -      Majority
                          760              770              780
600     ─────────────────────────────────────────────────────────────         HAd5F.PRO
751     L R T D P V T N Q L E V P L G Q G L E I A D E S Q V R V K L           BAV3F.pro
448                                                                           PAV3F.pro
542                                                                           CAV2F.pro
544                                                                           OAd287.PRO

- - - - - - - - - - - - - - - - - - - - - - - - - - -      Majority
                          790              800              810
600     ─────────────────────────────────────────────────────────────         HAd5F.PRO
781     G D G L Q F D S Q A R I T T A P N M V T E T L W T G T G S N           BAV3F.pro
448                                                                           PAV3F.pro
542                                                                           CAV2F.pro
544                                                                           OAd287.PRO

- - - - - - - - - - - - - - - - - - - - - - - - - - -      Majority
                          820              830              840
600     ─────────────────────────────────────────────────────────────         HAd5F.PRO
811     A N V T W R G Y T A P G S K L F L S L T R F S T G L V L G N           BAV3F.pro
448                                                                           PAV3F.pro
542                                                                           CAV2F.pro
544                                                                           OAd287.PRO

- - - - - - - - - - - - - - - - - - - - - - - - - - -      Majority
                          850              860              870
600     ─────────────────────────────────────────────────────────────         HAd5F.PRO
841     M T I D S N A S F G Q Y I N A G H E Q I E C F I L L D N Q G           BAV3F.pro
448                                                                           PAV3F.pro
542                                                                           CAV2F.pro
544                                                                           OAd287.PRO

- - - - - - - - - - - - - - - - - - - - - - - - - - -      Majority
                          880              890              900
600     ─────────────────────────────────────────────────────────────         HAd5F.PRO
871     N L K E G S N L Q G T W E V K N N P S A S K A A F L P S T A           BAV3F.pro
448                                                                           PAV3F.pro
542                                                                           CAV2F.pro
544                                                                           OAd287.PRO
```

FIG._17F

|       |                                          | Majority |
|-------|------------------------------------------|----------|
|       | 910           920           930          |          |
| 600   |                                          | HAd5F.PRO |
| 901   | L Y P I L N E S R G S L P G K N L V G M Q A I L G G G G T C | BAV3F.pro |
| 448   |                                          | PAV3F.pro |
| 542   |                                          | CAV2F.pro |
| 544   |                                          | OAd287.PRO |

|       |                                          | Majority |
|-------|------------------------------------------|----------|
|       | 940           950           960          |          |
| 600   |                                          | HAd5F.PRO |
| 931   | T V I A T L N G R R S N N Y P A G Q S I I F V W Q E F N T I | BAV3F.pro |
| 448   |                                          | PAV3F.pro |
| 542   |                                          | CAV2F.pro |
| 544   |                                          | OAd287.PRO |

|       |                          | Majority |
|-------|--------------------------|----------|
|       | 970                      |          |
| 600   |                          | HAd5F.PRO |
| 961   | A R Q P L N H S T L T F S Y W T | BAV3F.pro |
| 448   |                          | PAV3F.pro |
| 542   |                          | CAV2F.pro |
| 544   |                          | OAd287.PRO |

*FIG._17G*

MODIFIED BOVINE ADENOVIRUS HAVING ALTERED TROPISM

CROSS-REFERENCE TO RELATED APPLICATIONS

This application claims the benefit of U.S. Provisional Application Ser. No. 60/208,678, filed May 31, 2000, hereby incorporated herein in its entirety.

TECHNICAL FIELD

This invention relates to bovine adenoviruses comprising a modification in a capsid protein and which exhibit altered tropism. The present invention also relates to methods of making and using bovine adenoviruses having altered tropism.

BACKGROUND ART

The adenoviruses cause enteric or respiratory infection in humans as well as in domestic and laboratory animals. The bovine adenoviruses (BAV) comprise at least nine serotypes divided into two subgroups. These subgroups have been characterized based on enzyme-linked immunoassays (ELISA), serologic studies with immunofluorescence assays, virus-neutralization tests, immunoelectron microscopy, by their host specificity and clinical syndromes. Subgroup 1 viruses include BAV 1, 2, 3 and 9 and grow relatively well in established bovine cells compared to subgroup 2 which includes BAV 4, 5, 6, 7 and 8.

BAV3 was first isolated in 1965 and is the best characterized of the BAV genotypes, containing a genome of approximately 35 kb (Kurokawa et al (1978) *J. Virol.* 28:212–218). Reddy et al. (1998, *Journal of Virology,* 72:1394) disclose nucleotide sequence, genome organization, and transcription map of BAV3. Reddy et al. (1999, *Journal of Virology,* 73: 9137) disclose a replication-defective BAV3 as an expression vector. BAV3, a representative of subgroup 1 of BAVs (Bartha (1969) *Acta Vet. Acad. Sci. Hung.* 19:319–321), is a common pathogen of cattle usually resulting in subclinical infection (Darbyshire et al. (1965), *J. Comp. Pathol.* 75:327–330), though occasionally associated with a more serious respiratory tract infection (Darbyshire et al., 1966 *Res. Vet. Sci.* 7:81–93; Mattson et al., 1988 *J. Vet Res* 49:67–69). Like other adenoviruses, BAV3 is a non-enveloped icosahedral particle of 75 nm in diameter (Niiyama et al. (1975) *J. Virol.* 16:621–633) containing a linear double-stranded DNA molecule. BAV3 can produce tumors when injected into hamsters (Darbyshire, 1966 *Nature* 211:102) and viral DNA can efficiently effect morphological transformation of mouse, hamster or rat cells in culture (Tsukamoto and Sugino, 1972 *J. Virol.* 9:465–473; Motoi et al., 1972 *Gann* 63:415–418). Cross hybridization was observed between BAV3 and human adenovirus type 2 (HAd2) (Hu et al., 1984 *J. Virol.* 49:604–608) in most regions of the genome including some regions near but not at the left end of the genome.

Porcine adenovirus (PAV) infection has been associated with encephalitis, pneumonia, kidney lesions and diarrhea. See Derbyshire (1992) In: "Diseases of Swine" (ed. Leman et al.), 7th edition, Iowa State University Press, Ames, Iowa. pp. 225–227. It has been shown that PAV is capable of stimulating both humoral response and a mucosal antibody responses in the intestine of infected piglets. Tuboly et al. (1993) *Res. in Vet. Sci.* 54:345–350. Cross-neutralization studies have indicated the existence of at least five serotypes of PAV. See Derbyshire et al. (1975) *J. Comp. Pathol.* 85:437–443; and Hirahara et al. (1990) *Jpn. J. Vet. Sci.* 52:407–409. Previous studies of the PAV genome have included the determination of restriction maps for PAV Type 3 (PAV-3) and cloning of restriction fragments representing the complete genome of PAV-3. See Reddy et al. (1993) *Intervirology* 36:161–168. In addition, restriction maps for PAV-1 and PAV-2 have been determined. See Reddy et al. (1995b) *Arch. Virol.* 140:195–200.

Nucleotide sequences have been determined for segments of the genome of various PAV serotypes. Sequences of the E3, pVIII and fiber genes of PAV-3 were determined by Reddy et al. (1995) *Virus Res.* 36:97–106. The E3, pVIII and fiber genes of PAV-1 and PAV-2 were sequenced by Reddy et al. (1996) *Virus Res.* 43:99–109, while the PAV-4 E3, pVIII and fiber gene sequences were determined by Kleiboeker (1994) *Virus Res.* 31:17–25. The PAV-4 fiber gene sequence was determined by Kleiboeker (1995) *Virus Res.* 39:299–309. Inverted terminal repeat (ITR) sequences for all five PAV serotypes (PAV-1 through PAV-5) were determined by Reddy et al (1995) *Virology* 212:237–239. The PAV-3 penton sequence was determined by McCoy et al. (1996) *Arch. Virol.* 141:1367–1375. The nucleotide sequence of the E1 region of PAV-4 was determined by Kleiboeker (1995) *Virus Res.* 36:259–268. The sequence of the protease (23K) gene of PAV-3 was determined by McCoy et al. (1996) *DNA Seq.* 6:251–254. The sequence of the PAV-3 hexon gene (and the 14 N-terminal codons of the 23K protease gene) has been deposited in the GenBank database under accession No. U34592. The sequence of the PAV-3 100K gene has been deposited in the GenBank database under accession No. U82628. The sequence of the PAV-3 E4 region has been determined by Reddy et al. (1997) *Virus Genes* 15:87–90. Vrati et al. (1995, *Virology,* 209:400–408) disclose sequences for ovine adenovirus.

At least 47 serotypes of human adenoviruses have been described. Reviews of the most common serotypes associated with particular diseases have been published. See for example, Foy H. M. (1989) *Adenoviruses* In Evans A S (ed). *Viral Infections of Humans.* New York, Plenum Publishing, pp 77–89 and Rubin B. A. (1993) *Clinical picture and epidemiology of adenovirus infections,* Acta Microbiol. Hung 40:303–323. The capsid of a human adenovirus demonstrates icosahedral symmetry and contains 252 capsomers. The capsomers consist of 240 hexons and 12 pentons with a projecting fiber on each of the pentons. The pentons and hexons are each derived from different viral polypeptides. The fibers, which are responsible for type-specific antibodies, vary in length among human strains. The hexons are group specific complement-fixing antibodies, whereas the pentons are especially active in hemgglutination (Plotkin and Orenstein, *Vaccines,* 3rd edition, W. B. Saunders Company Philadelphia, pp609–623). The fiber region assumes a homotrimeric conformation which is necessary for association of the mature fiber protein with the penton base in the formation of the adenovirus capsid. Fiber associates with penton base by virtue of non-covalent interactions between the amino terminus of the fiber trimer and a conserved domain within the penton base. It has been shown that the globular carboxyterminal knob domain of the adenovirus fiber protein is the ligand for attachment to the adenovirus primary cellular receptor (Krasnykh et al. (1996) Journal of Virology, 70:6839.). The distal, C-terminal domain of the trimeric fiber molecule terminates in a knob which binds with high affinity to a specific primary receptor. After binding, Arg-Gly-Asp (RGD) motifs in the penton base interact with cellular integrins of the $\alpha v \beta 3$ and $\alpha v \beta 5$ types which function as secondary receptors. This interaction triggers cellular internalization whereby the virion resides within the endosome. The endosome membrane is lysed in a process mediated by the penton base, releasing the contents of the endosome to the cytoplasm. During these processes, the virion is gradually uncoated and the adenovirus DNA is transported into the nucleus (Shayakhmetov et al. (2000) *Journal of Virology* 74:2567–2583).

For general background references regarding adenovirus and development of adenoviral vector systems, see Graham et al. (1973) *Virology* 52:456–467; Takiff et al. (1981) *Lancet* 11:832–834; Berkner et al. (1983) *Nucleic Acid Research* 11: 6003–6020; Graham (1984) *EMBO J* 3:2917–2922; Bett et al. (1993) *J. Virology* 67:5911–5921; and Bett et al. (1994) *Proc. Natl. Acad. Sci. USA* 91:8802–8806.

Adenoviruses generally undergo a lytic replication cycle following infection of a host cell. In addition to lysing the infected cell, the replicative process of adenovirus blocks the transport and translation host cell mRNA, thus inhibiting cellular protein synthesis. For a review of adenoviruses and adenovirus replication, see Shenk, T. and Horwitz, M. S., *Virology*, third edition, Fields, B. N. et al., eds., Raven Press Limited, New York (1996), Chapters 67 and 68, respectively.

The application of genetic engineering has resulted in several attempts to prepare adenovirus expression systems for obtaining vaccines. Examples of such research include the disclosures in U.S. Pat. No. 4,510,245 of an adenovirus major late promoter for expression in a yeast host; U.S. Pat. No. 4,920,209 on a live recombinant adenovirus type 7 with a gene coding for hepatitis-B surface antigen located at a deleted early region 3; European Patent 389 286 on a non-defective human adenovirus 5 recombinant expression system in human cells for HCMV major envelope glycoprotein; WO 91/11525 on live non-pathogenic immunogenic viable canine adenovirus in a cell expressing E1A proteins; and French Patent 2 642 767 on vectors containing a leader and/or promoter from the E3 region of adenovirus 2. U.S. Pat. Nos. 6,001,591 and 5,820,868 and International Publication Number WO 95/16048 disclose recombinant protein production in bovine adenovirus expression vector systems. U.S. Pat. No. 5,922,576 discloses systems for generating recombinant adenoviruses.

Krasnykh et al. (1996, *Journal of Virology*, 70:6839), Zabner et al. (1999) *Journal of Virology*, 73:8689), and Shayakhmetov et al. supra report generation of human adenovirus vectors with modified fiber regions. Xu et al. (1998, *Virology*, 248:156–163) disclose an ovine adenovirus carrying the fiber protein cell binding domain of human Adenovirus Type 5.

The disclosure of all patents and publications cited herein are incorporated by reference in their entirety.

DISCLOSURE OF THE INVENTION

The present invention provides adenoviruses, preferably bovine adenoviruses, comprising a modification in a polynucleotide encoding a capsid protein, or fragment thereof, wherein said protein, or fragment thereof, is associated with tropism and wherein said modification is associated with altered tropism. The present invention further provides host cells and methods comprising the modified adenoviruses. Accordingly, the present invention provides bovine adenovirus vectors comprising a modification in a polynucleotide encoding a capsid protein, or fragment thereof, wherein said protein, or fragment thereof, is associated with tropism and wherein said modification is associated with altered tropism. In some embodiments, the polynucleotide encoding a capsid protein, or fragment thereof, is replaced with a polynucleotide encoding a heterologous mammalian capsid protein, or fragment thereof. The capsid protein, or fragment thereof, includes adenovirus penton, hexon or fiber proteins, or fragments thereof. In some embodiments, the modification is in a polynucleotide encoding the knob region of a fiber protein. In other embodiments, a polynucleotide encoding a bovine adenovirus penton, hexon and/or fiber protein(s) is replaced with at least one polynucleotide encoding a heterologous mammalian adenovirus penton, hexon and/or fiber protein(s), respectively. In additional embodiments, a polynucleotide encoding a bovine adenovirus penton protein, or fragment thereof, is replaced with at least one polynucleotide encoding a heterologous mammalian adenovirus penton protein, or fragment thereof; a polynucleotide encoding a bovine adenovirus hexon protein, or fragment thereof, is replaced with at least one polynucleotide encoding a heterologous mammalian adenovirus hexon protein, or fragment thereof, or a polynucleotide encoding a bovine adenovirus fiber protein, or fragment thereof, such as a knob region, is replaced with at least one polynucleotide encoding a heterologous mammalian adenovirus fiber protein, or fragment thereof, such as a heterologous knob region of a fiber protein.

In further embodiments, heterologous mammalian adenoviruses include bovine, porcine, ovine, canine or human adenovirus. In additional embodiments, bovine adenoviruses include sub-type 1 adenovirus, and in particular BAV3, or sub-type 2 adenovirus. In other embodiments, the bovine adenovirus vector further comprises a polynucleotide encoding a heterologous protein. In some embodiments, the heterologous protein is a therapeutic protein. In other embodiments, the heterologous protein includes cytokines; lymphokines; membrane receptors recognized by pathogenic organisms, dystrophins; insulin; proteins participating in cellular ion channels; antisense RNAs; proteins capable of inhibiting the activity of a protein produced by a pathogenic gene, a protein inhibiting an enzyme activity, protein variants of pathogenic proteins; antigenic epitopes; major histocompatibility complex classes I and II proteins; antibodies; immunotoxins; toxins; growth factors or growth hormones; cell receptors or their ligands; tumor suppressors; cellular enzymes; or suicide genes. In yet other embodiments, an adenovirus vector lacks E1 function. In additional embodiments, an adenovirus vector has a deletion in part or all of the E1 gene region. In further embodiments, the adenovirus vector has a deletion of part or all of the E3 gene region. In yet further embodiments, a polynucleotide encoding a heterologous protein is inserted in the adenovirus E1 gene region. In other embodiments, a polynucleotide encoding a heterologous protein is inserted in the adenovirus E3 gene region. In further embodiments, an adenovirus vector is replication-defective, and in yet further embodiments, an adenovirus vector is replication-competent. The present invention also encompasses host cells comprising a bovine adenovirus vector having a modification in a polynucleotide encoding a capsid protein, or fragment thereof.

The present invention also provides methods of producing a recombinant bovine adenovirus vector comprising a modification in a polynucleotide encoding a capsid protein, or fragment thereof, comprising the steps of, obtaining a bovine adenovirus vector; and introducing a modification into a polynucleotide encoding a capsid protein, or fragment thereof, wherein said capsid protein, or fragment thereof, is associated with tropism and wherein said modification is associated with altered tropism. In some embodiments, the modification is a replacement of at least one polynucleotide encoding a bovine adenovirus penton, hexon and/or fiber protein, or fragment thereof, with a heterologous mammalian penton, hexon and/or fiber protein, or fragment thereof. In other embodiments, the modification is a replacement of a polynucleotide encoding a knob region of a fiber protein. In further embodiments, the adenovirus vector further comprises a polynucleotide encoding a heterologous protein.

The present invention further provides recombinant bovine adenoviruses comprising a modification in a capsid protein, or fragment thereof wherein said capsid protein, or fragment thereof, is associated with tropism and wherein said modification is associated with altered tropism. In further embodiments, recombinant adenoviruses comprise polynucleotides encoding a heterologous protein. In further embodiments, a polynucleotide encoding a heterologous protein is inserted in the adenovirus E1 gene region; in yet further embodiments, a polynucleotide encoding a heterologous protein is inserted in the adenovirus E3 gene region. In some embodiments, a recombinant adenovirus is replication-competent and in other embodiments, a recombinant adenovirus is replication-defective. In some embodiments, a recombinant adenovirus comprises a replacement of at least one polynucleotide encoding a bovine adenovirus penton, hexon and/or fiber protein(s), or fragment thereof, with a heterologous mammalian penton, hexon and/or fiber protein(s), or fragment thereof In yet further embodiments, a recombinant adenovirus comprises a modification in a knob region of a fiber protein.

The present invention also provides immunogenic compositions comprising a bovine adenovirus wherein said adenovirus comprises a polynucleotide encoding a modification in a capsid protein, or fragment thereof, and wherein said protein, or fragment thereof, is associated with tropism and wherein said modification is associated with altered tropism In some embodiments, the capsid protein, or fragment thereof, includes penton, hexon or fiber protein(s), or a fragment thereof, of an adenovirus. In some embodiments of immunogenic compositions, the modification comprises a replacement of a polynucleotide encoding a bovine capsid protein, or fragment thereof with a polynucleotide encoding a heterologous mammalian adenovirus capsid protein, or fragment thereof. In other embodiments of immunogenic compositions, the modification comprises a replacement of a polynucleotide encoding a bovine knob region of a fiber protein with a polynucleotide encoding a heterologous mammalian adenovirus knob region of a fiber protein. In other embodiments, the bovine adenovirus is a sub-type 1 adenovirus, in particular, BAV3, or a sub-type 2 adenovirus. In additional embodiments, immunogenic compositions comprise a bovine adenovirus comprises a polynucleotide encoding a heterologous protein. In other embodiments, immunogenic compositions comprise a bovine adenovirus comprising a polynucleotide encoding cytokines; lymphokines; membrane receptors recognized by pathogenic organisms, dystrophins; insulin; proteins participating in cellular ion channels; antisense RNAs; proteins capable of inhibiting the activity of a protein produced by a pathogenic gene, a protein inhibiting an enzyme activity, protein variants of pathogenic proteins; antigenic epitopes; major histocompatibility complex classes I and II proteins; antibodies; immunotoxins; toxins; growth factors or growth hormones; cell receptors or their ligands; tumor suppressors; cellular enzymes; or suicide genes.

The present invention also encompasses pharmaceutical compositions capable of inducing an immune response in a mammalian subject. In some embodiments, pharmaceutical compositions comprise an immunogenic composition comprising a bovine adenovirus having a modified capsid protein, or fragment thereof, wherein the protein, or fragment thereof, is associated with tropism and wherein the modification is associated with altered tropism In some embodiments of the pharmaceutical compositions, immunogenic compositions comprise bovine adenovirus vectors comprising a polynucleotide encoding a heterologous protein. In some embodiments, the heterologous protein is a therapeutic protein. In other embodiments, the pharmaceutical composition further comprises a pharmaceutically acceptable excipient.

The present invention also provides methods for eliciting an immune response in a mammalian host to protect against infection, the method comprising administering a pharmaceutical composition of the present invention to a mammalian host in need. The present invention also provides methods of gene delivery in a mammalian host, the methods comprising administering to the host a bovine adenovirus vector comprising a polynucleotide encoding a modified capsid protein, or fragment thereof, wherein the protein is associated with tropism and wherein the modification is associated with altered tropism and wherein the adenovirus vector further comprises a polynucleotide encoding a heterologous protein. In some embodiments, the heterologous polynucleotide encodes a therapeutic protein.

BRIEF DESCRIPTION OF THE DRAWINGS

FIGS. 1A–1S shows the complete nucleotide sequence of the BAV3 genome (SEQ ID NO: 1). In the polynucleotide sequence for BA V3, the penton regions starts at 12919 and ends at 14367; the hexon region starts at 17809 and ends at 20517; the fiber region starts at 27968 and ends at 30898. The knob domain of the fiber region starts after the 4 residues, TLWT, as shown in FIG. 4 (SEQ ID NO: 2).

FIGS. 5A–5B shows the analysis of BAV600 by Restriction Enzyme Bg/II digestion. FIG. 5A depicts a gel electrophoresis and FIG. 5B depicts a Southern Blot.

FIG. 6 shows the expression of HAV-5 fiber Knob by BAV600.

FIG. 7A show results of an MOI of 1 whereas FIG. 7B shows results of an MOI of 5.

FIG. 8 shows a FACS analysis of BAV304 and BAV600 transduction of Human cells.

FIG. 11 shows the neutralization of BAV600 by a monoclonal antibody specific for HAV-5 fiber knob region.

FIG. 12 depicts the amino acid sequence for Human adenovirus 5 (HAV-5) fiber protein (SEQ ID NO: 5).

FIG. 13 depicts the amino acid sequence for the Bovine Adenovirus-3 (BAV-3) fiber protein (SEQ ID NO: 6).

FIG. 14 depicts the amino acid sequence of Ovine Adenovirus 287 fiber protein (SEQ ID NO: 7).

FIG. 15 shows the amino acid sequence of Porcine Adenovirus-3 (PAV-3) fiber protein (SEQ ID NO: 8).

FIG. 16 shows the amino acid sequence of Canine Adenovirus-2 (CAV-2) fiber protein (SEQ ID NO: 9).

FIGS. 17A–17G (SEQ ID NO: 5–9) depicts an amino acid alignment of various mammalian adenovirus fiber regions using the clustal method of the Multialign program.

BEST MODE FOR CARRYING OUT THE INVENTION

Figure 2:
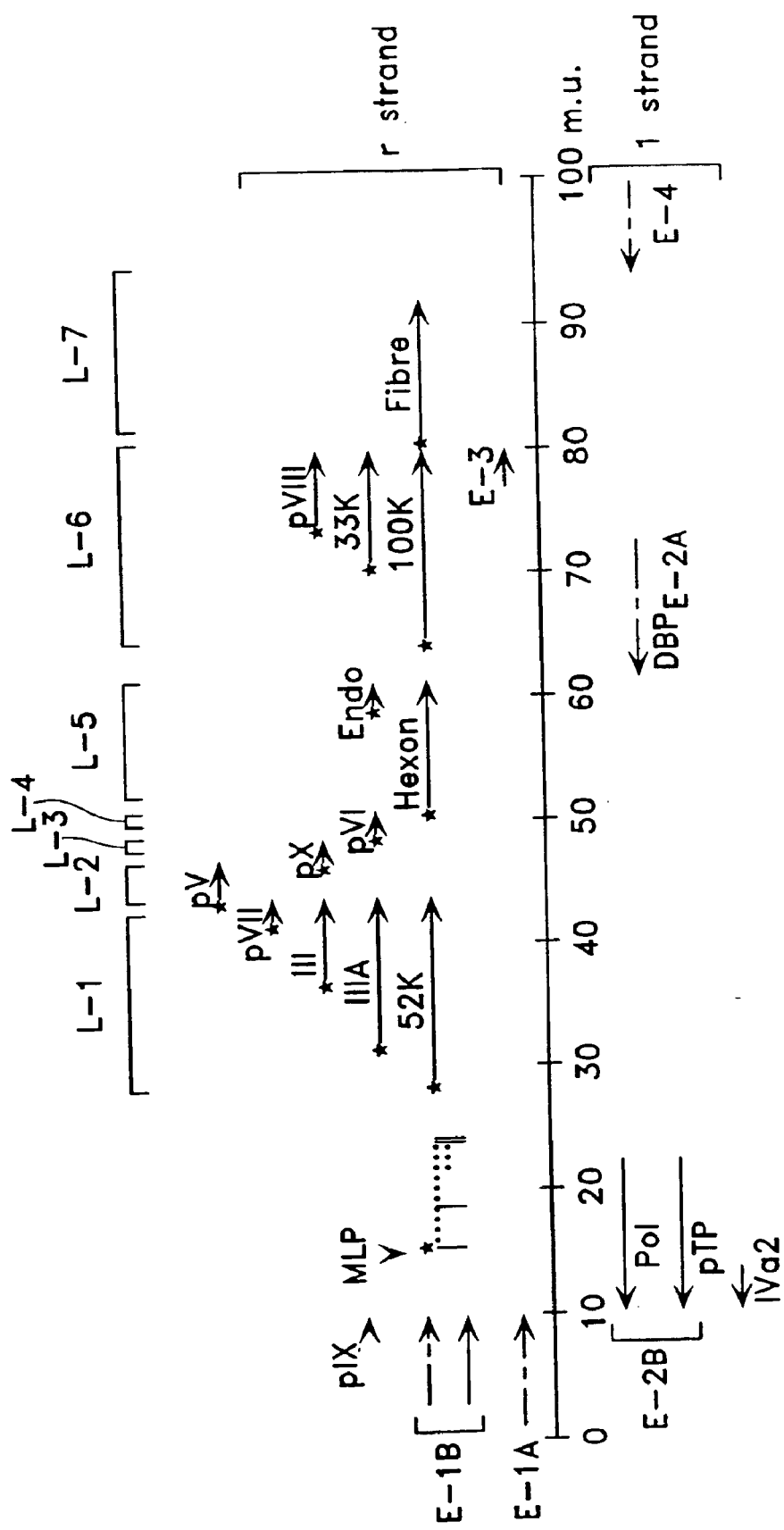
FIG. 2 shows a transcriptional map of the BAV3 genome, derived from transcriptional mapping of mRNAs and sequencing of cDNA clones.

We have discovered and constructed improved adenovirus vectors, in particular improved bovine adenovirus vectors, having altered tropism. The bovine adenovirus vectors of the present invention comprise a modification in a polynucleotide encoding at least one capsid protein, wherein the protein, or fragment thereof, is associated with tropism and wherein the modification is associated with altered tropism.

Capsid proteins include penton, hexon and fiber proteins. In one embodiment illustrated herein, a BAV3 adenovirus vector was constructed, BAV600, which comprised a replacement of the BAV3 fiber knob region with a human adenovirus (Ad5) fiber knob region. BAV600 demonstrated increased transduction in human cell lines as compared to a control adenovirus.

The present invention encompasses bovine adenovirus vectors comprising a replacement of a capsid protein, or fragment thereof, with a heterologous mammalian capsid protein, or fragment thereof, as long as the protein is associated with tropism and the replacement is associated with altered tropism. For example, in one embodiment, a bovine knob domain of a fiber protein is replaced with a porcine or ovine knob region of a fiber protein in order to alter species tropism. Such a bovine adenovirus vector can be used as an immunogen to boost immunity in a porcine or ovine mammal that has been primed with a porcine or ovine adenovirus, respectively. In such an immunization protocol, a boost immunization is achieved by administration of the bovine adenovirus having species specificity for the porcine or ovine mammal, while avoiding the affect of any neutralizing antibodies against the porcine or ovine mammal produced as a result of the priming immunization.

Alternatively, in another embodiment, a bovine fiber protein, or fragment thereof, such as the knob region, is replaced with a heterologous bovine fiber protein, or fragment thereof, such as a knob region of a fiber protein in order to alter bovine cell specificity. For one example, a bovine adenovirus sub-type 1 fiber region, or fragment thereof, such as a knob domain, is replaced with a bovine adenovirus sub-type 2 fiber region, or fragment thereof, such as a knob domain, in order to alter bovine cell-type specificity. Such a bovine adenovirus vector can be used as an immunogen to target specific cells or tissues.

The invention also encompasses the use of a bovine adenovirus comprising a replacement of a bovine capsid protein, or fragment thereof, with a human adenovirus capsid protein, or fragment thereof, such that the modified bovine adenovirus has species specificity for humans. Such bovine adenoviruses can be used in human immunization protocols, where preexisting neutralizing antibodies against human adenovirus-5 (HAV-5) in clinical patients may present an obstacle for efficient use of HAV-5.

Additionally, to provide a therapeutic effect to target cells, one or more heterologous therapeutic proteins may be present in the adenovirus vector.

Definitions

In describing the present invention, the following terminology, as defined below, will be used.

An "adenovirus vector" or "adenoviral vector" (used interchangeably) comprises a polynucleotide construct of the invention. A polynucleotide construct of this invention may be in any of several forms, including, but not limited to, DNA, DNA encapsulated in an adenovirus coat, DNA packaged in another viral or viral-like form (such as herpes simplex, and AAV), DNA encapsulated in liposomes, DNA complexed with polylysine, complexed with synthetic polycationic molecules, conjugated with transferrin, and complexed with compounds such as PEG to immunologically "mask" the molecule and/or increase half-life, and conjugated to a nonviral protein. Preferably, the polynucleotide is DNA. As used herein, "DNA" includes not only bases A, T, C, and G, but also includes any of their analogs or modified forms of these bases, such as methylated nucleotides, internucleotide modifications such as uncharged linkages and thioates, use of sugar analogs, and modified and/or alternative backbone structures, such as polyamides Adenovirus vectors may be replication-competent or replication-defective in a target cell.

As used herein, the term "altered tropism" refers to changing the specificity of an adenovirus. The term "altered tropism" encompasses changing species specificity as well as changing tissue or cell specificity of an adenovirus. In embodiments illustrated herein, species specificity is altered by producing modifications in a capsid protein(s), or fragment thereof, such as the fiber protein, and in particular the knob region of a fiber protein.

A "capsid protein" as used herein includes penton, hexon and fiber regions of an adenovirus. A capsid protein is associated with tropism if it directly or indirectly affects adenovirus tropism. A "modification of a capsid protein associated with altered tropism" as used herein refers to producing an alteration of a polynucleotide encoding a capsid protein, ie, a penton, hexon or fiber protein region, or fragment thereof, such as the knob domain of the fiber region such that specificity is altered. "Associated with" means that the modification contributes to the altered tropism either directly or indirectly. In embodiments illustrated herein, the modification is a replacement of bovine capsid protein regions with a heterologous mammalian capsid protein region in order to produce species specificity in the adenovirus. Replacement of one species capsid protein region with a heterologous capsid protein region may also produce altered tissue or cell specificity.

A "replicon" is any genetic element (e.g., plasmid, chromosome, virus) that functions as an autonomous unit of DNA replication in vivo; i.e., is capable of replication under its own control.

As used herein, the term "vector" refers to a polynucleotide construct designed for transduction/transfection of one or more cell types. Vectors may be, for example, "cloning vectors" which are designed for isolation, propagation and replication of inserted nucleotides, "expression vectors" which are designed for expression of a nucleotide sequence in a host cell, or a "viral vector" which is designed to result in the production of a recombinant virus or virus-like particle, or "shuttle vectors", which comprise the attributes of more than one type of vector.

By "live virus" is meant, in contradistinction to "killed" virus, a virus which is capable of producing identical progeny in tissue culture and inoculated animals.

A "helper-free virus vector" is a vector that does not require a second virus or a cell line to supply something defective in the vector.

A "double-stranded DNA molecule" refers to the polymeric form of deoxyribonucleotides (adenine, guanine, thymine, or cytosine) in its normal, double-stranded helix. This term refers only to the primary and secondary structure of the molecule, and does not limit it to any particular tertiary forms. Thus, this term includes double-stranded DNA found, inter alia, in linear DNA molecules (e.g., restriction fragments of DNA from viruses, plasmids, and chromosomes). In discussing the structure of particular double-stranded DNA molecules, sequences may be described herein according to the normal convention of giving only the sequence in the 5' to 3' direction along the nontranscribed strand of DNA (i.e., the strand having the sequence homologous to the mRNA).

A DNA "coding sequence" is a DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, procaryotic sequences, cDNA from eucaryotic mRNA, genomic DNA sequences from eucaryotic (e.g., mammalian) DNA, viral DNA, and even synthetic DNA sequences. A polyadenylation signal and transcription termination sequence will usually be located 3' to the coding sequence.

A "transcriptional promoter sequence" is a DNA regulatory region capable of binding RNA polymerase in a cell and initiating transcription of a downstream (3' direction) coding sequence. For purposes of defining the present invention, the promoter sequence is bound at the 3' terminus by the translation start codon (ATG) of a coding sequence and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eucaryotic promoters will often, but not always, contain "TATA" boxes and "CAAT" boxes. Procaryotic promoters contain Shine-Dalgarno sequences in addition to the −10 and −35 consensus sequences.

DNA "control sequences" refer collectively to promoter sequences, ribosome binding sites, splicing signals, polyadenylation signals, transcription termination sequences, upstream regulatory domains, enhancers, translational termination sequences and the like, which collectively provide for the transcription and translation of a coding sequence in a host cell.

A coding sequence or sequence encoding a protein is "operably linked to" or "under the control of" control sequences in a cell when RNA polymerase will bind the promoter sequence and transcribe the coding sequence into mRNA, which is then translated into the polypeptide encoded by the coding sequence.

A "host cell" is a cell which has been transformed, or is capable of transformation, by an exogenous DNA sequence.

A cell has been "transformed" by exogenous DNA when such exogenous DNA has been introduced inside the cell membrane. Exogenous DNA may or may not be integrated (covalently linked) to chromosomal DNA making up the genome of the cell. In procaryotes and yeasts, for example, the exogenous DNA may be maintained on an episomal element, such as a plasmid. A stably transformed cell is one in which the exogenous DNA has become integrated into the chromosome so that it is inherited by daughter cells through chromosome replication. For mammalian cells, this stability is demonstrated by the ability of the cell to establish cell lines or clones comprised of a population of daughter cell containing the exogenous DNA.

A "clone" is a population of daughter cells derived from a single cell or common ancestor. A "cell line" is a clone of a primary cell that is capable of stable growth in vitro for many generations.

A "heterologous" region of a DNA construct is an identifiable segment of DNA within or attached to another DNA molecule that is not found in association with the other molecule in nature. Thus, when the heterologous region encodes a viral gene, the gene will usually be flanked by DNA that does not flank the viral gene in the genome of the source virus or virus-infected cells. Another example of the heterologous coding sequence is a construct wherein the coding sequence itself is not found in nature (e.g., synthetic sequences having codons different from the native gene). Allelic variation or naturally occurring mutational events do not give rise to a heterologous region of DNA, as used herein As used herein in describing adenovirus vectors, "heterologous mammalian capsid region" means that the capsid region is obtainable from another mammalian species of adenovirus or is obtainable from the same species mammal but from a different type or sub-type adenovirus. For example "heterologous mammalian capsid protein" encompasses replacement of one sub-type bovine adenovirus capsid protein with another sub-type bovine adenovirus capsid protein as well as replacement of a bovine adenovirus capsid protein with another species capsid protein, such as a human capsid protein, as well as replacement of bovine adenovirus capsid proteins regions with another serotype bovine adenovirus capsid protein.

"Bovine host" refers to cattle of any breed, adult or infant.

The term "protein" is used herein to designate a polypeptide or glycosylated polypeptide, respectively, unless otherwise noted. The term "polypeptide" is used in its broadest sense, i.e., any polymer of amino acids (dipeptide or greater) linked through peptide bonds. Thus, the term "polypeptide" includes proteins, oligopeptides, protein fragments, analogs, muteins, fusion proteins and the like.

"Native" proteins or polypeptides refer to proteins or polypeptides recovered from adenovirus or adenovirus-infected cells. Thus, the term "native BAV polypeptide" would include naturally occurring BAV proteins and fragments thereof. "Non-native" polypeptides refer to polypeptides that have been produced by recombinant DNA methods or by direct synthesis. "Recombinant" polypeptides refers to polypeptides produced by recombinant DNA techniques; i.e., produced from cells transformed by an exogenous DNA construct encoding the desired polypeptide.

A "substantially pure" protein will be free of other proteins, preferably at least 10% homogeneous, more preferably 60% homogeneous, and most preferably 95% homogeneous.

An "antigen" refers to a molecule containing one or more epitopes that will stimulate a host's immune system to make a humoral and/or cellular antigen-specific response. The term is also used interchangeably with "immunogen."

A "hapten" is a molecule containing one or more epitopes that does not stimulate a host's immune system to make a humoral or cellular response unless linked to a carrier.

The term "epitope" refers to the site on an antigen or hapten to which a specific antibody molecule binds or is recognized by T cells. The term is also used interchangeably with "antigenic determinant" or "antigenic determinant site."

An "immunological response" to a composition or vaccine is the development in the host of a cellular and/or antibody-mediated immune response to the composition or vaccine of interest. Usually, such a response consists of the subject producing antibodies, B cells, helper T cells, suppressor T cells, and/or cytotoxic T cells directed specifically to an antigen or antigens included in the composition or vaccine of interest.

The terms "immunogenic polypeptide" and "immunogenic amino acid sequence" and "immunogen" refer to a polypeptide or amino acid sequence, respectively, which elicit antibodies that neutralize viral infectivity, and/or mediate antibody-complement or antibody-dependent cell cytotoxicity to provide protection of an immunized host. An "immunogenic polypeptide" as used herein, includes the full length (or near full length) sequence of the desired protein or an immunogenic fragment thereof.

By "immunogenic fragment" is meant a fragment of a polypeptide which includes one or more epitopes and thus elicits antibodies that neutralize viral infectivity, and/or mediates antibody-complement or antibody-dependent cell cytotoxicity to provide protection of an immunized host. Such fragments will usually be at least about 5 amino acids in length, and preferably at least about 10 to 15 amino acids in length There is no critical upper limit to the length of the fragment, which could comprise nearly the full length of the protein sequence, or even a fusion protein comprising fragments of two or more of the antigens. The term "treatment" as used herein refers to treatment of a mammal, such as bovine or human or other mammal, either (i) the prevention of infection or reinfection (prophylaxis), or (ii) the reduction or elimination of symptoms of an infection. The vaccine comprises the recombinant BAV itself or recombinant antigen produced by recombinant BAV.

By "infectious" is meant having the capacity to deliver the viral genome into cells.

The terms "polynucleotide" and "nucleic acid", used interchangeably herein, refer to a polymeric form of nucleotides of any length, either ribonucleotides or deoxyribonucleotides. These terms include a single-, double- or triple-stranded DNA, genomic DNA, cDNA, RNA, DNA-RNA hybrid, or a polymer comprising purine and pyrimidine bases, or other natural, chemically, biochemically modified, non-natural or derivatized nucleotide bases. The backbone of the polynucleotide can comprise sugars and phosphate groups (as may typically be found in RNA or DNA), or modified or substituted sugar or phosphate groups. Alternatively, the backbone of the polynucleotide can comprise a polymer of synthetic subunits such as phosphoramidates and thus can be a oligodeoxynucleoside phosphoramidate (P-NH2) or a mixed phosphoramidate-phosphodiester oligomer. Peyrottes et al. (1996) *Nucleic Acids Res.* 24: 1841–8; Chaturvedi et al. (1996) *Nucleic Acids Res.* 24: 2318–23; Schultz et al. (1996) *Nucleic Acids Res.* 24: 2966–73. A phosphorothioate linkage can be used in place of a phosphodiester linkage Braun et al. (1988) *J. Immunol.* 141: 2084–9; Latimer et al. (1995) *Molec. Immunol.* 32: 1057–1064. In addition, a double-stranded polynucleotide can be obtained from the single stranded polynucleotide product of chemical synthesis either by synthesizing the complementary strand and annealing the strands under appropriate conditions, or by synthesizing the complementary strand de novo using a DNA polymerase with an appropriate primer. Reference to a polynucleotide sequence (such as referring to a SEQ ID NO) also includes the complement sequence.

The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs, uracyl, other sugars and linking groups such as fluororibose and thioate, and nucleotide branches. The sequence of nucleotides may be interrupted by non-nucleotide components. A polynucleotide may be further modified after polymerization, such as by conjugation with a labeling component. Other types of modifications included in this definition are caps, substitution of one or more of the naturally occurring nucleotides with an analog, and introduction of means for attaching the polynucleotide to proteins, metal ions, labeling components, other polynucleotides, or a solid support. Preferably, the polynucleotide is DNA. As used herein, "DNA" includes not only bases A, T, C, and G, but also includes any of their analogs or modified forms of these bases, such as methylated nucleotides, internucleotide modifications such as uncharged linkages and thioates, use of sugar analogs, and modified and/or alternative backbone structures, such as polyamides.

A polynucleotide or polynucleotide region has a certain percentage (for example, 80%, 85%, 90%, or 95%) of "sequence identity" to another sequence means that, when aligned, that percentage of bases are the same in comparing the two sequences. This alignment and the percent homology or sequence identity can be determined using software programs known in the art, for example those described in *Current Protocols in Molecular Biology* (F. M. Ausubel et al., eds., 1987) Supplement 30, section 7.7.18, Table 7.7.1. A preferred alignment program is ALIGN Plus (Scientific and Educational Software, Pennsylvania), preferably using default parameters, which are as follows: mismatch=2; open gap=0; extend gap=2.

"Under transcriptional control" is a term well understood in the art and indicates that transcription of a polynucleotide sequence, usually a DNA sequence, depends on its being operably (operatively) linked to an element which contributes to the initiation of, or promotes, transcription. "Operably linked" refers to a juxtaposition wherein the elements are in an arrangement allowing them to function As used herein, "cytotoxicity" is a term well understood in the art and refers to a state in which a cell's usual biochemical or biological activities are compromised (i.e., inhibited). These activities include, but are not limited to, metabolism; cellular replication; DNA replication; transcription; translation; uptake of molecules. "Cytotoxicity" includes cell death and/or cytolysis. Assays are known in the art which indicate cytotoxicity, such as dye exclusion, $^3$H-thymidine uptake, and plaque assays.

In the context of adenovirus, a "heterologous polynucleotide" or "heterologous gene" or "transgene" is any polynucleotide or gene that is not present in wild-type adenovirus. Preferably, the transgene will also not be expressed or present in the target cell prior to introduction by the adenovirus vector.

In the context of adenovirus, a "heterologous" promoter or enhancer is one which is not associated with or derived from an adenovirus gene.

In the context of adenovirus, an "endogenous" promoter, enhancer, or control region is native to or derived from adenovirus.

A "host cell" includes an individual cell or cell culture which can be or has been a recipient of an adenoviral vector(s) of this invention. Host cells include progeny of a single host cell, and the progeny may not necessarily be completely identical (in morphology or in total DNA complement) to the original parent cell due to natural, accidental, or deliberate mutation and/or change. A host cell includes cells transfected or infected in vivo or in vitro with an adenoviral vector of this invention.

"Replication" and "propagation" are used interchangeably and refer to the ability of an adenovirus vector of the invention to reproduce or proliferate. These terms are well understood in the art. For purposes of this invention, replication involves production of adenovirus proteins and is generally directed to reproduction of adenovirus. Replication can be measured using assays standard in the art and described herein, such as a burst assay or plaque assay. "Replication" and "propagation" include any activity directly or indirectly involved in the process of virus manufacture, including, but not limited to, viral gene expression; production of viral proteins, nucleic acids or other components; packaging of viral components into complete viruses; and cell lysis.

A polynucleotide sequence that is "depicted in" a SEQ ID NO means that the sequence is present as an identical contiguous sequence in the SEQ ID NO. The term encompasses portions, or regions of the SEQ ID NO as well as the entire sequence contained within the SEQ ID NO.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom, and the progeny thereof. The definition also includes samples that have been manipulated in any way after their procurement, such as by treatment with reagents, solubilization, or enrichment for certain components, such as proteins or polynucleotides. The term "biological sample" encompasses a clinical sample, and also includes cells in culture, cell supernatants, cell lysates, serum, plasma, biological fluid, and tissue samples.

An "individual" or "mammalian subject" is a vertebrate, preferably a mammal, more preferably a human. Mammals include, but are not limited to, farm animals, sport animals, rodents, primates, and pets.

An "effective amount" is an amount sufficient to effect beneficial or desired results, including clinical results. An effective amount can be administered in one or more administrations. For purposes of this invention, an effective amount of an adenoviral vector is an amount that is sufficient to palliate, ameliorate, stabilize, reverse, slow or delay the progression of the disease state.

"Expression" includes transcription and/or translation.

As used herein, the term "comprising" and its cognates are used in their inclusive sense; that is, equivalent to the term "including" and its corresponding cognates.

"A," "an" and "the" include plural references unless the context clearly dictates otherwise.

DETAILED DESCRIPTION

The present invention identifies capsid proteins associated with tropism and provides methods of constructing adenovirus vectors and recombinant adenoviruses having altered tropism. In preferred embodiments, the adenovirus is a bovine adenovirus, such as a sub-type 1 adenovirus, in particular BAV3, or a sub-type 2 adenovirus. In illustrative embodiments, part or all of a bovine capsid protein encoding polynucleotide sequence associated with tropism is deleted and replaced with part or all of a heterologous mammalian capsid protein encoding polynucleotide sequence which alters adenovirus tropism. In a particular embodiment disclosed herein, the knob region of a bovine fiber protein is replaced with a human knob region of a fiber protein. The present invention also encompasses adenoviruses comprising the replacement of one bovine serotype adenovirus capsid protein associated with tropism with a heterologous bovine serotype adenovirus capsid protein associated with tropism in order to alter cell specificity.

The complete nucleotide sequence of the BAV3 genome is disclosed herein. See FIG. 1 (SEQ ID NO 1). A transcriptional map of the BAV3 genome, derived from transcriptional mapping of mRNAs and sequencing of cDNA clones, is presented in FIG. 2. Although the size (34,446 bp) and the overall organization of the BAV3 genome appear to be similar to that of HAVs, there are certain differences. Reddy et al. (1998) supra. One of the distinctive features of the BAV3 genome is the relatively small size of the E3 coding region (1517 bp). Mittal et al. (1992) *J. Gen. Virol.* 73:3295–3300; Mittal et al. (1993). *J. Gen. Virol.* 74:2825; and Reddy et al. (1998) supra. Analysis of the sequence of the BAV3 E3 region and its RNA transcripts suggests that BAV3 E3 may encode at least four proteins, one of which (121R) exhibits limited homology with the 14.7 kDa protein of HAV5. Idamakanti (1998) "Molecular characterization of E3 region of bovine adenovirus-3," M.Sc. thesis, University of Saskatchewan, Saskatoon, Saskatchewan.

Figure 4:
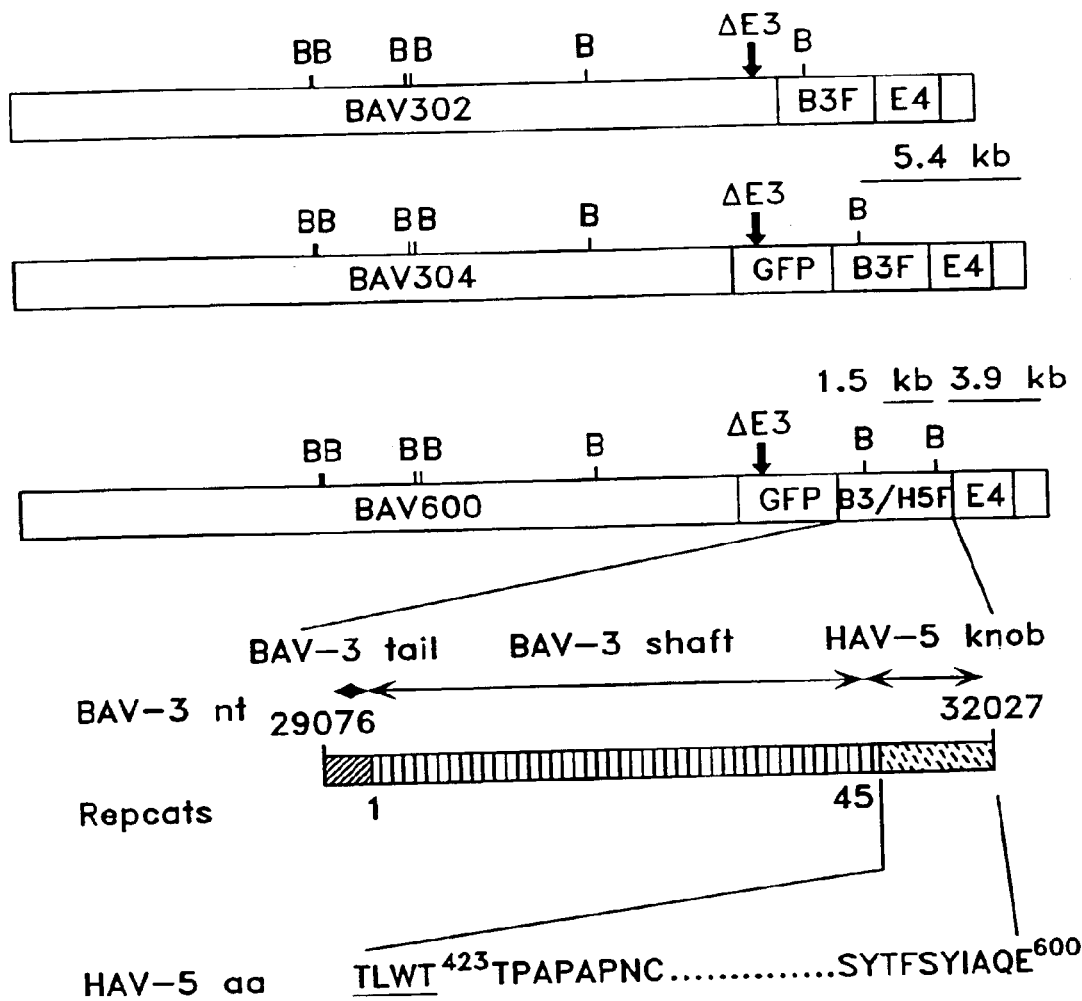
FIG. 4 illustrates the characterization of BAV600 (SEQ ID NO: 2–4).

Reddy et al. (1998) *Journal oj Viroiogy* 72:1394)disclose nucleotide sequences for BAV3. In the polynucleotide sequence for BAV3, the penton regions starts at 12919 and ends at 14367; the hexon region starts at 17809 and ends at 20517; the fiber region starts at 27968 and ends at 30898. The knob region (or domain) of the fiber protein starts after the residues TLWT motif as shown in FIG. 4 (SEQ ID NO: 2–4). The fiber protein also contains shaft and tail regions (or domains).

Human adenoviruses Ad3, Ad4, Ad5, Ad9 and Ad35 are available from the American Tissue Culture Collection ATCC). The National Center for Biotechnology Information GenBank accession number for Ad5 is M73260/M29978; for Ad9 X74659; and for Ad35, U10272. Chow et al. (1977, *Cell* 12:1–8) disclose human adenovirus 2 sequences; Davison et al. (1993, *J. Mole. Biol.* 234:1308–1316) disclose the DNA sequence of human adenovirus type 40; Sprengel et al. (1994, *J. Virol.* 68:379–389) disclose the DNA sequence for human adenovirus type 12 DNA; Vrati et al. (1995, *Virology,* 209:400–408) disclose sequences for ovine adenovirus; Morrison et al. (1997, *J. Gen. Virol.* 78:873–878) disclose canine adenovirus type 1 DNA sequence; and Reddy et al. (1998, *Virology,* 251:414) disclose DNA sequences for porcine adenovirus.

Shayakhmetov et al., supra, provide PCR primers for human Ad9 and human Ad35 fiber regions. The HAV-5 fiber protein is depicted in FIG. 12 (SEQ ID NO: 5); FIG. 13 (SEQ ID NO: 6) depicts the amino acid sequence for the Bovine Adenovirus-3 (BAV-3) fiber protein; FIG. 14 (SEQ ID NO: 7) depicts the amino acid sequence of Ovine Adenovirus 287 fiber protein; FIG. 15 (SEQ ID NO: 8) depicts the amino acid sequence of Porcine Adenovirus-3 (PAV-3)fiber protein; FIG. 16 (SEQ ID NO: 9) depicts the amino acid sequence of Canine Adenovirus-2 (CAV-2) fiber protein; and FIGS. 17A–17G (SEQ ID NO: 5–9) depicts an amino acid alignment of mammalian adenovirus fiber regions using the clustal method of the multialign program.

The knob domain of the fiber regions typically starts after the amino acid residue motif TLWT (hinge region), see FIG. 4 (SEQ ID NO: 2–4) (one exception is the ovine adenovirus fiber region).

Adenovirus vector constructs can then undergo recombination in vitro or in vivo, with a BAV genome either before or after transformation or transfection of an appropriate host cell.

Suitable host cells include any cell that will support recombination between a BAV genome and a plasmid containing BAV sequences, or between two or more plasmids, each containing BAV sequences. Recombination is generally performed in procaryotic cells, such as E. Coli, while transfection of a plasmid containing a viral genome, to generate virus particles, is conducted in eukaryotic cells, preferably mammalian cells, more preferably bovine cell cultures, most preferably MDBK or PFBR cells, and their equivalents. The growth of bacterial cell cultures, as well as culture and maintenance of eukaryotic cells and mammalian cell lines are procedures which are well-known to those of skill in the art.

One or more heterologous polynucleotide sequences can be inserted into one or more regions of the BAV genome to generate a recombinant BAV, limited only by the insertion capacity of the BAV genome and ability of the recombinant BAV to express the inserted heterologous sequences. In general, adenovirus genomes can accept inserts of approximately 5% of genome length and remain capable of being packaged into virus particles. The insertion capacity can be increased by deletion of non-essential regions and/or deletion of essential regions, such as, for example, E1 function, whose function is provided by a helper cell line, such as one providing E1 function. In some embodiments, a heterologous polynucleotide encoding a protein is inserted into an adenovirus E1 gene region. In some embodiments, an adenovirus has a deletion of part or all of the E1 gene region and is propagated in a helper cell line providing E1 function. In yet other embodiments, a heterologous polynucleotide encoding a protein is inserted into an adenovirus E3 gene region. In other embodiments, an adenovirus has a deletion of part or all of the E3 region.

In one embodiment of the invention, insertion can be achieved by constructing a plasmid containing the region of the BAV genome into which insertion is desired, such as a polynucleotide encoding a capsid protein. Additionally, a polynucleotide encoding a desired therapeutic protein can be inserted into the bovine adenovirus. The plasmid is then digested with a restriction enzyme having a recognition sequence in the BAV portion of the plasmid, and a heterologous polynucleotide sequence is inserted at the site of restriction digestion. The plasmid, containing a portion of the BAV genome with an inserted heterologous sequence, is co-transformed, along with a BAV genome or a linearized plasmid containing a BAV genome, into a bacterial cell (such as, for example, E. coli), wherein the BAV genome can be a full-length genome or can contain one or more deletions. Homologous recombination between the plasmids generates a recombinant BAV genome containing inserted heterologous sequences.

Deletion of BAV sequences, to provide a site for insertion of heterologous sequences or to provide additional capacity for insertion at a different site, can be accomplished by methods well-known to those of skill in the art. For example, for BAV sequences cloned in a plasmid, digestion with one or more restriction enzymes (with at least one recognition sequence in the BAV insert) followed by ligation will, in some cases, result in deletion of sequences between the restriction enzyme recognition sites. Alternatively, digestion at a single restriction enzyme recognition site within the BAV insert, followed by exonuclease treatment, followed by ligation will result in deletion of BAV sequences adjacent to the restriction site. A plasmid containing one or more portions of the BAV genome with one or more deletions, constructed as described above, can be co-transfected into a bacterial cell along with a BAV genome (full-length or deleted) or a plasmid containing either a full-length or a deleted BAV genome to generate, by homologous recombination, a plasmid containing a recombinant BAV genome with a deletion at one or more specific sites. BAV virions containing the deletion can then be obtained by transfection of mammalian cells (including, but not limited to, MDBK or PFBR cells and their equivalents) with the plasmid containing the recombinant BAV genome.

In one embodiment of the invention, insertion sites are adjacent to and downstream (in the transcriptional sense) of BAV promoters. Locations of BAV promoters, and restriction enzyme recognition sequences downstream of BAV promoters, for use as insertion sites, can be easily determined by one of skill in the art from the BAV nucleotide sequence provided herein. Alternatively, various in vitro techniques can be used for insertion of a restriction enzyme recognition sequence at a particular site, or for insertion of heterologous sequences at a site that does not contain a restriction enzyme recognition sequence. Such methods include, but are not limited to, oligonucleotide-mediated heteroduplex formation for insertion of one or more restriction enzyme recognition sequences (see, for example, Zoller et al. (1982) *Nucleic Acids Res.* 10:6487–6500; Brennan et al. (1990) *Roux's Arch. Dev. Biol.* 199:89–96; and Kunkel et al. (1987) *Meth. Enzymology* 154:367–382) and PCR-mediated methods for insertion of longer sequences. See, for example, Zheng et al. (1994) *Virus Research* 31:163–186.

It is also possible to obtain expression of a heterologous sequence inserted at a site that is not downstream from a BAV promoter, if the heterologous sequence additionally comprises transcriptional regulatory sequences that are active in eukaryotic cells. Such transcriptional regulatory sequences can include cellular promoters such as, for example, the bovine hsp70 promoter and viral promoters such as, for example, herpesvirus, adenovirus and papovavirus promoters and DNA copies of retroviral long terminal repeat (LTR) sequences.

In another embodiment, homologous recombination in a procaryotic cell can be used to generate a cloned BAV genome; and the cloned BAV genome can be propagated as a plasmid. See for example, U.S. Pat. No. 5,922,576. Infectious virus can be obtained by transfection of mammalian cells with the cloned BAV genome rescued from plasmid-containing cells.

The invention also provides BAV regulatory sequences which can be used to regulate the expression of heterologous genes. A regulatory sequence can be, for example, a transcriptional regulatory sequence, a promoter, an enhancer, an upstream regulatory domain, a splicing signal, a polyadenylation signal, a transcriptional termination sequence, a translational regulatory sequence, a ribosome binding site and a translational termination sequence.

In another embodiment, the cloned BAV genome can be propagated as a plasmid and infectious virus can be rescued from plasmid-containing cells.

The presence of viral nucleic acids can be detected by techniques known to one of skill in the art including, but not limited to, hybridization assays, polymerase chain reaction, and other types of amplification reactions. Similarly, methods for detection of proteins are well-known to those of skill in the art and include, but are not limited to, various types of immunoassay, ELISA, Western blotting, enzymatic assay, immunohistochemistry, etc. Diagnostic kits comprising the nucleotide sequences of the invention may also contain reagents for cell disruption and nucleic acid purification, as well as buffers and solvents for the formation, selection and detection of hybrids. Diagnostic kits comprising the polypeptides or amino acid sequences of the invention may also comprise reagents for protein isolation and for the formation, isolation, purification and/or detection of immune complexes.

Various foreign genes or nucleotide sequences or coding sequences (prokaryotic, and eukaryotic) can be inserted in the bovine adenovirus nucleotide sequence, e.g., DNA, in accordance with the present invention, particularly to provide protection against a wide range of diseases and many such genes are already known in the art. The problem heretofore has been to provide a safe, convenient and effective vaccine vector for the genes or sequences, as well as safe, effective means for gene transfer to be used in various gene therapy applications.

An exogenous (i.e., foreign) nucleotide sequence can consist of one or more gene(s) of interest, and preferably of therapeutic interest. In the context of the present invention, a gene of interest can code either for an antisense RNA, a ribozyme or for an mRNA which will then be translated into a protein of interest. A gene of interest can be of genomic type, of complementary DNA (cDNA) type or of mixed type (minigene, in which at least one intron is deleted). It can code for a mature protein, a precursor of a mature protein, in particular a precursor intended to he secreted and accordingly comprising a signal peptide, a chimeric protein originating from the fusion of sequences of diverse origins, or a mutant of a natural protein displaying improved or modified biological properties. Such a mutant may be obtained by, deletion, substitution and/or addition of one or more nucleotide(s) of the gene coding for the natural protein, or any other type of change in the sequence encoding the natural protein, such as, for example, transposition or inversion.

A gene of interest may be placed under the control of elements (DNA control sequences) suitable for its expression in a host cell. Suitable DNA control sequences are understood to mean the set of elements needed for transcription of a gene into RNA (antisense RNA or mRNA) and for the translation of an mRNA into protein. Among the elements needed for transcription, the promoter assumes special importance. It can be a constitutive promoter or a regulatable promoter, and can he isolated from any gene of eukaryotic, prokaryotic or viral origin, and even adenoviral origin. Alternatively, it can be the natural promoter of the gene of interest. Generally speaking, a promoter used in the present invention may be modified so as to contain regulatory sequences. As examples, a gene of interest in use in the present invention is placed under the control of the promoter of the immunoglobulin genes when it is desired to target its transfer to lymphocytic host cells. There may also be mentioned the HSV-1 TK (herpesvirus type 1 thymidine kinase) gene promoter, the adenoviral MLP (major late promoter), in particular of human adenovirus type 2, the RSV (Rous Sarcoma Virus) LTR (long terminal repeat), the CMV (Cytomegalovirus) early promoter, and the PGK (phosphoglycerate kinase) gene promoter, for example, permitting expression in a large number of cell types.

As disclosed herein altering species tropism is demonstrated in BAV by replacement of the native fiber protein region with a heterologous mammalian fiber protein region. The present invention also encompasses replacement of one bovine serotype adenovirus fiber region with another bovine serotype adenovirus fiber region wherein said replacement is associated with altered bovine cell specificity. Alternatively, targeting of a recombinant BAV vector to a particular cell type can be achieved by constructing recombinant hexon and/or fiber genes The protein products of these genes are involved in host cell recognition; therefore, the genes can be modified to contain peptide sequences that will allow the virus to recognize alternative host cells.

Among genes of interest which are useable in the context of the present invention, there may be mentioned:

genes coding for cytokines such as interferons and interleukins;

genes encoding lymphokines;

genes coding for membrane receptors such as the receptors recognized by pathogenic organisms (viruses, bacteria or parasites), preferably by the HIV virus (human immunodeficiency virus);

genes coding for coagulation factors such as factor VIII and factor IX;

genes coding for dystrophins;

genes coding for insulin;

genes coding for proteins participating directly or indirectly in cellular ion channels, such as the CFTR (cystic fibrosis transmembrane conductance regulator) protein;

genes coding for antisense RNAs, or proteins capable of inhibiting the activity of a protein produced by a pathogenic gene which is present in the genome of a pathogenic organism, or proteins (or genes encoding them) capable of inhibiting the activity of a cellular gene whose expression is deregulated, for example an oncogene;

genes coding for a protein inhibiting an enzyme activity, such as $\alpha_1$ antitrypsin or a viral protease inhibitor, for example;

genes coding for variants of pathogenic proteins which have been mutated so as to impair their biological function, such as, for example, trans-dominant variants of the tat protein of the HIV virus which are capable of competing with the natural protein for binding to the target sequence, thereby preventing the activation of HIV;

genes coding for antigenic epitopes in order to increase the host cell's immunity;

genes coding for major histocompatibility complex classes I and II proteins, as well as the genes coding for the proteins which are inducers of these genes;

genes coding for antibodies;

genes coding for immunotoxins;

genes encoding toxins;

genes encoding growth factors or growth hormones;

genes encoding cell receptors and their ligands;

genes encoding tumor suppressors;

genes involved in cardiovascular disease including, but not limited to, oncogenes; genes encoding growth factors including, but not limited to, fibroblast growth factor (FGF), vascular endothelial growth factor (VEGF), and nerve growth factor (NGF); e-nos, tumor suppressor genes including, but not limited to, the Rb (retinoblastoma) gene; lipoprotein lipase; superoxide dismutase (SOD); catalase; oxygen and free radical scavengers; apolipoproteins; and pai-1 (plasminogen activator inhibitor-1);

genes coding for cellular enzymes or those produced by pathogenic organisms; and suicide genes. The HSV-1 TK suicide gene may be mentioned as an example. This viral TK enzyme displays markedly greater affinity compared to the cellular TK enzyme for certain nucleoside analogues (such as acyclovir or gancyclovir). It converts them to monophosphorylated molecules, which can themselves be converted by cellular enzymes to nucleotide precursors, which are toxic. These nucleotide analogues can be incorporated into replicating DNA molecules, hence incorporation occurs chiefly in the DNA of dividing cells. This incorporation can result in specific destruction of dividing cells such as cancer cells.

This list is not restrictive, and other genes of interest may be used in the context of the present invention.

It is also possible that only fragments of nucleotide sequences of genes can be used (where these are sufficient to generate a protective immune response or a specific biological effect) rather than the complete sequence as found in the wild-type organism. Where available, synthetic genes or fragments thereof can also be used. However, the present invention can be used with a wide variety of genes, fragments and the like, and is not limited to those set out above.

In some cases the gene for a particular antigen can contain a large number of introns or can be from an RNA virus, in these cases a complementary DNA copy (cDNA) can be used.

In order for successful expression of the gene to occur, it can be inserted into an expression vector together with a suitable promoter including enhancer elements and polyadenylation sequences. A number of eucaryotic promoter and polyadenylation sequences which provide successful expression of foreign genes in mammalian cells and construction of expression cassettes, are known in the art, for example in U.S. Pat. No. 5,151,267, the disclosures of which are incorporated herein by reference. The promoter is selected to give optimal expression of immunogenic protein which in turn satisfactorily leads to humoral, cell mediated and mucosal immune responses according to known criteria.

The foreign protein produced by expression in vivo in a recombinant virusinfected cell may be itself immunogenic. More than one foreign gene can be inserted into the viral genome to obtain successful production of more than one effective protein.

Thus with the recombinant viruses of the present invention, it is possible to provide protection against a wide variety of diseases affecting cattle, humans and other mammals. Any of the recombinant antigenic determinants or recombinant live viruses of the invention can be formulated and used in substantially the same manner as described for antigenic determinant vaccines or live vaccine vectors.

The present invention also includes pharmaceutical compositions comprising a therapeutically effective amount of a recombinant adenovirus vector, recombinant adenovirus or recombinant protein, prepared according to the methods of the invention, in combination with a pharmaceutically acceptable vehicle and/or an adjuvant. Such a pharmaceutical composition can be prepared and dosages determined according to techniques that are well-known in the art. The pharmaceutical compositions of the invention can be administered by any known administration route including, but not limited to, systemically (for example, intravenously, intratracheally, intravascularly, intrapulmonarilly, intraperitoneally, intranasally, parenterally, enterically, intramuscularly, subcutaneously, intratumorally or intracranially) or by aerosolization or intrapulmonary instillation. Administration can take place in a single dose or in doses repeated one or more times after certain time intervals. The appropriate administration route and dosage will vary in accordance with the situation (for example, the individual being treated, the disorder to be treated or the gene or polypeptide of interest), but can be determined by one of skill in the art.

The invention also encompasses a method of treatment, according to which a therapeutically effective amount of a BAV vector, recombinant BAV, or host cell of the invention is administered to a mammalian subject requiring treatment.

The antigens used in the present invention can be either native or recombinant antigenic polypeptides or fragments. They can be partial sequences, full-length sequences, or even fusions (e.g., having appropriate leader sequences for the recombinant host, or with an additional antigen sequence for another pathogen). The preferred antigenic polypeptide to be expressed by the virus systems of the present invention contain full-length (or near full-length) sequences encoding antigens. Alternatively, shorter sequences that are antigenic (i.e., encode one or more epitopes) can be used. The shorter sequence can encode a "neutralizing epitope," which is defined as an epitope capable of eliciting antibodies that neutralize virus infectivity in an in vitro assay. Preferably the peptide should encode a "protective epitope" that is capable of raising in the host a "protective immune response;" i.e., an antibody- and/or a cell-mediated immune response that protects an immunized host from infection.

The antigens used in the present invention, particularly when comprised of short oligopeptides, can be conjugated to a vaccine carrier. Vaccine carriers are well known in the art: for example, bovine serum albumin (BSA), human serum albumin (HSA) and keyhole limpet hemocyanin (KLH). A preferred carrier protein, rotavirus VP6, is disclosed in EPO Pub. No. 0259149, the disclosure of which is incorporated by reference herein.

Genes for desired antigens or coding sequences thereof which can be inserted include those of organisms which cause disease in mammals, particularly bovine pathogens such as bovine rotavirus, bovine coronavirus, bovine herpes virus type 1, bovine respiratory syncytial virus, bovine parainfluenza virus type 3 (BPI-3), bovine diarrhea virus, *Pasteurella haemolytica, Haemophilus somnus* and the like. Genes encoding antigens of human pathogens also useful in the practice of the invention. The vaccines of the invention carrying foreign genes or fragments can also be orally administered in a suitable oral carrier, such as in an enteric-coated dosage form. Oral formulations include such normally-employed excipients as, for example, pharmaceutical grades of mannitol, lactose, starch, magnesium stearate, sodium saccharin cellulose, magnesium carbonate, and the like. Oral vaccine compositions may be taken in the form of solutions, suspensions, tablets, pills, capsules, sustained release formulations, or powders, containing from about 10% to about 95% of the active ingredient, preferably about 25% to about 70%. Oral and/or intranasal vaccination may be preferable to raise mucosal immunity (which plays an important role in protection against pathogens infecting the respiratory and gastrointestinal tracts) in combination with systemic immunity.

In addition, the vaccine can be formulated into a suppository. For suppositories, the vaccine composition will include traditional binders and carriers, such as polyalkaline glycols or triglycerides. Such suppositories may be formed from mixtures containing the active ingredient in the range of about 0.5% to about 10% (w/w), preferably about 1% to about 2%

Protocols for administering to animals the vaccine composition(s) of the present invention are within the skill of the art in view of the present disclosure. Those skilled in the art will select a concentration of the vaccine composition in a dose effective to elicit an antibody and/or T-cell mediated immune response to the antigenic fragment. Within wide limits, the dosage is not believed to be critical. Typically, the vaccine composition is administered in a manner which will deliver between about 1 to about 1,000 micrograms of the subunit antigen in a convenient volume of vehicle, e.g., about 1–10 cc. Preferably, the dosage in a single immunization will deliver from about 1 to about 500 micrograms of subunit antigen, more preferably about 5–10 to about 100–200 micrograms (e.g., 5–200 micrograms).

The timing of administration may also be important. For example, a primary inoculation preferably may be followed by subsequent booster inoculations if needed. It may also be preferred, although optional, to administer a second, booster immunization to the animal several weeks to several months after the initial immunization. To insure sustained high levels of protection against disease, it may be helpful to readminister a booster immunization to the animals at regular intervals, for example once every several years. Alternatively, an initial dose may be administered orally followed by later inoculations, or vice versa. Preferred vaccination protocols can be established through routine vaccination protocol experiments.

The dosage for all routes of administration of in vivo recombinant virus vaccine depends on various factors including, the size of patient, nature of infection against which protection is needed, carrier and the like and can readily be determined by those of skill in the art. By way of non-limiting example, a dosage of between $10^3$ pfu and $10^{15}$ pfu, preferably between $10^5$ and $10^{13}$ pfu, more preferably between $10^6$ to $10^{11}$ pfu and the like can be used. As with in vitro subunit vaccines, additional dosages can be given as determined by the clinical factors involved.

In some embodiments of the invention, recombinant cell lines are produced by constructing an expression cassette comprising the BAV E1 region, and/or other essential gene region and transforming host cells therewith to provide complementing cell lines or cultures expressing the E1 proteins for use with replication-defective bovine adenoviruses modified to have altered tropism and lacking E1 function. These recombinant complementing cell lines are capable of allowing a defective recombinant BAV with deleted E1 sequences to replicate and express a desired foreign gene or fragment thereof which is optionally encoded within the recombinant BAV. These cell lines are also extremely useful in generating recombinant BAV, having an E3 gene deletion replaced by heterologous nucleotide sequence encoding for a foreign gene or fragment, by in vivo recombination following DNA-mediated cotransfection. More generally, defective recombinant BAV vectors, lacking one or more essential functions encoded by the BAV genome, can be propagated in appropriate complementing cell lines, wherein a particular complementing cell line provides a function or functions that is (are) lacking in a particular defective recombinant BAV vector. Complementing cell lines can provide viral functions through, for example, co-infection with a helper virus, or by integrating or otherwise maintaining in stable form a fragment of a viral genome encoding a particular viral function.

In one embodiment of the invention, the recombinant expression cassette can be obtained by cleaving a BAV genome with an appropriate restriction enzyme to produce a DNA fragment representing the left end or the right end of the genome comprising E1 or E3 gene region sequences, respectively and inserting the left or right end fragment into a cloning vehicle, such as a plasmid, and thereafter inserting at least one heterologous DNA sequence into the E1 or E3 deletion with or without the control of an exogenous promoter. The recombinant expression cassette is contacted with a BAV genome within an appropriate cell and, through homologous recombination or other conventional genetic engineering method, a recombinant BAV genome is obtained. Appropriate cells include both prokaryotic cells, such as, for example, E. coli, and eukaryotic cells. Examples of suitable eukaryotic cells include, but are not limited to, MDBK cells, MDBK cells expressing adenovirus E1 function, primary fetal bovine retina cells, and cells expressing functions that are equivalent to those of the previously-recited cells. Restriction fragments of the BAV genome other than those comprising the E1 or E3 regions are also useful in the practice of the invention and can be inserted into a cloning vehicle such that heterologous sequences may be inserted into non-E1 and E3 BAV sequences. These DNA constructs can then undergo recombination in vitro or in vivo, with a BAV genome, either before or after transformation or transfection of a suitable host cell as described above. For the purposes of the present invention, a BAV genome can be either a full-length genome or a genome containing a deletion in a region other than that deleted in the fragment with which it recombines, as long as the resulting recombinant BAV genome contains BAV sequences required for replication and packaging. Methods for transfection, cell culture and recombination in procaryotic and eukaryotic cells such as those described above are well-known to those of skill in the art.

In another embodiment of the invention, the function of any viral region which may be mutated or deleted in any particular viral vector can be supplied (to provide a complementing cell line) by co-infection of cells with a virus which expresses the function that the vector lacks.

If an insertion is made in a gene essential for viral replication, the adenovirus must be grown in an appropriate complementing cell line (i.e., a helper cell line). In human adenoviruses, certain open reading frames in the E4 region (ORF 3 and ORF 6/7) are essential for viral replication. Deletions in analogous open reading frames in the E4 region of BAV-3 could necessitate the use of a helper cell line for growth of the viral vector.

The BAV E1 gene products of the adenovirus of the invention transactivate most of the cellular genes, and therefore, cell lines which constitutively express E1 proteins can express cellular polypeptides at a higher level than normal cell lines. The recombinant mammalian, particularly bovine, cell lines of the invention can be used to prepare and isolate polypeptides, including those such as (a) proteins associated with adenovirus E1A proteins: e.g. p300, retinoblastoma (Rb) protein, cyclins, kinases and the like; (b) proteins associated with adenovirus E1B protein: e.g. p53 and the like; (c) growth factors, such as epidermal growth factor (EGF), transforming growth factor (TGF) and the like; (d) receptors such as epidermal growth factor receptor (EGF-R), fibroblast growth factor receptor (FGF-R), tumor necrosis factor receptor (TNF-R), insulin-like growth factor receptor (IGF-R), major histocompatibility complex class I receptor and the like; (e) proteins encoded by proto-oncogenes such as protein kinases (tyrosine-specific protein kinases and protein kinases specific for serine or threonine), p21 proteins (guanine nucleotide-binding proteins with GTPase activity) and the like; (f) other cellular proteins such as actins, collagens, fibronectins, integrins, phosphoproteins, proteoglycans, histones and the like, and (g) proteins involved in regulation of transcription such as TATA-box-binding protein (TBP), TBP-associated factors (TAFs), Sp1 binding protein and the like.

The invention also includes a method for providing gene delivery to a mammal, such as a bovine or a human or other mammal in need thereof, to control a gene deficiency, to provide a therapeutic gene or nucleotide sequence and/or to induce or correct a gene mutation. The method can be used, for example, in the treatment of conditions including, but not limited to hereditary disease, infectious disease, cardiovascular disease, and viral infection. The method comprises administering to said mammal a live recombinant bovine adenovirus comprising a modification in a capsid protein, or fragment thereof, wherein said capsid protein is associated with tropism and said modification is associated with altered tropism and wherein said adenovirus vector further comprises a foreign polynucleotide sequence encoding a non-defective form of said gene under conditions wherein the recombinant virus vector genome is incorporated into said mammalian genome or is maintained independently and extrachromosomally to provide expression of the required gene in the target organ or tissue These kinds of techniques are currently being used by those of skill in the art for the treatment of a variety of disease conditions, non-limiting examples of which are provided above. Examples of foreign genes, nucleotide sequences or portions thereof that can be incorporated for use in a conventional gene therapy include, cystic fibrosis transmembrane conductance regulator gene, human minidystrophin gene, alpha-1-antitrypsin gene, genes involved in cardiovascular disease, and the like.

In particular, the practice of the present invention in regard to gene delivery in humans is intended for the prevention or treatment of diseases including, but not limited to, genetic diseases (for example, hemophilia, thalassemias, emphysema, Gaucher's disease, cystic fibrosis, Duchenne muscular dystrophy, Duchenne's or Becker's myopathy, etc.), cancers, viral diseases (for example, AIDS, herpesvirus infection, cytomegalovirus infection and papillomavirus infection), cardiovascular diseases, and the like. For the purposes of the present invention, the vectors, cells and viral particles prepared by the methods of the invention may be introduced into a subject either ex vivo, (i.e., in a cell or cells removed from the patient) or directly in vivo into the body to be treated.

The following examples are provided to illustrate but not limit the invention.

EXAMPLES

Example 1

Construction of BAV600 Containing a Human Fiber Gene

Figure 3:
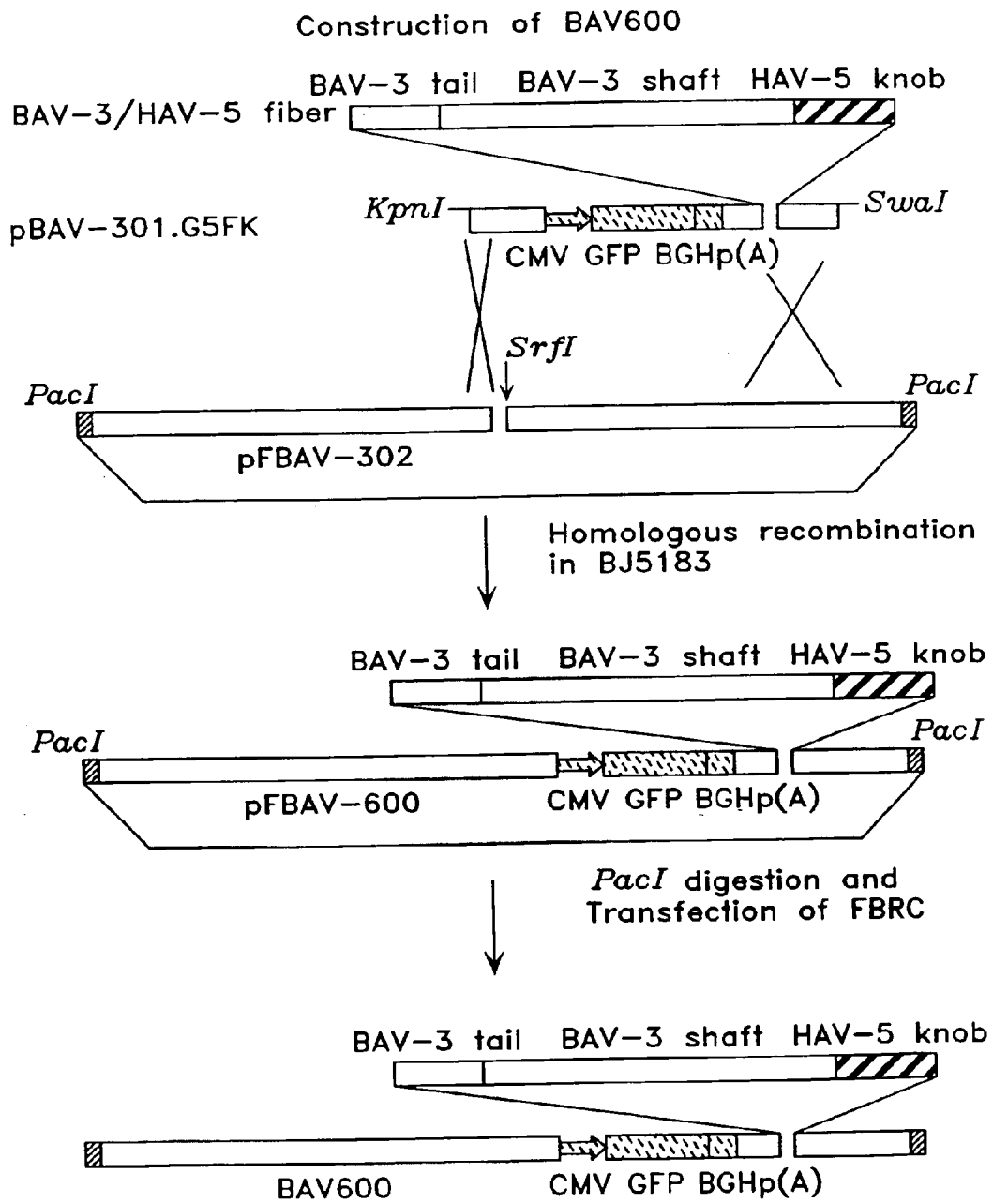
FIG. 3 illustrates the construction of BAV600 that expresses the HAV-5 fiber knob protein.

To generate an BAV-3 vector with an altered tropism, the chimeric fiber gene construct containing the HAV-5 fiber knob fused to the BAV-3 tail and shaft was incorporated into the BAV-3 genome of BAV304, described in Reddy et al., supra 1999 (FIG. 3). For the precise replacement of the wild-type BAV-3 fiber gene, a previously made plasmid pBAV301.gfp (Reddy et al., 1999) was used for modification of BAV-3 fiber. The resulting transfer vector pBAV-301.G5FK contained a CMV promoter driven green fluorescent protein (GFP) expression cassette inserted into the E3 region, the chimeric BAV-3/HAV-5 fiber gene, and E4. This transfer vector was used for incorporation of GFP cassette and modified fiber gene into the backbone of an E3 deleted BAV-3 infectious plasmid, p.FBAV302 (Zakhartchouk et al., 1998), via homologous recombination in E. coli BJ5183 (Chartier et al., 1996), creating plasmid pFBAV-600. The viral genome was released from the plasmid by PacI digestion and used to transfect cell line ATCC accession number PTA156, fetal bovine retinal cells expressing E1 protein (see Reddy et al. 1999, supra). The corresponding chimeric virus BAV600 was produced 21 days following transfection.

Example 2

Characterization of BAV600

BAV600 obtained from the transfection of fetal bovine retinal cells expressing E1 protein, ATCC accession number PTA156, was amplified in MDBK cells, and the viral DNA was extracted from infected cells. The DNA was analyzed after digestion with restriction enzyme Bg/II and agarose gel electrophoresis (FIG. 5A). As shown in FIGS. 5A–5B, both the parental BAV302 and BAV304 had Bg/II fragment of 5.4 kb at the right end of viral genome. The HAV-5 fiber knob region introduces an additional Bg/II restriction enzyme site within the BAV600 genome. Therefore, diagnostic 1.5 and 3.9 kb fragments were found after Bg/II digestion. Southern blot analysis with the HAV-5 fiber knob probe demonstrated the expected hybridization pattern for Bg/II-digested BAV600 (FIG. 5B).

Expression and assembly of the chimeric BAV-3 and HAV-5 fiber protein by recombinant BAV600 were examined by immunoprecipitation assay. Metabolically radiolabeled immunoprecipitates from the parental (BAV304; Reddy et al., 1999, supra) and chimeric (BAV600) viruses-infected MDBK cell lysates were subjected to SDS-PAGE under denaturing conditions. A wild-type HAV-5 containing a full-length fiber was also analyzed. Immunoprecipitation assay was carried out with a rabbit polyclonal antibody specific for the BAV3 fiber knob and an antifiber monoclonal antibody, ID6.14. The ID6.14 antibody recognizes a trimerized HAV-5 fiber knob and neutralizes HAV-5 through binding to knob domain (Douglas et al., 1996). As shown in FIG. 6, the BAV-3 and BAV304 viruses contain fiber proteins with sizes of approximately 100 kDa which react with the rabbit polyclonal antibody specific for the BAV3 fiber knob, while the HAV-5 contains a fiber protein with a size of approximately 64 kDa. The presence of the HAV-5 fiber knob within the BAV600 chimeric virus was confirmed by immunoprecipitation analysis with the monoclonal antibody ID6.14 specific for the HAV-5 knob.

The biological titer of the fiber chimeric virus BAV600 was compared with the BAV-3 and parental virus BAV304. Biological titers determined with MDBK cell monolayers indicated maximum plaque-forming titers of $10^8$, $10^6$, and $10^5$ PFU/ml for the BAV-3, BAV304, and BAV600, respectively. The result suggested that the fiber modification and GFP insertion in E3 region significantly alter the cellular production of the virus.

Example 3

Transduction of Human Cell Lines by BAV600

Figure 7A:
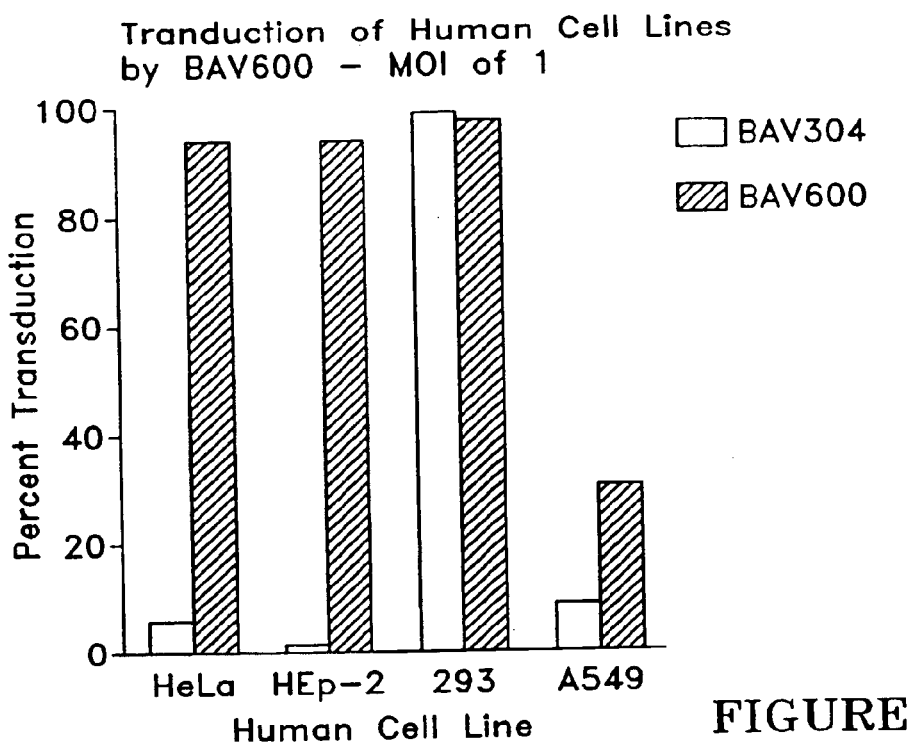
FIGS. 7A–7B show the transduction of Human cell lines by BAV600.
Figure 7B:
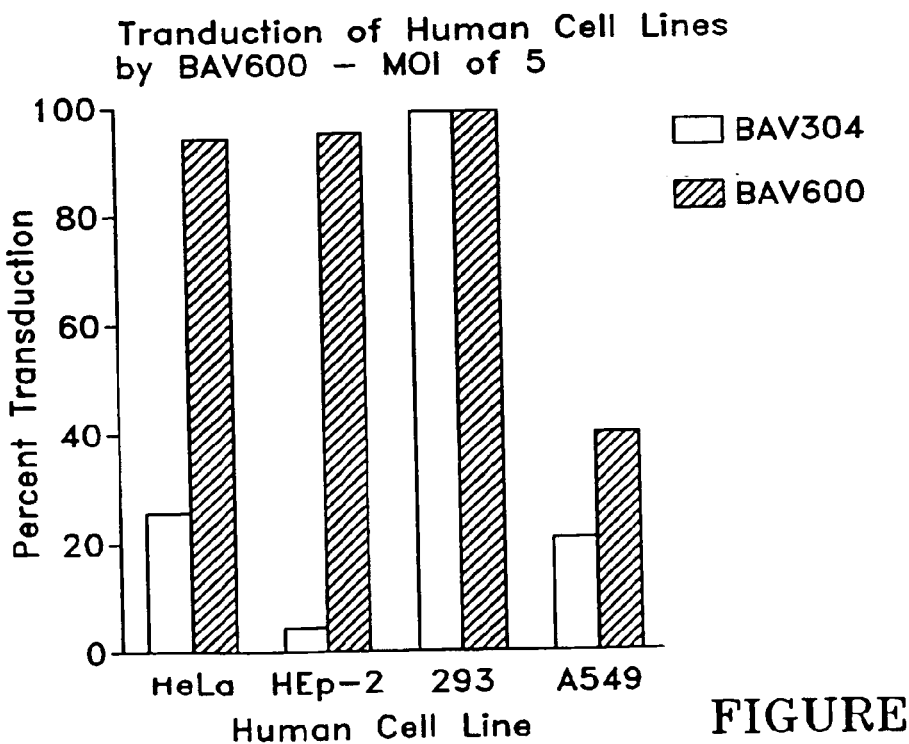
Figure 9:
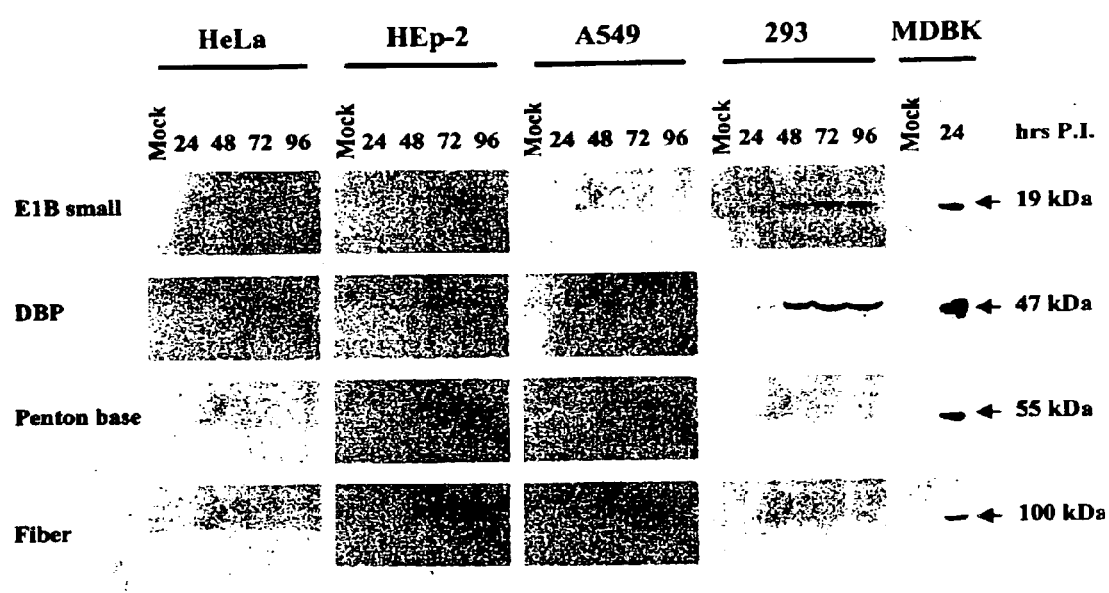
FIG. 9 shows the expression of early and late BAV-3 proteins in human cell lines, HeLa, HEp-2, A549, 293 and MDBK.
Figure 10:
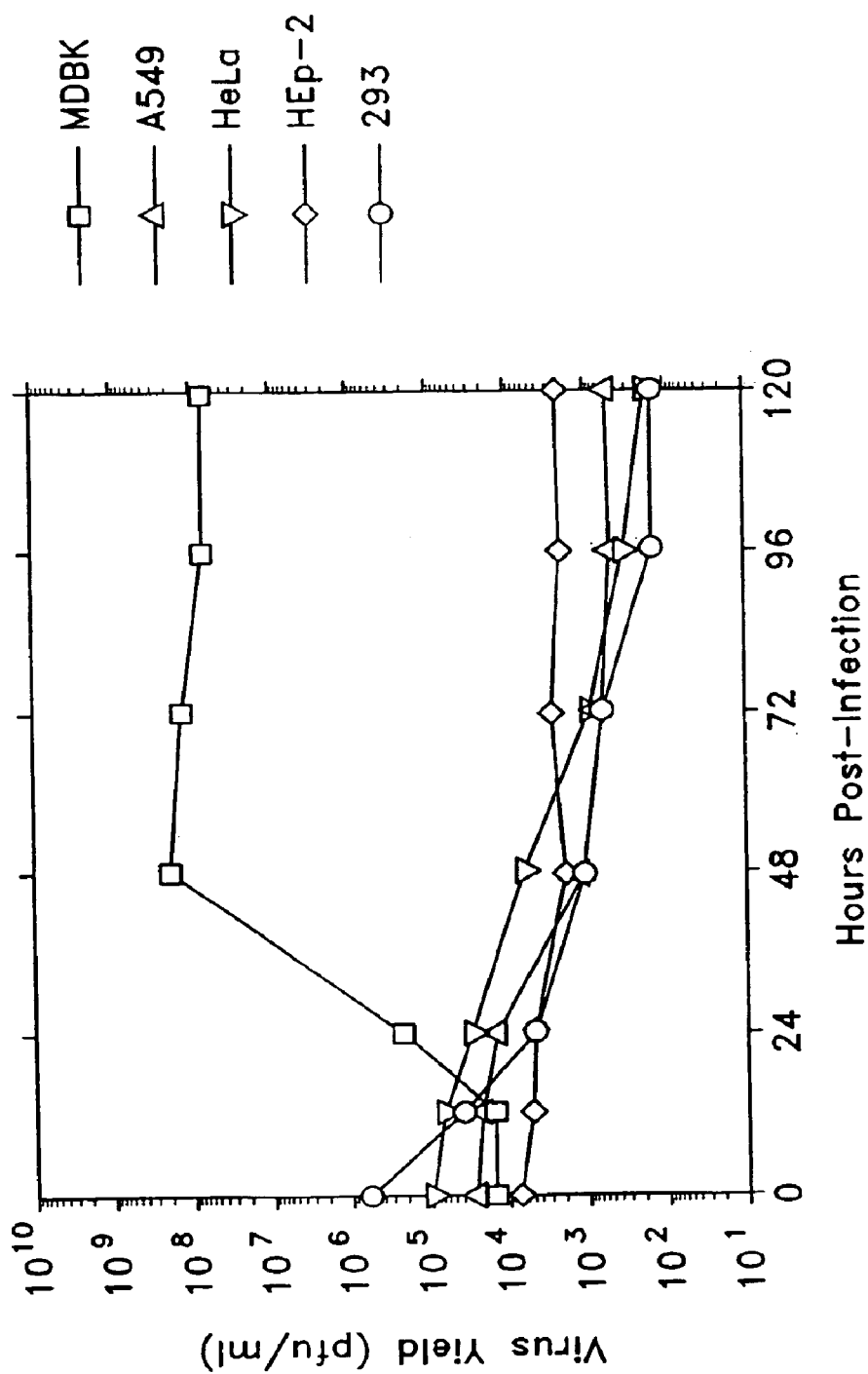
FIG. 10 illustrates BAV3 replication in human cells.

To characterize the transduction efficiency of BAV304 and BAV600 in different human cell lines, FACS analysis was performed to determine the percentage of transduction of each cell line at different virus input (FIG. 7A). Cells grown in T25 flasks were infected at an MOI of 1 and 5 with either BAV304 or BAV600. Forty-eight hours after infection, the percentage of GFP-fluorescence positive cells were determined by flow cytometry. The percentage of transduction of each cell line was quantitated, and the fraction of dose is shown in FIG. 7B. 293 cells were equally susceptible to transduction with both viruses (indicating that both the HAV-5 and BAV-3 receptors are present on the cell surface.) The transduction of HeLa and HEp-2 cells with BAV304 is dose dependent, with about 6% and 1% respectively at an MOI of 1 and about 25% and 5% respectively at an MOI of 5. Both cells were efficiently transduced with BAV600. The percentage of transduction with BAV600 reaches maximum level even at an MOI of 1 (94% and 93% for HeLa and Hep-2 respectively). In contrast less-efficient transduction of A549 cells with BAV600 was observed. These data taken together demonstrate that the BAV600 containing HAV-5 fiber knob was clearly superior to the BAV304 vector in transduction of human cell lines.

Example 4

HAV-5 and BAV-3 Neutralizing Antibodies in Human Serum

Preexisting neutralizing antibodies against HAV-5 in clinical patients represent a major obstacle for efficient use of HAV-5 in human gene therapy protocol. In order to explore the possibility for use of BAV-3 as an alternative vector to HAV-5-derived vectors, it was determined whether preexisting anti-HAV-5 neutralizing antibodies were also cross-reactive with BAV-3. 105 random samples of human sera from clinical patients were tested. Three (#50, 97, and 102) were found containing high titer of HAV-5 neutralizing antibodies ranging between 1:800 to 1,6000. These sera were tested for their ability to inhibit BAV-3-induced plaque formation on MDBK cells. Our data demonstrated that none of these HAV-5 positive sera showed effect on BAV-3-induced plaque formation at a dilution of 1/50.

Example 5

Replication of BAV-3 in Human Cell Lines

Virus production and the time course of virus infection were studied in different human cell lines to determine their degree of permissivity for BAV-3 growth. Confluent monolayer cultures of each cell line (HeLa, HEp-2, 293 and A549) were infected-with BAV-3 at an MOI of 10 and virus production at different time intervals after infection was assayed by titration of the cell lysates on MDBK cell monolayers. Virus growth in permissive MDBK cells resulted in, as expected, maximum yields of $10^8$ pfu/ml by 48 hours after infection. In contrast, the level of BAV-3 production in all four human cell lines was constantly diminished, suggesting that there is a complete absence of viral replication in these human cell lines.

Example 6

Expression of Early and Later BAV-3 Proteins in Human Cell Lines

Viral proteins include early proteins (E1B small and single-stranded DNA binding protein [DBP])and late proteins (penton base and fiber). To identify the expression of early and late viral proteins in human cell lines, viral protein production was analyzed by Western immunoblotting. Cultures were infected with BAV-3 at an MOI of 10. At intervals after infection, cell extracts were prepared from each culture, separated on 10% SDS-PAGE, and transferred to nitrocellulose. Antigens immobilized on the nitrocellulose sheets were probed by reaction with rabbit polyclonal antibodies against E1B small, DBP, penton base, and fiber respectively. As expected, the E1B small and DBP antisera reacted with bands in 19 and 50 kDa, respectively, from BAV-3-infected MDBK cells. In contrast, all human cell lines except 293 cell lines showed no positive reactions with anti-E1B small or DBP polyclonal antibodies. No structural proteins were detected from BAV-3-infected human cell lines. These results indicated that the replication of BAV-3 in the majority of human cells tested in this study was blocked at E1B small level.

Example 7

Neutralization of BAV600 by an Monoclonal Antibody Specific for HAV-5 Fiber Knob It was hypothesized that BAV600 carrying the HAV-5 fiber knob should be neutralized by an antibody specific for HAV-5 knob. To confirm this, duplicate aliquots containing 100 pfu of BAV-3 or BAV600 were incubated at room temperature for two hours with serial twofold dilutions of a rabbit polyclonal antibody specific for the BAV3 fiber knob or a monoclonal antibody, 1D6.14, against HAV-5 fiber knob domain. MDBK cells were then infected with pre-incubated BAV-3 or BAV600 virus. Cells were incubated for 14 days to allow a complete CPE to develop. The data show that that none of the viruses were neutralized by serum from normal rabbit serum or a control monoclonal antibody 2C8 specific for bovine herpesvirus gD protein BAV-3 and BAV600 were each neutralized by a rabbit polyclonal antibody specific for the BAV3 fiber knob (1:800) and ID6.14 (1:3,200), respectively. However, neither virus was neutralized by the reciprocal antiserum even at a dilution of 1:50. This further confirmed that BAV600 carried the HAV-5 fiber knob.

What is claimed is:

1. A recombinant bovine adenovirus vector comprising a modification in a polynucleotide encoding a capsid protein, or fragment thereof, wherein said capsid protein, or fragment thereof, is associated with tropism and wherein said modification is associated with altered tropism.

2. The adenovirus vector of claim 1 wherein said polynucleotide encoding a capsid protein, or fragment thereof, is replaced with a polynucleotide encoding a heterologous mammalian adenovirus capsid protein, or fragment thereof.

3. The adenovirus vector of claim 1 wherein said capsid protein, or fragment thereof, is a penton protein, or fragment thereof.

4. The adenovirus vector of claim 1 wherein said capsid protein, or fragment thereof, is a hexon protein, or fragment thereof.

5. The adenovirus vector of claim 1 wherein said capsid protein, or fragment thereof, is a fiber protein, or fragment thereof.

6. The adenovirus vector of claim 5 wherein the fiber protein, or fragment thereof, comprises the knob region of a fiber protein.

7. The adenovirus vector of claim 3 wherein said polynucleotide encoding the penton protein, or fragment thereof, is replaced with at least one polynucleotide encoding a heterologous mammalian adenovirus penton protein, or fragment thereof.

8. The adenovirus vector of claim 4 wherein said polynucleotide encoding the hexon protein, or fragment thereof, is replaced with at least one polynucleotide encoding a heterologous mammalian adenovirus hexon protein, or fragment thereof.

9. The adenovirus vector of claim 5 wherein said polynucleotide encoding the fiber protein, or fragment thereof, is replaced with at least one polynucleotide encoding a heterologous mammalian adenovirus fiber protein or fragment thereof.

10. The adenovirus vector of claim 2 wherein said heterologous mammalian adenovirus capsid protein, or fragment thereof, includes porcine, ovine, canine or human adenovirus capsid protein, or fragment thereof.

11. The adenovirus vector of claim 10 wherein said heterologous mammalian adenovirus capsid protein, or fragment thereof, is a human adenovirus capsid protein, or fragment thereof.

12. The adenovirus vector of claim 1 wherein said adenovirus is a sub-type 1 adenovirus.

13. The adenovirus vector of claim 1 wherein said adenovirus is a sub-type 2 adenovirus.

14. The adenovirus vector of claim 12 wherein said adenovirus vector is BAV3.

15. The adenovirus vector of claim 14 wherein said modification in a polynucleotide encoding a capsid protein, or fragment thereof, is a replacement of a polynucleotide encoding a BAV3 fiber protein, or fragment thereof, with a polynucleotide encoding a heterologous mammalian adenovirus fiber protein, or fragment thereof.

16. The adenovirus vector of claim 15 wherein said mammalian adenovirus fiber protein, or fragment thereof, includes bovine, porcine, ovine, canine or human adenovirus fiber protein, or a fragment thereof.

17. The adenovirus vector of claim 16 wherein said mammalian adenovirus fiber protein is a human adenovirus fiber protein.

18. The adenovirus vector of claim 1 wherein said vector lacks E1 function.

19. The adenovirus vector of claim 18 wherein said vector has a deletion of part or all of the E1 gene region.

20. The adenovirus vector of claim 1 wherein said vector has a deletion of part or all of the E3 gene region.

21. The adenovirus vector of claim 1 wherein said vector further comprises a polynucleotide encoding a heterologous protein.

22. The adenovirus vector of claim 21 wherein said heterologous protein includes cytokines; lymphokines; membrane receptors recognized by pathogenic organisms; dystrophins; insulin; proteins participating in cellular ion channels; antisense RNAs; proteins capable of inhibiting the activity of a protein produced by a pathogenic gene; a protein inhibiting an enzyme activity; protein variants of pathogenic proteins; antigenic epitopes; major histocompatibility complex classes I and II proteins; antibodies; immunotoxins; toxins; growth factors or growth hormones; cell receptors or their ligands; tumor suppressors; cellular enzymes; or suicide genes.

23. The adenovirus vector of claim 22 wherein said polynucleotide encoding said heterologous protein is inserted in the adenovirus E1 gene region.

24. The adenovirus vector of claim 22 wherein said polynucleotide encoding said heterologous protein is inserted in the adenovirus E3 gene region.

25. The adenovirus vector of claim 1 wherein said vector is replication-competent.

26. The adenovirus vector of claim 1 wherein said vector is replication-defective.

27. A host cell comprising the bovine adenovirus vector of claim 1.

28. A host cell comprising the bovine adenovirus vector of claim 21.

29. A method of producing a recombinant bovine adenovirus vector comprising a modification in a polynucleotide encoding a capsid protein, or a fragment thereof, comprising the steps of, obtaining a bovine adenovirus vector comprising a modification in a polynucleotide encoding a capsid protein, or fragment thereof, wherein said capsid protein, or fragment thereof, is associated with tropism and wherein said modification is associated with altered tropism, and culturing the adenovirus vector under conditions suitable for production of the bovine adenovirus vector.

30. The method of claim 29 wherein said capsid protein, or fragment thereof, is a penton protein, or fragment thereof.

31. The method of claim 29 wherein said capsid protein, or fragment thereof, is a hexon protein, or fragment thereof.

32. The method of claim 29 wherein said capsid protein, or fragment thereof, is a fiber protein, or fragment thereof.

33. The method of claim 29 wherein said adenovirus vector further comprises a polynucleotide encoding a heterologous protein.

34. The method of claim 29 wherein said bovine adenovirus is a sub-type 1 bovine adenovirus.

35. A recombinant bovine adenovirus comprising a modification in a polynucleotide encoding a capsid protein, or fragment thereof, wherein said capsid protein, or fragment thereof, is associated with tropism and wherein said modification is associated with altered tropism.

36. The recombinant adenovirus of claim 35 further comprising a polynucleotide encoding a heterologous protein.

37. The recombinant adenovirus of claim 36 wherein said polynucleotide encoding said heterologous protein is inserted in the adenovirus E1 gene region.

38. The recombinant adenovirus of claim 36 wherein said polynucleotide encoding said heterologous protein is inserted in the adenovirus E3 gene region.

39. The recombinant adenovirus of claim 35 wherein said capsid protein, or fragment thereof, is a penton protein, or fragment thereof.

40. The recombinant adenovirus of claim 35 wherein said capsid protein, or fragment thereof, is a hexon protein, or fragment thereof.

41. The recombinant adenovirus of claim 35 wherein said capsid protein, or fragment thereof, is a fiber protein, or fragment thereof.

42. The recombinant adenovirus of claim 41 wherein the fiber protein, or fragment thereof comprises the knob region of a fiber protein.

43. An immunogenic composition comprising a recombinant bovine adenovirus wherein said adenovirus comprises a modification in a polynucleotide encoding a capsid protein, or fragment thereof, and wherein said capsid protein, or fragment thereof, is associated with tropism and wherein said modification is associated with altered tropism.

44. The immunogenic composition of claim 43 wherein said capsid protein is a penton protein, or fragment thereof.

45. The immunogenic composition of claim 43 wherein said capsid protein is a hexon protein, or fragment thereof.

46. The immunogenic composition of claim 43 wherein said capsid protein is a fiber protein, or fragment thereof.

47. The immunogenic composition of claim 46 wherein said fiber protein, or fragment thereof, comprises the knob region of a fiber protein.

48. The immunogenic composition of claim 43 wherein said modification in a polynucleotide encoding a capsid protein or fragment thereof is a replacement of a polynucleotide encoding a bovine fiber protein, or fragment thereof, with a polynucleotide encoding a mammalian adenovirus fiber protein, or fragment thereof.

49. The immunogenic composition of claim 48 wherein said mammalian adenovirus fiber protein, or fragment thereof, is a human adenovirus fiber protein, or fragment thereof.

50. The immunogenic composition of claim 43 wherein said bovine adenovirus is a sub-type 1 adenovirus.

51. The immunogenic composition of claim 50 wherein said bovine adenovirus is BAV3.

52. The immunogenic composition of claim 43 wherein said bovine adenovirus comprises a polynucleotide encoding a heterologous protein.

53. A pharmaceutical composition capable of inducing an immune response in a mammalian subject, said composition comprising the immunogenic composition of claim 52.

54. The pharmaceutical composition of claim 53 further comprising a pharmaceutically acceptable excipient.

55. A method for eliciting an immune response in a mammalian host, the method comprising administration of the pharmaceutical composition of claim 54 to the mammalian host, wherein said heterologous protein comprises an antigenic epitope.

56. A composition comprising the adenovirus vector of claim 1.

57. A composition comprising the adenovirus vector of claim 5.

58. A composition comprising the adenovirus vector of claim 21.

59. A composition comprising the adenovirus of claim 35.

60. A composition comprising the adenovirus of claim 41.

61. The immunogenic composition of claim 48 wherein said mammalian adenovirus fiber protein, or fragment thereof, includes porcine, ovine, canine or human adenovirus capsid protein, or fragment thereof.

62. A host cell comprising the adenovirus vector of claim 5.

63. A host cell comprising the adenovirus of claim 35.

64. A host cell comprising the adenovirus of claim 41.

* * * * *

SEQUENCE LISTING

<160> NUMBER OF SEQ ID NOS: 9

<210> SEQ ID NO 1
<211> LENGTH: 34446
<212> TYPE: DNA
<213> ORGANISM: Bovine Adenovirus 3

<400> SEQUENCE: 1

-continued

```
catcatcaat aatctacagt acactgatgg cagcggtcca actgccaatc attttttgcca      60 cgtcatttat gacgcaacga cggcgagcgt ggcgtgctga cgtaactgtg gggcggagcg     120
cgtcgcggag gcggcggcgc tgggcggggc tgagggcggc gggggcggcg cgcggggcgg     180
cgcgcggggc ggggcgaggg gcggagttcc gcacccgcta cgtcattttc agacattttt     240
tagcaaattt gcgcccttttg caagcatttt tctcacattt caggtattta gagggcggat     300
ttttggtgtt cgtacttccg tgtcacatag ttcactgtca atcttcatta cggcttagac     360
aaattttcgg cgtctttttcc gggtttatgt ccccggtcac ctttatgact gtgtgaaaca     420
cacctgccca ttgtttaccc ttggtcagtt ttttcgtctc ctagggtggg aacatcaaga     480
acaaatttgc cgagtaattg tgcacctttt tccgcgttag gactgcgttt cacacgtaga     540 cagactttt ctcattttct cacactccgt cgtccgcttc agagctctgc gtcttcgctg     600
ccaccatgaa gtacctggtc ctcgttctca acgacggcat gagtcgaatt gaaaaagctc     660
tcctgtgcag cgatggtgag gtggatttag agtgtcatga ggtacttccc ccttctcccg     720
cgcctgtccc cgcttctgtg tcacccgtga ggagtcctcc tcctctgtct ccggtgtttc     780
ctccgtctcc gccagccccg cttgtgaatc cagaggcgag ttcgctgctg cagcagtatc     840
ggagagagct gttagagagg agcctgctcc gaacggccga aggtcagcag cgtgcagtgt     900
gtccatgtga gcggttgccc gtggaagagg atgagtgtct gaatgccgta aatttgctgt     960
ttcctgatcc ctggctaaat gcagctgaaa atgggggtga tatttttaag tctccggcta    1020
tgtctccaga accgtggata gatttgtcta gctacgatag cgatgtagaa gaggtgacta    1080
gtcacttttt tctggattgc cctgaagacc ccagtcggga gtgttcatct tgtgggtttc    1140
atcaggctca aagcggaatt ccaggcatta tgtgcagttt gtgctacatg cgccaaacct    1200
accattgcat ctatagtaag tacattctgt aaaagaacat cttggtgatt tctaggtatt    1260
gtttagggat taactgggtg gagtgatctt aatccggcat aaccaaatac atgttttcac    1320
aggtccagtt tctgaagagg aaatgtgagt catgttgact ttggcgcgca agaggaaatg    1380
tgagtcatgt tgactttggc gcgccctacg gtgactttaa agcaaatttga ggatcacttt    1440 tttgttagtc gctataaagt agtcacggag tcttcatgga tcacttaagc gttctttttgg    1500 atttgaagct gcttcgctct atcgtagcgg gggcttcaaa tcgcactgga gtgtggaaga    1560
ggcggctgtg gctgggacgc ctgactcaac tggtccatga tacctgcgta gagaacgaga    1620
gcatatttct caattctctg ccagggaatg aagcttttttt aaggttgctt cggagcggct    1680
attttgaagt gttttgacgtg tttgtggtgc ctgagctgca tctggacact ccgggtcgag    1740
tggtcgccgc tcttgctctg ctggtgttca tcctcaacga tttagacgct aattctgctt    1800
cttcaggctt tgattcaggt tttctcgtgg accgtctctg cgtgccgcta tggctgaagg    1860
ccagggcgtt caagatcacc cagagctcca ggagcacttc gcagccttcc tcgtcgcccg    1920
acaagacgac ccagactacc agccagtaga cggggacagc ccaccccggg ctagcctgga    1980
ggaggctgaa cagagcagca ctcgtttcga gcacatcagt taccgagacg tggtggatga    2040
cttcaataga tgccatgatg tttttttatga gaggtacagt tttgaggaca taaagagcta    2100
cgaggctttg cctgaggaca atttggagca gctcatagct atgcatgcta aaatcaagct    2160
gctgcccggt cgggagtatg agttgactca acctttgaac ataacatctt gcgcctatgt    2220
gctcggaaat ggggctacta ttagggtaac aggggaagcc tccccggcta ttagagtggg    2280
ggccatggcc gtgggtccgt gtgtaacagg aatgactggg gtgactttg tgaattgtag    2340
```

```
gtttgagaga gagtcaacaa ttaggggtc cctgatacga gcttcaactc acgtgctgtt    2400
tcatggctgt tattttatgg gaattatggg cacttgtatt gaggtggggg cgggagctta    2460 cattcgggt tgtgagtttg tgggctgtta ccggggaatc tgttctactt ctaacagaga    2520
tattaaggtg aggcagtgca actttgacaa atgcttactg ggtattactt gtaagggga    2580 ctatcgtctt tcgggaaatg tgtgttctga gactttctgc tttgctcatt tagagggaga    2640
gggtttggtt aaaacaaca cagtcaagtc cctagtcgc tggaccagcg agtctggctt    2700
ttccatgata acttgtgcag acggcagggt tacgcctttg ggttccctcc acattgtggg    2760
caaccgttgt aggcgttggc caaccatgca ggggaatgtg tttatcatgt ctaaactgta    2820
tctgggcaac agaataggga ctgtagccct gccccagtgt gctttctaca agtccagcat    2880
ttgtttggag gagagggcga caaacaagct ggtcttggct tgtgcttttg agaataatgt    2940
actggtgtac aaagtgctga gacgggagag tccctcaacc gtgaaaatgt gtgtttgtgg    3000
gacttctcat tatgcaaagc ctttgacact ggcaattatt tcttcagata ttcgggctaa    3060
tcgatacatg tacactgtgg actcaacaga gttcacttct gacgaggatt aaaagtgggc    3120
ggggccaaga gggtataaa taggtgggga ggttgagggg agccgtagtt tctgtttttc    3180
ccagactggg ggggacaaca tggccgagga agggcgcatt tatgtgcctt atgtaactgc    3240
ccgcctgccc aagtggtcgg gttcggtgca ggataagacg ggctcgaaca tgttgggggg    3300
tgtggtactc cctcctaatt cacaggcgca ccggacggag accgtgggca ctgaggccac    3360
cagagacaac ctgcacgccg agggagcgcg tcgtcctgag gatcagacgc cctacatgat    3420
cttggtggag gactctctgg gaggtttgaa gaggcgaatg gacttgctgg aagaatctaa    3480
tcagcagctg ctggcaactc tcaaccgtct ccgtacagga ctcgctgcct atgtgcaggc    3540
taaccttgtg ggcggccaag ttaacccctt tgtttaaata aaaatacact catacagttt    3600
attatgctgt caataaaatt ctttattttt cctgtgataa taccgtgtcc agcgtgctct    3660
gtcaataagg gtcctatgca tcctgagaag ggcctcatat accatggcat gaatattaag    3720
atacatgggc ataaggccct cagaagggtt gaggtagagc cactgcagac tttcgtgggg    3780
aggtaaggtg ttgtaaataa tccagtcata ctgactgtgc tgggcgtgga aggaaaagat    3840 gtctttaga agaagggtga ttggcaaagg gaggctctta gtgtaggtat tgataaatct    3900
gttcagttgg gagggatgca ttcgggggct aataaggtgg agtttagcct gaatcttaag    3960
gttggcaatg ttgcccccta ggtctttgcg aggattcatg ttgtgcagta ccacaaaaac    4020
agagtagcct gtgcatttgg ggaatttatc atgaagcttg gaggggaagg catgaaaaaa    4080
ttttgagatg gctttatggc gccccaggtc ttccatgcat tcgtccataa taatagcaat    4140
aggcccggtt ttggctgcct gggcaaacac gttctgaggg tgggcgacat catagttgta    4200
gtccatggtc aggtcttcat aggacatgat cttaaaggca ggttttaggg tgctgctttg    4260
aggaaccaga gttcctgtgg ggccgggggt gtagttccct tcacagattt gggtctccca    4320
agcaagcagt tcttgcgggg gtatcatgtc aacttggggg actataaaaa aaacagtttc    4380
gggaggtggt tgaatgaggc ccgtagacat aaggtttctg aggagctggg attttccaca    4440
accggttggt ccgtagacca ccccaataac gggttgcatg gtaaagttta aagatttgca    4500
tgaaccgtca gggcgcagat atggcatggt ggcattcatg gcatctctta tcgcctgatt    4560
atagtctgag agggcattga gtagggtggc gcccccata gccagtagct cgtccaagga    4620
agaaaagtgt ctaagaggtt tgaggccttc agccatgggc atggactcta agcactgttg    4680
catgagagca catttgtccc aaagctcaga gacgtggtct agtacatctc catccagcat    4740
```

-continued

```
agctctttgt tcttgggtt ggggtggctg ttgctgtagg gggcgagacg gtgacggtcg    4800
atggcccgca gggtgcggtc tttccagggc ctgagcgtcc tcgccagggt cgtctcggtg    4860
accgtgaagg gctgctgatg cgtctgtctg ctgaccagcg agcgcctcag gctgagcctg    4920
ctggtgccga acttttcgtc gcctagctgt tcagtggaat aataacaagt caccagaagg    4980
tcgtaggaga gttgtgaggt ggcatggcct tgctcgaaag tttgccagaa ctctcggcgg    5040
cggcagcttg ggcagtagat gttttttaagg gcatatagtt tgggggctaa aagacagat    5100 tcctggctgt gggcgtctcc gtggcagcgg gggcactggg tctcgcattc cacaagccaa    5160
gtcagctgag ggttggtggg atcaaagacc agaggacggt tattaccttt caggcggtgc    5220
ttgcctcggg tgtccatgag ttcctttccc ctttgggtga aaacatgct gtccgtgtct     5280 ccgtagacaa atttgagaat ccggtcttct agggagtgc ctctgtcttc taaatagagg     5340
atgtctgccc attcagagac aaaggctcta gtccacgcga ggacaaatga agctatgtgt    5400 gagggtatc tgttattaaa tatgagagag dattttttt gcaaagtatg caggcacagg      5460
gctgagtcat cagcttccag aaaggtgatt ggtttgtaag tgtatgtcac gtgatggttc    5520 tggggtctc ccagggtata aaaggggggcg tcttcgtctg aggagctatt gctagtgggt    5580
gtgcactgac ggtgcttccg cgtggcatcc gtttgctgct tgacgggtga gtaggtgatt    5640
tttagctctg ccatgacaga ggagctcagg ttgtcagttt ccacgaaggc ggtgcttttg    5700
atgtcgtagg tgccgtctga aatgcctcta acatatttgt cttccatttg gtcagaaaag    5760
acagtgactc tgttgtctag cttagtggca aagctgccat acagggcatt ggacagcagt    5820
ttggcaatgc ttctgagagt ttggttttc tctttatccg cccctttcctt gggcgcaatg     5880 ttaagttgca cgtagtctct agccagacac tcccactggg gaaatactgt ggtgcgggg    5940 tcgttgagaa tttggactct ccagccgcgg ttatgaagcg tgatggcatc caaacaagtt    6000
accacttccc cccgtagtgt ctcgttggtc cagcagaggc gacctccttt tctggagcag    6060
aagggcggta taacgtccaa gaatgcttct gggggtgggt ctgcatcaat ggtgaatatc    6120
gcgggcagta gggtgcgatc aaaatagtca atgggtctgt gcaactgggt taggcggtct    6180
tgccagtttt taattgcaag cgctcgatca aaggggttca aaggttttcc cgctgggaaa    6240
ggatgggtga gggcgctggc atacatgccg cagatgtcat acacatagat ggcttctgtt    6300
aggacgccta tgtaggtagg atagcatcgg ccgccccgaa tactttctct aacgtaatca    6360
tacatttcat tggaagggc tagtagaaag ttgcccagag agctcctgtt gggacgctgg    6420
gatcggtaga ctacctgtct gaagatggca tgggaattgg agctgatggt gggccttttgg   6480 aggacattga aattgcagtg gggcagcccc actgacgtgt gaacaaagtc caaataagat    6540
gcttggagtt ttttaaccaa tcggccgta accagcacgt ccatagcaca gtagtccaag      6600
gtgcgttgca caatatcata ggcacctgaa ttctcttgca gccagagact cttattgaga    6660
aggtactcct cgtcgctgga ccagtagtcc ctctgaggaa aagaatctgc gtcggttcgg    6720
taggtaccta acatgtaaaa ttcatttaca gctttgtaag ggcagcagcc ttttttccacg   6780 ggtaaagcgt aagcggcagc tgcgttcctg agactcgtgt gcgtgagagc aaaggtatct    6840
cggaccatga acttcacaaa ctgaaattta tagtctgctg aggtgggagt gccttcctcc    6900
cagtctttga agtctttttcg agcagcatgt gtggggttag gcagagcaaa agttaagtca    6960
ttgaaaagaa tcttgccaca acgaggcatg aaatttctac tgactttaaa agcagctgga    7020
ataccttgtt tgttgttaat gacttgtgcg gctagaacaa tctcatcaaa gccgtttatg    7080
```

```
ttgtgcccta cgacatagac ttccaagaaa gtcggttgcc ctttgagttc aagcgtacac    7140
agttcctcga aaggaatgtc gctggcatgg acatagccca gtttgaggca gaggttttct    7200
aagcacggat tatctgccag gaactggcgc caaagcaaag tgctggcagc ttcttgaagg    7260
gcatcccgat actgttaaa caagctgcct actttgtttc tttgcgggtt gaggtagtag    7320
aaggtatttg cttgctttgg ccagcttgac cacttttgct ttttagctat gttaacagcc    7380
tgttcgcata gctgcgcgtc accaaacaaa gtaaacacga gcataaaagg catgagttgc    7440
ttgccaaagc taccgtgcca agtgtatgtt tccacatcat agacgacaaa gaggcgccgg    7500
gtgtcggggt gagcggccca ggggaaaaac tttatttctt cccaccagtc cgaagattgg    7560
gtgtttatgt ggtgaaagta aaagtcccgg cggcgagtgc tgcaggtgtg cgtctgctta    7620
aaatacgaac cgcagtcggc acatcgctgg acctctgcga tggtgtctat gagatagagc    7680
tttctcttgt gaataagaaa gttgagggg aagggaaggc gcggcctgtc agcgcgggcc    7740
gggatgcttg taattttcag cttccccttg tatgttttgt aaacgcacat atttgcgttg    7800
cagaaccgga cgagcgtgtc ttggaatgaa aggatatttt ctggttttaa atcaaatggg    7860
cagtgctcca agtgcagttc aaaaaggttt cggagactgc tggaaacgtc tgcgtgatac    7920
ttgacttcca gggtggtccc gtcttcagtc tgaccgtgca gccgtagggt actgcgtttg    7980
gcgaccaggg gccccttgg ggctttcttt aaaggggacg tcgagggccg aggggcggcc    8040
tttgcctttc gggcctgagg ggcggtagct ggaccggatc gttgagttcg ggcatgggtt    8100
gcagctgttg gcgcaggtct gatgcgtgct gcacgactct gcggttgatt ctctgaatct    8160
ccgggtgttg ggtgaatgct actggccccg tcactttgaa cctgaaagag aggtcgacag    8220
agttaataga tgcatcgtta agctccgcct gtctaataat ttcttccacg tcaccgctgt    8280
ggtctcggta agcaatgtct gtcataaacc gttcgatctc ttcctcgtcc agttctccgc    8340
gaccagctcg gtggaccgtg gctgccaagt ccgtgctaat gcgtcgcatg agctgggaaa    8400
aggcattggt tcccggttca ttccacactc tgctgtatat aacagcgcca tcttcgtctc    8460
gggctcgcat gaccacctgg cccaagttta gctccacgtg gcgagcaaag acggggctga    8520
ggcggaggtg gtggtgcaga taattgagag tggtggctat gtgctccacg atgaagaagt    8580
agatgaccca tctgcggatg gtcgactcgt taatgttgcc ctctcgctcc agcatgttta    8640
tggcttcgta aaagtccaca gcgaagttaa aaaactgctc gttgcgggcg gagactgtca    8700
gctcttcttg caggagacga atgacttcgg ctacggcggc gcggacttct tcggcaaagg    8760
agcgcggcgg cacgtcctcc tcctcctctt cttcccctc cagcggggc atctccagct    8820 ctaccggttc cgggctgggg gacagggaag gcggtgcggg ccgaacgacc cgtcggcgtc    8880
gggtgggcaa ggggagactc tctatgaatc gctgcaccat ctcgccccgg cgtatccgca    8940
tctcctgggt aacggcacgc ccgtgttctc ggggtcggag ctcaaaagct ccgccccgca    9000
gttcggtcag aggccgcgcc gcgggctggg gcaggctgag tgcgtcaata acatgcgcca    9060
ccactctctc cgtagaggcg gctgtttcga accgaagaga ctgagcatcc acgggatcgc    9120
tgaagcgttg cacaaaagct tctaaccagt cgcagtcaca aggtaggctg agcataggtg    9180
aggctcgctc ggtgttgttt ctgtttggcg gcgggtggct gaggagaaaa ttaaagtacg    9240
cgcaccgcag gcgccggatg gttgtcagta tgatgagatc cctgcgaccc gcttgttgga    9300
ttctgatgcg gtttgcaaag ccccaggctt ggtcttggca tcgcccaggt tcatgcactg    9360
ttcttggagg aatctctcta cgggcacgtt gcggcgctgc gggggcaggg tcagccattt    9420
cggtgcgtcc aaacccacgc aatggttgga tgagagccaa gtccgctact acgcgctctg    9480
```

```
ctaggacggc ttgctggatc tgccgcagcg tttcatcaaa gttttccaag tcaatgaagc      9540
ggtcgtaggg gcccgcgttt atggtgtagg agcagtttgc catggtggac cagtccacaa      9600
tctgctgatc tacccgcacc gtttctcggt acaccagtcg gctataggct cgcgtctcga      9660
aaacatagtc gttgcaaacg cgcaccacgt attggtagcc gattaggaag tgcggcggcg      9720
ggtataagta gagcggccag ttttgcgtgg ccggctgtct ggcgcccaga ttccgtagca      9780
tgagtgtggg gtatcggtac acgtgacgcg acatccagga gatgcccgcg gccgaaatgg      9840
cggccctggc gtactcccgg gcccggttcc atatattcct gagaggacga aagattccat      9900
ggtgtgcagg gtctgccccg taagacgcgc gcaatctctc gcgctctgca aaaacatac       9960 agatgaaaca ttttgggc ttttcagatg atgcatcccg ctttacggca aatgaagccc      10020
agatccgcgg cagtggcggg ggttcctgct gcggccgccg gcgcgagcgt tgactcaggc     10080
ggtactaccg cgcccctgg tgtcgagtgc ggcgagggggg aagggttagc tcggctgtac     10140
gcgcacccgg acacacaccc gcgcgtgtgc gtgaagcgcg atgcggcgga ggcgtacgtt     10200
ccccgggaga acttattccg cgaccgcagc ggggaggaac ccgaagggag ccgagaccta     10260
aagtacaagg ccggtcggca gttgcgcgcc ggcatgcccc gaaagcgggt gctgaccgaa     10320
ggggactttg agtggatga gcgcactggc atcagctcag ccaaagccca catggaggcg     10380
gccgatctag tgcgggctta cgagcaaacg gtgaagcaag aggctaattt tcaaaagtca     10440
tttaataacc acgtgcggac actgatctcc cgcgaggaga ccaccctggg tttgatgcac     10500
ttgtgggact ttgcggaggc atacgcgcag aaccccggca gcaagaccct tacggcccaa     10560
gtctttctca tcgtgcagca cttgcaagat gagggcattt ttggggaagc tttcttaagc     10620
atagcagagc ccgagggacg atggatgcta gatctgctaa acatattgca gtccattgtg     10680
gtgcaagagc gccagctttc gctatctgaa aaggtagccg cggtgaacta ctccgtagtt     10740
accctgggca acattatgc ccgcaagatc tttaagagcc cctttgtgcc gcttgacaag     10800
gaggtgaaga tcagtacatt ttatatgcgc gcggtgctta aggtcctggg tctaagtcac     10860
gacctgggca tgtacagaaa cgaaaaggtg gagaagctag ctagcatagg caggcgttcg     10920
ggagatgagc gacgcggagc tgctgttcaa cctccgccgc gcactaacca ctggcgattc     10980
tgaagcattc gatgaaggcg gggacttttac ctgggctccg ccaactcgcg cgaccgcggc     11040
ggccgctttg ccggggcccg agtttgagag tgaagagacg gacgatgaag tcgacgaatg     11100
agtgatgcgg accccccgtat ctttcagctg gtcagtcggc aagagaccgt agccatggcc     11160
gaagcgcccc gaagcctggg ccccgcccct tccaatccta gtttgcaggc tttattccaa     11220
agccagccca gcgccgagca ggagtggcac ggcgtgctgg agagagtcat ggcccttaac     11280
aaaaatggag actttggctc gcagccccag gcgaaccggt ttggagccat cctcgaagcc     11340
gtggtgcccc cgcgctccga tcccacccat gaaaaagtgc tagctattgt gaatgcgctc     11400
ttggagactc aggccatccg tcgcgatgag gccggacaga tgtacaccgc gctgttgcag     11460
cgggtggcca gatacaacag tgtgaatgtg caggcaatt tggacaggct gattcaggac     11520
gtgaaggagg ctctggcgca gcgcgagcgc accgggccgg gggccggcct agggtctgtg     11580
gtagccttga atgccttcct gagcacacag ccagcggtgg tggagagggg ccaggagaac     11640
tatgtggcct ttgtgagcgc cttaaaactc atggtgacca aggcgccgca gtctgaggtt     11700
taccaggccg gacctagttt cttttttcaa accagccggc acggttcgca gacggtaaac     11760
ctcagtcagg cctttgataa cttgcgaccc ctctggggcg tgcgcgcgcc agtacacgag     11820
```

| | |
|---|---|
| cgtactacca tctcctctct gctcacacca aacacccgct tgctcttgct cctcattgcg | 11880 |
| cccctttacgg acagcgtggg catatcccgg gacagttacc tggggcatct gctgacccct | 11940 |
| taccgggaga ccataggtaa cactcgagtt gatgagacca cgtacaacga gatcacggaa | 12000 |
| gtgagtcggg ccctgggcgc cgaagacgcg tctaacttgc aagccactct caactactta | 12060 |
| ctcacaaata agcagagcaa gttgccacag gagttttctc tgagtcccga agaggagcgg | 12120 |
| gtgctgcgct acgtgcagca atctgtcagt ttatttttaa tgcaggatgg acacacggcc | 12180 |
| accactgctc tagatcaggc tgcggccaac atagcgccct cgttttacgc gtcccaccgc | 12240 |
| gactttataa accgactgat ggactatttc cagcgagctg cggctatggc ccctgactac | 12300 |
| tttttacagg ctgttatgaa tccccactgg ctcccgccgc cgggtttctt tactcaggag | 12360 |
| tttgactttc cggagcccaa cgaaggcttc tgtgggatg atttggacag cgcgctccta | 12420 |
| cgcgcgcacg taaaagaaga ggaggatcaa ggagctgtgg gcggcacgcc ggcggcttcg | 12480 |
| gcgcccgcgt ctcgcgcgca cacaccaccg ccgccgcccg tgccgcgga cctctttgct | 12540 |
| cctaacgcct tccgcaatgt gcaaaataac ggcgtggatg aacttattga cggcttaagc | 12600 |
| agatggaaga cttacgccca ggagaggcag gaagtcgttg agcggcacag gcgcagagag | 12660 |
| gcgcgtcgcc gggcgcgcga ggcgcgtcta gagtcgagcg atgatgacga cagcgaccta | 12720 |
| gggccgtttc tacggggcac ggggcacctc gttcacaacc agtttatgca tctgaagccc | 12780 |
| cggggtcccc gccagttttg gtaaccgcac tgtattaagc tgtaagtcct ctcatttgac | 12840 |
| acttaccaaa gccatggtct tgcttcgcct ctgacacttt ctctcccccc acacgcggca | 12900 |
| ccctacagcc taggggcgat gctccagccc gaactgcagc caattccgct gtcccgccgc | 12960 |
| cggcttatga ggcggtggtg gctggggcct tccagacgct ttctcttcga cgagatccac | 13020 |
| gtcccgccgc gatatgctgc cgcgtctgcg gggagaaaca gtatccgtta ttccatgctg | 13080 |
| cccccgttgt atgacaccac gaagatatac cttatcgaca caaatcttc agacatccaa | 13140 |
| actctgaatt accaaaacga ccactcagat tacctcacta ccatcgtgca gaacagcgac | 13200 |
| ttcacgcccc tggaggctag caaccacagc atcgagctag acgagcggtc ccgctggggc | 13260 |
| ggaaaccta aaaccatcct ttatacaaac ctgcctaata tcacccagca catgttttct | 13320 |
| aactctttc gggtaaagat gatggcctca aaaaagacg gcgtgcccca gtacgagtgg | 13380 |
| ttccccctaa ggctgcccga gggtaacttt tctgagacta tggtcattga cctcatgaac | 13440 |
| aatgccatcg tagagctgta cttggctttg gggcgccagg agggcgtgaa ggaagaggac | 13500 |
| atcggggtaa agatcgatac gcgcaacttt agtctgggct atgacccgca gacccagtta | 13560 |
| gtgacgcccg gcgtatacac caatgaagct atgcatgcgg acatcgtgtt gctgccgggc | 13620 |
| tgtgctatag actttacgca ctcccgatta acaacctct tgggcatacg caagcgtttt | 13680 |
| ccgtaccaag agggcttcgt catctcctat gaggacctta aggggggtaa catccccgct | 13740 |
| ttgatggacg tggaggagtt taacaagagc aagacggttc gagctttgcg ggaggacccc | 13800 |
| aaggggcgca gttatcacgt gggcgaagac ccagaagcca gagaaaacga aaccgcctac | 13860 |
| cgcagctggt acctggctta caattacggg gacccagaaa aaggggtgcg ggccaccaca | 13920 |
| ctgctgacta ccggcgacgt gacctgcggg gtggaacaga tctactggag cttgccggac | 13980 |
| atggcactgg acccagtcac tttcaaggct tcgctgaaaa ctagcaatta ccccgtggtg | 14040 |
| ggcacagaac ttttgccact ggtgccgcgt agcttttata acgctcaggc tgtgtactca | 14100 |
| cagtggatac aagaaaaaac taaccagacc cacgttttca atcgctttcc cgaaaatcag | 14160 |
| atcttggtgc ggccccctgc gcctaccatc acgtccataa gtgaaaataa gcccagcttg | 14220 |

```
acagatcacg gaatcgtgcc gctccggaac cgcttggggg gcgtgcaacg tgtgactttg    14280
actgacgcgc ggcgaagatc ctgcccctac gtctacaaga gcttaggcat tgtgacgccg    14340
caagtgctat ctagccgcac gttttaagca gacaggggca cagcagccgt tttttttttt    14400
tttttttcgc tccaccaggg actgtcagga acatggccat tctaatctct cctagcaata    14460
acacgggctg gggcctggga tgcaataaga tgtacggggg cgctcgcata cgttcagact    14520
tgcatccagt gaaggtgcgg tcgcattatc gggccgcctg gggcagccgc accggtcggg    14580
tgggtcgccg cgcaaccgca gctttagccg atgccgtcgc ggccaccggt gatccggtgg    14640
ccgacacaat cgaggcggtg gtggctgacg cccgccagta ccggcgccgc agacggcgag    14700
gggtgcgccg agtcagaagg ttgcgtcgga gcccccgcac tgccctgcag cgacgggttc    14760
gtagcgtacg ccgacaagtg gcgagggccc gcaggtgggg ccggcgcgcg ccgctatcg    14820 cagcagacgc ggccatggcc atggcggcgc cagctcggcg acgccgtaac atctactggg    14880
tacgcgatgc ggcaaccgga gcccgcgttc cggtgacaac ccggcctacg gtcagcaaca    14940
ccgtttgaaa tgtctgctac ttttttttgc ttcaataaaa gcccgccgac tgatcagcca    15000
caccttgtca cgcagaattc tttcaaacca ttgcgctctc agcgcgcgcg ccgataaacc    15060
cactgtgatg gcctcctctc ggttgattaa agaagaaatg ttagacatcg tggcgcctga    15120
gatttacaag cgcaaacggc ccaggcgaga acgcgcagca ccgtatgctg tgaagcagga    15180
ggagaagcct ttagtaaagg cggagcgcaa aattaagcgc ggctccagaa agcgggcctt    15240
gtcaggcgtt gacgttcctc tgcccgatga cggctttgag gacgacgagc cccacataga    15300
atttgtgtct gcgccgcgtc ggccctacca gtggaagggc aggcgggtgc gccgggtttt    15360
gcgtcccggc gtggccgtta gtttcacgcc cggcgcgcg tccctccgtc cgagttccaa    15420
gcgggtgtat gacgaggtgt acgcagacga cgacttctta gaagcggccg cggcccgtga    15480
gggggagttt gcttacggaa agcggggacg cgaggcggcc caggcccagc tgctaccggc    15540
tgtggccgtg ccggaaccga cttacgtagt tttggatgag agcaaccca ccccgagcta    15600 caagcctgta accgagcaga aagttattct ttcccgcaag cggggtgtgg ggaaggtaga    15660
gcctaccatc caggttttag ctagcaagaa gcggcgcatg gccgagaatg aggatgaccg    15720
cggggccggc tccgtggccg aagtgcagat gcgagaagtt aaaccggtaa ccgctgcctt    15780
gggtattcag accgtggatg ttagcgtgcc cgaccacagc actcccatgg aggtcgtgca    15840
gagtctcagt cgggcggctc aagtagctca acgcctgacc caacaacagg tgcggccttc    15900
ggctaagatt aaagtggagg ccatggatct ttctgctccc gtagacgcaa agcctcttga    15960
cttaaaaccc gtggacgtaa agccgacccc gaccttcgtg cttcccagct ttcgttcact    16020
cagcacccaa actgactctt tgcccgcggc agtggtcgtg ccgcgcaagc ccgcgtgca    16080 ccgtgctact aggcgtactg cgcgcggctt gctgccctat taccgcctgc atcctagcat    16140
cacgccgaca ccgggttacc gaggatctgt ctacacgagc tcgggtgtgc gcctgcccgc    16200
cgtccgggcg ccgccgtcgc cgccgtaccc gcagggcgac tccccgcctc agcgctgccg    16260
cggccgcggc gctgctgccc ggcgtgcgct atcaccctag catccgccaa gcggccacag    16320
taacccggct ccgccgttaa gcgctgtgaa actgcaacaa caacaacaaa ataaaaaaa    16380 agtctccgct ccactgtgca ccgttgtcca tcggctaata aagtcccgct ttgtgcgccg    16440
caggaaccac tatccgtaac ctgcgaaaat gagtccccgc ggaaatctga cttacagact    16500
gagaataccg gtcgccctca gtggccggcg ccggcgccga acaggcttgc gaggagggtc    16560
```

```
tgcgtacctg ctcggccgcc gcagaaggcg cgcgggcggc ggccgcctgc gcggggcgctt    16620
ccttcccctc ctggctccca tcattgcagc cgccatcggc gcaatcccg gcatcgcatc      16680
agtggccatt caggcggccc acaacaaata gggacagtgt aaagaaagct caatctcaat     16740
aaaacaaacc gctcgatgtg cataacgctc tcggcctgca acttctgctg cttacgtctt     16800
tgaccaaagt cactactgtt ttccttttac ccagagccgg cgccagcccc acacagcttg     16860
ttaacacgcc atggacgaat acaattacgc ggctcttgct ccccggcaag gctcccgacc     16920
catgctgagc cagtggtccg gcatcggcac gcacgaaatg cacggcggac gttttaatct    16980
gggcagtttg tggagcggga tcaggaatgt gggcagcgcg ttaagaactg gggctctcgg    17040
gcctggcaca gcaatgcggg caagcgttgc gcgcccagct gaaaaagacg ggcttgcaag    17100
aaaagatatt gagggcgtta gcgccggtat ccacggagcc gtggatctgg gccgtcagca    17160
gctagagaaa gctattgagc agcgcctaga gcgtcgcccc accgctgccg gtgtggaaga    17220
ccttccgctt cccccgggaa cagtcttaga agctgatcgt ttaccgccct cctacgccga    17280
agcggtggct gagcgcccgc cgccggctga cgttctcctg cccgcatcct caaagccgcc    17340
ggtggcggtg gtgaccttgc ccccgaaaaa gagagtgtct gaagagcctg tggaggaagt    17400
tgtgattcgt tcctccgcac cgccgtcgta cgacgaggtt atggcaccgc agccgactct    17460
ggtagccgag cagggcgcca tgaaagcagt gcccgtgatt aagccggctc aaccttttac    17520
cccagctgtg cacgaaacgc aacgcatagt gaccaacttg ccaatcacca cagctgtgac    17580
acggcgacgc gggtggcagg gcactctgaa tgacatcgtg ggcctcggcg ttcgtaccgt    17640
gaagcgccgg cggtgctatt gaggggggcgc gcagcggtaa taaagagaac ataaaaaagc   17700
aggattgtgt tttttgttta gcggccactg actctccctc tgtgtgacac gtcctccgcc    17760
agagcgtgat tgattgaccg agatggctac cccgtcgatg ctgccgcaat ggtcctactg    17820
cacatcgccg gtcaggacgc gtccgagtac ctgtcccccg gcttggtgca attcgcacaa    17880
gccaccgaat cctactttaa cattgggaac aagtttagaa accccaccgt cgccccgacg    17940
cacgatgtca ccacggagcg ttcgcagcgt ctgcagctcc gcttcgtgcc cgtagaccgg    18000
gaggacacac agtactccta caaaacccgc ttccagctag ccgtgggcga caaccgggtg    18060
ctggacatgg ccagcacgta ttttgacatc cgcggtacgc tggagagggg cgccagtttc    18120
aagccttaca gcggcacggc ctacaactcc tttgccccca acagtgcccc taacaatacg    18180
cagtttaggc aggccaacaa cggtcatcct gctcagacca tagctcaagc ttcttacgtg    18240
gctaccatcg gcggtgccaa caatgacttg caaatgggtg tggacgagcg tcagcagccg    18300
gtgtatgcga acactacgta ccagccggaa cctcagctcg gcattgaagg ttggacagct    18360
ggatccatgg cggtcatcga tcaagcaggc gggcgggttc tcaggaaccc tactcaaact    18420
ccctgctacg ggtcctatgc taagccgact aacgagcacg ggggcattac taaagcaaac    18480
actcaggtgg agaaaagta ctacagaaca ggggacaacg gtaacccgga aacagtgttt    18540
tatactgaag aggctgacgt gctaacgccc gacacccacc ttgttcacgc ggtaccggcc    18600
gcggatcggc aaaggtggaa ggggctatct cagcacgcag ctcccaacag gccgaacttt    18660
atcggctttc gggactgctt tgtaggcttg atgtattata acagcggggg caacctgggc    18720
gtcttagcgg gtcaatcctc tcagctgaat gccgtggtag acctgcaaga ccgcaacact    18780
gagctttcct atcagatgct tcttgcaaac acgacggaca gatcccgcta ttttagcatg    18840
tggaaccaag ccatggactc gtacgacccg gaggtcaggg tgatagataa cgtgggcgta    18900
gaggacgaga tgcctaatta ctgcttccg ttgtcggggg ttcagattgg aaaccgtagc    18960
```

```
cacgaggttc aaagaaacca acaacagtgg caaaatgtag ctaatagtga caacaattac    19020
ataggcaagg ggaacctacc ggccatggag ataaatctag cggccaatct ctggcgttcc    19080
tttttgtaca gtaatgtggc gttgtacttg ccagacaacc ttaaattcac ccctcacaac    19140
attcaactcc cgcctaacac gaacacctac gagtacatga acgggcgaat ccccgttagc    19200
ggccttattg atacgtacgt aaatataggc acgcggtggt cgcccgatgt gatggacaac    19260
gtgaatccct taaccacca ccgcaactcg ggcctgcgtt accgctccca gctgctgggc    19320
aacggccgct tctgcgactt tcacattcag gtgccacaaa agttttttgc tattcgaaac    19380
ctgcttctcc tgcccggcac gtacacttac gagtggtcct ttagaaagga cgtaaacatg    19440
atccttcaga gcactctggg caatgatctg cgggtcgatg gggccactgt taatattacc    19500
agcgtcaacc tctacgccag cttctttccc atgtcacata acaccgcttc cactttggaa    19560
gctatgctcc gcaacgacac taatgaccag tcttttaatg actatctctc ggcggctaac    19620
atgttgtatc ccattccgcc caatgccacc caactgccca tcccctcacg caactgggca    19680
gcgttccgtg gctggagtct cacccggcta aaacagaggg agacaccggc gctgggtcc    19740
ccgttcgatc cctatttcac ctattcgggc accatcccgt acctggacgg cacttttac    19800
ctcagccaca cctttcgcaa ggtggccatc cagtttgact cttctgtgac ctggcccggc    19860
aatgacaggc ttttaacccc taacgagttc gaaataaaaa taagtgtgga cggtgaaggc    19920
tacaacgtgg ctcagagcaa tatgactaag gactggttcc tggtgcagat gctagcgaat    19980
tacaacatag gctaccaggg atatcacctg ccccccggact acaaggacag gacatttcc    20040
ttcctgcata acttcatacc catgtgccga caggttccca acccagcaac cgagggctac    20100
tttggactag gcatagtgaa ccatagaaca actccggctt attggtttcg attctgccgc    20160
gctccgcgcg agggccaccc ctaccccaa ctggccttac cccctcattg ggacccacgc    20220
catgccctcc gtgacccaga gagaaagttt ctctgcgacc gcaccctctg gcgaatcccc    20280
ttctcctcga acttcatgtc catggggtcc ctcacagatc tcggacagaa cctactgtat    20340
gccaatgccg cgcatgccct agacatgact tttgagatgg atcccatcaa tgagcccact    20400
ctgctgtacg ttctgtttga ggtgtttgac gtggcccgcg ttcaccagcc ccacagaggc    20460
gtgatcgaag tggtgtactt gagaacgcca ttctcagccg gcaacgctac cacataagtg    20520
ccggcttccc tctcaggccc cgcgatgggt tctcgggaag aggagctgag attcatcctt    20580
cacgatctcg gtgtggggcc atacttcctc ggcactttcg ataaacactt tccggggttc    20640
atctccaaag accgaatgag ctgtgccata gtcaacactg ccggacgcga aaccggggc    20700
gtgcattggc tggccatggc ttggcaccca gcctcgcaga ccttttacat gtttgaccct    20760
ttcggttct cggatcaaaa gctaaagcaa atttacaact ttgagtatca gggcctccta    20820
aagcgcagcg ccctgacttc cactgctgac cgctgcctga cccttattca agcactcaa    20880
tctgtccagg gacccaacag cgccgcctgc ggtctgttct gctgcatgtt cctccacgcc    20940
tttgtccgct ggccgcttag ggccatggac aacaatccca ccatgaacct catccacgga    21000
gttcccaaca acatgttgga gagccccagc tcccaaaatg tgttttgag aaaccagcaa    21060
aatctgtacc gtttcctaag acgccactcc ccccattttg ttaagcatgc ggctcaaatt    21120
gaggctgaca ccgcctttga taaatgttta acaaattaga ccgtgagcca tgattgcaga    21180
agcatgtcat ttttttttta ttgtttaaaa taaaaacaac ataacatc tgccgcctgt    21240
cctcccgtga tttcttctgc tttatttgca aatgggggc accttaaaac aaagagtcat    21300
```

```
ctgcatcgta ctgatcgatg ggcagaataa cattctgatg ctggtactgc gggtcccagc    21360
ggaattcggg aatggtaatg gggggctct gtttaaccag cgcggaccac atctgcttaa     21420
ccagctgcaa ggctgaaatc atatctggag ccgaaatctt gaaatcgcag tttcgctggg    21480
cattagcccg cgtctgccgg tacacagggt tacagcactg aaatactaac accgatgggt    21540
gttctacgct ggccaggagt ttgggatctt ctacgaggct cttatctacc gcagagcccg    21600
cgttgatatt aaagggcgtt atcttgcata cctgacggcc taggagggc aattgggagt     21660 gaccccagtt acaatcacac tttaaaggca taagcagatg agttccggca ctttgcatcc    21720
tggggtaaca ggctttctga aaggtcatga tctgccagaa agcctgcaaa gccttgggcc    21780
cctcgctgaa aaacatacca caagactttg aggtaaagct gccggccggc aaagcggcgt    21840
caaagtgaca gcaagccgcg tcttcattct ttagctgcac tacgttcata ttccaccggt    21900
tggtggtgat ctttgtctta tgcggggtct cttttaaagc ccgctgccca ttttcgctgt    21960
tcacatccat ctctatcact tggtctttgg taagcatagg caggccatgc aggcagtgaa    22020
gggccccgtc tcccccctcg gtacactggt ggcgccagac cacacagccc gtgggctcc    22080 acgaggtcgt ccccaggcct gcgacttta acacaaaatc atacaagaag cggcccataa    22140
tagttagcac ggttttctga gtactgaaag taagaggcag gtacacttta gactcattaa    22200
gccaagcttg tgcaaccttc ctaaaacact cgagcgtgcc agtgtcgggc agcaaggtta    22260 agttttaat atccactttc aaaggcacac acagcccac tgctaattcc atggcccgct      22320
gccaagcaac ttcgtcggct tccagcaagg cccggctggc cgccggcagg cggggagcgg    22380
cggcctcagc ggctggggct gaaggtttga aaatcttggc gcgcttaacg gctgtgacat    22440
cttcggcggg gggctcagcg atcggcgcgc gccgtttgcg gctgactttt ttccggggcg    22500
tctcatctat cactaagggg ttctcgtccc cgctgctgtc agccgaactc gtggctcgcg    22560
ttaagtcacc gctgcgattc attattctct cctagataac gacaacaaat ggcagagaaa    22620
ggcagtgaaa atcagcggcc agagaacgac actgagctag cagcggtttc agaagcccta    22680
ggcgcggccg cttcggcccc ctcacgtaac tccccgactg acacggattc aggggtggaa    22740
atgacgccca ccagcagccc cgagccgccc gccgctcccc caagttcgcc tgccgcagca    22800 cctgccctc agaagaacca ggaggagctc tcttcccccg agcccgcggt agcagcagcg    22860
gagccagaag ccgcttcgcg gcccagacca cccacaccca ccgttcaggt cccgcgggag    22920
ccgagcgagg atcaacctga cggacccgcg acgaggcctt cgtacgtgag cgaggattgc    22980
ctcatccgcc atatctctcg ccaggctaac attgttagag acagcctggc agaccgctgg    23040
gagttagagc ccaccgtgtc ggctctctcc gaggcttacg aaaagctcct cttttgtccc    23100 aagtaccac ccaagaagca agagaatggc acttgcgaac ctgaacctcg cgttaatttt     23160
ttccccacct ttgtagtgcc cgaaacttta gccacgtacc acatcttttt ccaaaaccaa    23220 aaaatcccc tgtcttgtcg cgccaaccgc acccacacag acaccatcat gcacctctac     23280
tcgggggact ccttaccgtg cttccccacg ctgcagctgg tcaacaaaat cttttgaaggc   23340 tgggctcag aggagcggcg cgcagccaac tcgctgaaag atcaagagga taacagcgcg    23400
ttagttgagc tcgaagggga cagtccccga ctggctgtgg ttaagcgcac actgtctttg    23460
acacatttcg cctaccctgc cataacacta ccgcctaagg tgatggcagc tgtcactggc    23520
agcctcattc atgaatcagc agcgaccgcc gaaccggaag ctgaggcgct gccagaagcc    23580
gaggagcccg tggttagtga ccctgaactt gctcgctggt tggggctcaa cttacaacag    23640
gagcccgagg ccacggccca ggctttggaa gaaagacgca agattatgtt ggcagtatgc    23700
```

```
ttagtcacac ttcagctcga gtgcctgcac aagttttttt cttcagagga tgtcatcaaa    23760
aagctgggag agagcctcca ctacgccttt cgccacggct acgtgcgcca agcctgctcc    23820
atttctaacg tggaactaac gaacatcgtc tcatacctgg gtatcttgca cgaaaaccgc    23880
ttgggacaga gtaccctaca cgccacccttt aaagacgaga accgcagaga ctacatcaga   23940
gacacagtct ttctctttct ggtttatact tggcagactg ccatgggcat ttggcagcag    24000
tgcctcgaga ctgagaacgt aaaagaactt gaaaagctct gcaaaaaag caagagggct     24060 ctctggacgg gcttcgacga gctcaccata gctcaagacc tagctgacat agtgttcccc    24120
cccaaattct tgcacacctt gcaagccggc ctgccagacc ttacatccca gagtctcctt    24180
cacaactttc gctccttcat tttcgaacgc tcgggcattc tacccgccat gtgcaatgca    24240
ctgcccaccg acttcatccc tatcagctac cgggagtgcc ctccaacttt ctgggcctac    24300
acctacctct ttaaactggc caattacctc atgtttcact ccgacatcgc ttacgatcgg    24360
agcggccccg gtctcatgga atgctactgt cgctgcaacc tgtgcagtcc tcaccgctgc    24420
ttggcgacca ccccgccct gctcagcgag acccaagtta tcggtacctt cgagattcag     24480
ggccctcctg ctcaagacgg acagccgacc aaaccgcccc tcaggctgac tgcaggtctc    24540
tggacttccg cctacctgcg caaatttgta ccgcaagact tcaacgccca caaaatagcc    24600
ttctacgaag accaatccaa aaagccgaaa gtgaccccca gcgcttgtgt catcactgaa    24660
gaaaaagttt tagcccaatt gcatgaaatt aaaaaagcgc gggaagactt tcctcttaaa    24720
aaggggcacg gagtgtatct ggaccctcag accggcgagg agctgaacgg accccgcaccc   24780 tccgcagcta ggaatgaaac cccgcagcat gtcggcagcc gggccttccg cggctcaggc    24840
ttcggagggc caacagctgc cgccacagac agcggggctg cagccgagca agaggctgt     24900 gaggaaggta gtagcttctc tgaatcccac cgccgccctg aagacatat ccgaggggga    24960 ggaaggcttc cccctgacgg acgaggaaga cggggacacc ctggagagcg atttcagcga    25020
cttcacggac gaagacgtcg aggaggagga tatgatttcg ataccccgcg accaggggca    25080
ctccggcgag ctcgaggagg gcgaaattcc cgcaacggta gcggcgacgg cggtcaagaa    25140
gggccagggc aagaagagta ggtgggacca gcaggtccgc tccacagcgc ctctaaaggg    25200
cgctagaggt aagaggagct acagctcctg gaaaccccct caagcccacta tcctttcatg   25260 cttactgcag agctccggca gcactgcctt cactcgccgc tatctgcttt tcgccatgg    25320 cgtgtccgtt ccctccaggg taattcatta ctataattct tactgcagac ccgaagctga    25380
ccaaaaccgc cactcagagc aaaaagagcc gccggagtgc cagcgcggcg cgccctcgcc    25440
ctcctcctct tcctcccaag cgtgctcggg cgccccgccg ccccaaaggc cagcgccatc    25500
aggccgacga cgcaagcacc gagggccgcg acaagcttcg ggagctgatc tttcccactc    25560
tctatgccat attccaacaa agtcgcgctc agcggtgtca cctcaaagtg aaaaatagat    25620
ccttacgttc actgacgcgc agctgcctct accacaacaa ggaggaacag ctccagcgaa    25680
ccctagcaga ctccgaggcg cttctcagta aatactgctc tgcagctccg acacgattct    25740
cgccgccctc ttataccgag tctcccgcca aggacgaatc cggacccgcc taaactctca    25800
gcatgagcaa agaattccc acaccttatg tttggacctt tcaacctcag atgggagcgg     25860
ccgcaggtgc cagtcaagat tactcgaccc gcatgaattg gttcagcgcg ggacctgata    25920
tgatccacga cgttaacaac attcgtgacg cccaaaaccg catccttatg actcagtcgg    25980
ccattaccgc cactcccagg aatctgattg atcccagaca gtgggccgcc cacctcatca    26040
```

```
aacaacccgt ggtgggcacc acccacgtgg aaatgcctcg caacgaagtc ctagaacaac    26100
atctgacctc acatggcgct caaatcgcgg gcggaggcgc tgcgggcgat tactttaaaa    26160
gccccacttc agctcgaacc cttatcccgc tcaccgcctc ctgcttaaga ccagatggag    26220
tctttcaact aggaggaggc tcgcgttcat ctttcaaccc cctgcaaaca gattttgcct    26280
tccacgccct gccctccaga ccgcgccacg ggggcatagg atccaggcag tttgtagagg    26340
aatttgtgcc cgccgtctac ctcaaccct actcgggacc gccggactct tatccggacc    26400
agtttatacg ccactacaac gtgtacagca actctgtgag cggttatagc tgagattgta    26460
agactctcct atctgtctct gtgctgcttt tccgcttcaa gccccacaag catgaagggg    26520
tttctgctca tcttcagcct gcttgtgcat tgtccctaa ttcatgttgg gaccattagc    26580
ttctatgctg caaggcccgg gtctgagcct aacgcgactt atgtttgtga ctatggaagc    26640
gagtcagatt acaaccccac acggttctg tggttggctc gagagaccga tggctcctgg    26700
atctctgttc ttttccgtca caacggctcc tcaactgcag cccccggggt cgtcgcgcac    26760
tttactgacc acaacagcag cattgtggtg cccagtatt acctcctcaa caactcactc    26820
tctaagctct gctgctcata ccggcacaac gagcgttctc agtttacctg caaacaagct    26880
gacgtcccta cctgtcacga gcccggcaag ccgctcaccc tccgcgtctc ccccgcgctg    26940
ggaactgccc accaagcagt cacttggttt tttcaaaatg tacccatagc tactgtttac    27000
cgaccttggg gcaatgtaac ttggttttgt cctcccttca tgtgtaccctt taatgtcagc    27060 ctgaactccc tacttattta caactttct gacaaaaccg gggggcaata cacagctctc    27120
atgcactccg gacctgcttc cctctttcag ctctttaagc caacgacttg tgtcaccaag    27180
gtggaggacc cgccgtatgc caacgacccg gcctcgcctg tgtggcgccc actgcttttt    27240
gccttcgtcc tctgcaccgg ctgcgcggtg ttgttaaccg ccttcggtcc atcgattcta    27300
tccggtaccc gaaagcttat ctcagcccgc ttttggagtc ccgagcccta taccaccctc    27360
cactaacagt ccccccatgg agccagacgg agttcatgcc gagcagcagt ttatcctcaa    27420
tcagatttcc tgcgccaaca ctgccctcca gcgtcaaagg gaggaactag cttcccttgt    27480
catgttgcat gcctgtaagc gtggcctctt ttgtccagtc aaaacttaca agctcagcct    27540
caacgcctcg gccagcgagc acagcctgca ctttgaaaaa agtccctccc gattcaccct    27600
ggtcaacact cacgccggag cttctgtgcg agtggcccta caccaccagg gagcttccgg    27660
cagcatccgc tgttcctgtt cccacgccga gtgcctcccc gtcctcctca agaccctctg    27720
tgcctttaac ttttagatt agctgaaagc aaatataaaa tggtgtgctt accgtaattc    27780
tgttttgact tgtgtgcttg atttctcccc ctgcgccgta atccagtgcc cctcttcaaa    27840
actctcgtac cctatgcgat tcgcataggc atatttcta aaagctctga agtcaacatc    27900
actctcaaac acttctccgt tgtaggttac tttcatctac agataaagtc atccaccggt    27960
taacatcatg aagagaagtg tgccccagga ctttaatctt gtgtatccgt acaaggctaa    28020
gaggcccaac atcatgccgc ccttttttga ccgcaatggc tttgttgaaa accaagaagc    28080
cacgctagcc atgcttgtgg aaaagccgct cacgttcgac aaggaaggtg cgctgaccct    28140
gggcgtcgga cgcggcatcc gcattaaccc cgcggggctt ctggagacaa acgacctcgc    28200
gtccgctgtc ttcccaccgc tggcctccga tgaggccggc aacgtcacgc tcaacatgtc    28260
tgacgggcta tatactaagg acaacaagct agctgtcaaa gtaggtcccg ggctgtccct    28320
cgactccaat aatgctctcc aggtccacac aggcgacggg ctcacggtaa ccgatgacaa    28380
ggtgtctcta aatacccaag ctccccctctc gaccaccagc gcgggcctct ccctacttct    28440
```

```
gggtcccagc ctccacttag gtgaggagga acgactaaca gtaaacaccg gagcgggcct    28500
ccaaattagc aataacgctc tggccgtaaa agtaggttca ggtatcaccg tagatgctca    28560
aaaccagctc gctgcatccc tgggggacgg tctagaaagc agagataata aaactgtcgt    28620
taaggctggg cccggactta caataactaa tcaagctctt actgttgcta ccgggaacgg    28680
ccttcaggtc aacccggaag ggcaactgca gctaaacatt actgccggtc agggcctcaa    28740 cttttgcaaac aacagcctcg ccgtggagct gggctcgggc ctgcattttc ccctggcca    28800 aaaccaagta agcctttatc ccggagatgg aatagacatc cgagataata gggtgactgt    28860
gcccgctggg ccaggcctga gaatgctcaa ccaccaactt gccgtagctt ccggagacgg    28920
tttagaagtc cacagcgaca ccctccggtt aaagctctcc cacggcctga catttgaaaa    28980
tggcgccgta cgagcaaaac taggaccagg acttggcaca gacgactctg gtcggtccgt    29040
ggttcgcaca ggtcgaggac ttagagttgc aaacggccaa gtccagatct tcagcggaag    29100
aggcaccgcc atcggcactg atagcagcct cactctcaac atccgggcgc ccctacaatt    29160
ttctggaccc gccttgactg ctagtttgca aggcagtggt ccgattactt acaacagcaa    29220
caatggcact ttcggtctct ctataggccc cggaatgtgg gtagaccaaa acagacttca    29280
ggtaaaccca ggcgctggtt tagtcttcca aggaaacaac cttgtcccaa accttgcgga    29340
tccgctggct atttccgaca gcaaaattag tctcagtctc ggtcccggcc tgacccaagc    29400
ttccaacgcc ctgactttaa gtttaggaaa cgggcttgaa ttctccaatc aagccgttgc    29460
tataaaagcg ggccggggct tacgctttga gtcttcctca caagctttag agagcagcct    29520
cacagtcgga aatggcttaa cgcttaccga tactgtgatc cgccccaacc taggggacgg    29580
cctagaggtc agagacaata aaatcattgt taagctgggc gcgaatcttc gttttgaaaa    29640
cggagccgta accgccggca ccgttaaccc ttctgcgccc gaggcaccac caactctcac    29700
tgcagaacca cccctccgag cctccaactc ccatcttcaa ctgtccctat cggagggctt    29760
ggttgtgcat aacaacgccc ttgctctcca actgggagac ggcatggaag taaatcagca    29820
cggacttact ttaagagtag gctcgggttt gcaaatgcgt gacggcattt taacagttac    29880
acccagcggc actcctattg agcccagact gactgcccca ctgactcaga cagagaatgg    29940
aatcgggctc gctctcggcg ccggcttgga attagacgag agcgcgctcc aagtaaaagt    30000
tgggcccggc atgcgcctga accctgtaga aaagtatgta accctgctcc tgggtcctgg    30060
ccttagtttt gggcagccgg ccaacaggac aaaattatgat gtgcgcgttt ctgtggagcc    30120
ccccatggtt ttcggacagc gtggtcagct cacatttta gtgggtcacg gactacacat    30180
tcaaaattcc aaacttcagc tcaatttggg acaaggcctc agaactgacc ccgtcaccaa    30240
ccagctggaa gtgcccctcg gtcaaggttt ggaaattgca gacgaatccc aggttagggt    30300
taaattgggc gatggcctgc agtttgattc acaagctcgc atcactaccg ctcctaacat    30360
ggtcactgaa actctgtgga ccggaacagg cagtaatgct aatgttacat ggcggggcta    30420
cactgccccc ggcagcaaac tcttttttgag tctcactcgg ttcagcactg gtctagtttt    30480
aggaaacatg actattgaca gcaatgcatc ctttgggcaa tacattaacg cgggacacga    30540
acagatcgaa tgctttatat tgttggacaa tcagggtaac ctaaaagaag gatctaactt    30600
gcaaggcact tgggaagtga agaacaaccc ctctgcttcc aaagctgctt ttttgccttc    30660
caccgcccta tacccatccc tcaacgaaag ccgagggagt cttcctggaa aaaatcttgt    30720
gggcatgcaa gccatactgg gaggcggggg cacttgcact gtgatagcca ccctcaatgg    30780
```

-continued

```
cagacgcagc aacaactatc ccgcgggcca gtccataatt ttcgtgtggc aagaattcaa      30840
caccatagcc cgccaacctc tgaaccactc tacacttact ttttcttact ggacttaaat      30900
aagttggaaa taaagagtta aactgaatgt ttaagtgcaa cagacttta ttggttttgg       30960 ctcacaacaa attacaacag catagacaag tcataccggt caaacaacac aggctctcga      31020
aaacgggcta accgctccaa gaatctgtca cgcagacgag caagtcctaa atgttttttc      31080
actctcttcg gggccaagtt cagcatgtat cggatttct gcttacacct ttttagacag       31140
cagtttacac tcatttccgt taaggattaa caactgcggc atatgagaat taagtatata       31200
caactattgc cctttaccca caaacactcc ccccacgggg tgcacctgat gtagctgccc       31260
tcctcaatca tgaaagtgct attaaagtaa attaaatgaa cattattcac atacacgctt      31320
cccacatagg ccaaaaaaac agaggacaac tttgacagct cccgcctgaa ataccaatac      31380
actctatcaa actgcgcacc gtgcacgcac tgctttacca ggccttgaaa gtaaacagcg       31440
gcggaccgac actgcaagct tctaggcttt ggcagtggc agtgaatata tagccactcc        31500
tccccatgca cgtagtagga acgccgcttc ccgggaatca caaatgacaa gcagtagtca      31560
cagaggcaac tagtcaagtg agcgtcctcc tgaggcatga ttaccttcca tggaatgggc      31620
cagtgaatca tagtggcaaa gccagctgca tctggagcgc tgcgaaccett ggctacatgt      31680 ggtgattggc gacgcagatg gagacaggac cttgcattct gaagaccact gcaacagctt      31740
ctgcgtacgc ttgtatttac agtacataaa aaagcacttt tgccacagag cggtcttact      31800
caaccgacag cttttttctt tctgacgctg ccttctgcta ctcaggtagt acaagtccaa      31860
aagagccaaa cggacactca atccgggtt atctcgatgc tgaagccaga gtccaaaagt       31920
aaccacgcta aaagcctgca tccatatttt gtaactgctg taactccatc ccagagccgg      31980
gcaccgcact tggtccacca tagctgcaaa caaacgggac aattaaggaa agtaaaatga      32040
gcgctggggg cggactcttc tcccgttcgt aggaaacagc cacgtatcaa acacccttt       32100 caacactggc tctccagccg ctactcgttg aattaatttg tccctgtgct caaacaaccc      32160
acactggtaa cggtggtcgc taggcaaaca tgtcaaatag cacataatca tttccttcac      32220
tttaagcaaa catcgactag cagacacttc acttaattca gcacagtcat agcaaggaat      32280
gattatacac ttgtcatcta atccactgcc catgtacaca ttgccccagg caaagtggg      32340 cagggacttt aagagctgat tgctcgcccc gacatagttg gtaaaataca gcaaatgcac      32400
cttgttaaca tacacactcc ccacatagta aatataccga gtagacagct tagaaagctc      32460
cctccgaaaa aatgggaaca tggtatcaaa ggcagtgccc gcaacacaca tcttgaacag      32520
atccatcagg atagtagctc gacacagccc ctgcagactt tggtcagctt gcttgctgca      32580
gcagtacact ctccacgtag catctccgct gatgaagtat tcgctatcgc agcgaccaaa      32640
aatacagcaa tcacaaggca gacgcaacag tctttcatcc agactgttca tgagaggctt      32700
tagaggtatg ggaaaaaatc caaagtgctc aaaataagca gcgctgggct cattctgaca      32760
ttcccccaac atgctgagtc gaaccatagc acagtcatac aaactcagct gtcggaattg      32820
atcttccatg attgagtttc tactgagata ttatctcaaa cttaaaactg ttgctcacca      32880
actctatgcg aacttgctca agaagctctt ggtttagggc gacctcttct ggtcgtcgga      32940
agttactgat ggaacaacaa gcgccgccca acttcaaatt tccagccgac ccaatccagt      33000
ggtctctcaa ctcacgcgca caagctacta tgcagtcctc actttcgtca aagtcagcag      33060
cgcctataga aatcaacaca ctgagtccac catcttcagc ttttaaggga taacagctga      33120
tagcaaactg gttctgagac cacggcaaag cacgtaggaa ttgctgttaa gttaatttcc      33180
```

```
aaacaccgct gaagcagctc tatggttgct ggacatatgt cctctgcata gaagctttga    33240
acataactta agacagggcc gggcacatga acacaaaca gagaactata cacaatctgg    33300
gccatgatca ctcacattta aatagcagct gaaaagtggc tttcttcact tgggagcaaa    33360
attagcgaag actgtgccag aatgctcacg tcgaaaggcg gtgggtctcg cagaggcagg    33420
ttcggagctc taattaaaca caggtgggta atccagtcaa cgatgaggac cagctgaaaa    33480
gtggctttct tcacttggga gcaaaattag cgaagactgt gccagaatgc tcacgtcgaa    33540
aggcggtggg tctcgcagag gcaggttcgg agctctaatt aaacacaggt gggtaatcca    33600
gtcaacgatg aggactttta aaaaactgtc taaaactgaa gcagttaagt tagaggcaga    33660
cacagaaaaa actacagtta aactatcagt tgctgaaatt gaaaagcacc caataattat    33720
gcgcgagggc acaggcaata aaagtgttag cccctcggct aacgcgtcag ctaaaaaatc    33780
tttagctaaa gtatctactg gccgcgtggt aaaagtttga atataattta cgacaggagc    33840
tggcaagtga aactccacaa aaaagtaaa tggctgcaca cacgccatta ttttgaaaat    33900
aagaagtact cacaaaatca gctggagctg ccgcaagtga aaaagaccag ctgaagtctt    33960 atttttaaact gtaaaatata aaaaaaaaaa tagggcgtga acaaaaatga gaaaataata    34020
ccggatatga ctattaaggg cgtacactga aactgggtaa tatttgagaa aaagattaag    34080
ataatagctg aacaaatgtt gtgtgcagaa cacggaacaa tggtggcgaa aaaaaaaaac    34140
agtgtaagca catggcgcgc acgtacttcc gtgagaaaaa ttaaaaaaat ttacccagta    34200
taaggtgcgt cattagaccc gccttgtggc gcggttgtag ccctgccctt tgccccgccc    34260
cgcgcgccgc cccgcgcgcc gccccgccg ccctcagccc cgcccagcgc cgccgcctcc    34320
gcgacgcgct ccgcccccaca gttacgtcag cacgccacgc tcgccgtcgt tgcgtcataa    34380
atgacgtggc aaaaatgatt ggcagttgga ccgctgccat cagtgtactg tagattattg    34440
atgatg                                                               34446
```

<210> SEQ ID NO 2
<211> LENGTH: 4
<212> TYPE: PRT
<213> ORGANISM: Bovine adenovirus 600

<400> SEQUENCE: 2

Thr Leu Trp Thr
1

<210> SEQ ID NO 3
<211> LENGTH: 8
<212> TYPE: PRT
<213> ORGANISM: Bovine adenovirus 600

<400> SEQUENCE: 3

Thr Pro Ala Pro Ala Pro Asn Cys
1               5

<210> SEQ ID NO 4
<211> LENGTH: 10
<212> TYPE: PRT
<213> ORGANISM: Bovine adenovirus 600

<400> SEQUENCE: 4

Ser Tyr Thr Phe Ser Tyr Ile Ala Gln Glu
1               5                   10

<210> SEQ ID NO 5
<211> LENGTH: 600
<212> TYPE: PRT
<213> ORGANISM: Human adenovirus 5

<400> SEQUENCE: 5

```
Met Ser Val Ser Ser Cys Ser Cys Pro Ser Ala Pro Thr Ile Phe Met
 1               5                  10                  15

Leu Leu Gln Met Lys Arg Ala Arg Pro Ser Glu Asp Thr Phe Asn Pro
            20                  25                  30

Val Tyr Pro Tyr Asp Thr Glu Thr Gly Pro Pro Thr Val Pro Phe Leu
        35                  40                  45

Thr Pro Pro Phe Val Ser Pro Asn Gly Phe Gln Glu Ser Pro Pro Gly
    50                  55                  60

Val Leu Ser Leu Arg Leu Ser Glu Pro Leu Val Thr Ser Asn Gly Met
65                  70                  75                  80

Leu Ala Leu Lys Met Gly Asn Gly Leu Ser Leu Asp Glu Ala Gly Asn
                85                  90                  95

Leu Thr Ser Gln Asn Val Thr Thr Val Ser Pro Pro Leu Lys Lys Thr
            100                 105                 110

Lys Ser Asn Ile Asn Leu Glu Ile Ser Ala Pro Leu Thr Val Thr Ser
        115                 120                 125

Glu Ala Leu Thr Val Ala Ala Ala Ala Pro Leu Met Val Ala Gly Asn
    130                 135                 140

Thr Leu Thr Met Gln Ser Gln Ala Pro Leu Thr Val His Asp Ser Lys
145                 150                 155                 160

Leu Ser Ile Ala Thr Gln Gly Pro Leu Thr Val Ser Glu Gly Lys Leu
                165                 170                 175

Ala Leu Gln Thr Ser Gly Pro Leu Thr Thr Thr Asp Ser Ser Thr Leu
            180                 185                 190

Thr Ile Thr Ala Ser Pro Pro Leu Thr Thr Ala Thr Gly Ser Leu Gly
        195                 200                 205

Ile Asp Leu Lys Glu Pro Ile Tyr Thr Gln Asn Gly Lys Leu Gly Leu
    210                 215                 220

Lys Tyr Gly Ala Pro Leu His Val Thr Asp Asp Leu Asn Thr Leu Thr
225                 230                 235                 240

Val Ala Thr Gly Pro Gly Val Thr Ile Asn Asn Thr Ser Leu Gln Thr
                245                 250                 255

Lys Val Thr Gly Ala Leu Gly Phe Asp Ser Gln Gly Asn Met Gln Leu
            260                 265                 270

Asn Val Ala Gly Gly Leu Arg Ile Asp Ser Gln Asn Arg Arg Leu Ile
        275                 280                 285

Leu Asp Val Ser Tyr Pro Phe Asp Ala Gln Asn Gln Leu Asn Leu Arg
    290                 295                 300

Leu Gly Gln Gly Pro Leu Phe Ile Asn Ser Ala His Asn Leu Asp Ile
305                 310                 315                 320

Asn Tyr Asn Lys Gly Leu Tyr Leu Phe Thr Ala Ser Asn Asn Ser Lys
                325                 330                 335

Lys Leu Glu Val Asn Leu Ser Thr Ala Lys Gly Leu Met Phe Asp Ala
            340                 345                 350

Thr Ala Ile Ala Ile Asn Ala Gly Asp Gly Leu Glu Phe Gly Ser Pro
        355                 360                 365

Asn Ala Pro Asn Thr Asn Pro Leu Lys Thr Lys Ile Gly His Gly Leu
    370                 375                 380
```

```
Glu Phe Asp Ser Asn Lys Ala Met Val Pro Lys Leu Gly Thr Gly Leu
385                 390                 395                 400

Ser Phe Asp Ser Thr Gly Ala Ile Thr Val Gly Asn Lys Asn Asn Asp
            405                 410                 415

Lys Leu Thr Leu Trp Thr Thr Pro Ala Pro Ser Pro Asn Cys Arg Leu
        420                 425                 430

Asn Ala Glu Lys Asp Ala Lys Leu Thr Leu Val Leu Thr Lys Cys Gly
    435                 440                 445

Ser Gln Ile Leu Ala Thr Val Ser Val Leu Ala Val Lys Gly Ser Leu
    450                 455                 460

Ala Pro Ile Ser Gly Thr Val Gln Ser Ala His Leu Ile Ile Arg Phe
465                 470                 475                 480

Asp Glu Asn Gly Val Leu Leu Asn Asn Ser Phe Leu Asp Pro Glu Tyr
            485                 490                 495

Trp Asn Phe Arg Asn Gly Asp Leu Thr Glu Gly Thr Ala Tyr Thr Asn
            500                 505                 510

Ala Val Gly Phe Met Pro Asn Leu Ser Ala Tyr Pro Lys Ser His Gly
        515                 520                 525

Lys Thr Ala Lys Ser Asn Ile Val Ser Gln Val Tyr Leu Asn Gly Asp
    530                 535                 540

Lys Thr Lys Pro Val Thr Leu Thr Ile Thr Leu Asn Gly Thr Gln Glu
545                 550                 555                 560

Thr Gly Asp Thr Thr Pro Ser Ala Tyr Ser Met Ser Phe Ser Trp Asp
            565                 570                 575

Trp Ser Gly His Asn Tyr Ile Asn Glu Ile Phe Ala Thr Ser Ser Tyr
            580                 585                 590

Thr Phe Ser Tyr Ile Ala Gln Glu
        595                 600

<210> SEQ ID NO 6
<211> LENGTH: 976
<212> TYPE: PRT
<213> ORGANISM: Bovine adenovirus 3

<400> SEQUENCE: 6

Met Lys Arg Ser Val Pro Gln Asp Phe Asn Leu Val Tyr Pro Tyr Lys
1               5                   10                  15

Ala Lys Arg Pro Asn Ile Met Pro Pro Phe Phe Asp Arg Asn Gly Phe
            20                  25                  30

Val Glu Asn Gln Glu Ala Thr Leu Ala Met Leu Val Glu Lys Pro Leu
        35                  40                  45

Thr Phe Asp Lys Glu Gly Ala Leu Thr Leu Gly Val Gly Arg Gly Ile
    50                  55                  60

Arg Ile Asn Pro Ala Gly Leu Leu Glu Thr Asn Asp Leu Ala Ser Ala
65                  70                  75                  80

Val Phe Pro Pro Leu Ala Ser Asp Glu Ala Gly Asn Val Thr Leu Asn
            85                  90                  95

Met Ser Asp Gly Leu Tyr Thr Lys Asp Asn Lys Leu Ala Val Lys Val
            100                 105                 110

Gly Pro Gly Leu Ser Leu Asp Ser Asn Asn Ala Leu Gln Val His Thr
        115                 120                 125

Gly Asp Gly Leu Thr Val Thr Asp Asp Lys Val Ser Leu Asn Thr Gln
    130                 135                 140

Ala Pro Leu Ser Thr Thr Ser Ala Gly Leu Ser Leu Leu Leu Gly Pro
145                 150                 155                 160
```

```
Ser Leu His Leu Gly Glu Glu Arg Leu Thr Val Asn Thr Gly Ala
            165                 170                 175

Gly Leu Gln Ile Ser Asn Asn Ala Leu Ala Val Lys Val Gly Ser Gly
            180                 185                 190

Ile Thr Val Asp Ala Gln Asn Gln Leu Ala Ala Ser Leu Gly Asp Gly
            195                 200                 205

Leu Glu Ser Arg Asp Asn Lys Thr Val Val Lys Ala Gly Pro Gly Leu
    210                 215                 220

Thr Ile Thr Asn Gln Ala Leu Thr Val Ala Thr Gly Asn Gly Leu Gln
225                 230                 235                 240

Val Asn Pro Glu Gly Gln Leu Gln Leu Asn Ile Thr Ala Gly Gln Gly
                245                 250                 255

Leu Asn Phe Ala Asn Asn Ser Leu Ala Val Glu Leu Gly Ser Gly Leu
            260                 265                 270

His Phe Pro Pro Gly Gln Asn Gln Val Ser Leu Tyr Pro Gly Asp Gly
            275                 280                 285

Ile Asp Ile Arg Asp Asn Arg Val Thr Val Pro Ala Gly Pro Gly Leu
    290                 295                 300

Arg Met Leu Asn His Gln Leu Ala Val Ala Ser Gly Asp Gly Leu Glu
305                 310                 315                 320

Val His Ser Asp Thr Leu Arg Leu Lys Leu Ser His Gly Leu Thr Phe
                325                 330                 335

Glu Asn Gly Ala Val Arg Ala Lys Leu Gly Pro Gly Leu Gly Thr Asp
            340                 345                 350

Asp Ser Gly Arg Ser Val Val Arg Thr Gly Arg Gly Leu Arg Val Ala
            355                 360                 365

Asn Gly Gln Val Gln Ile Phe Ser Gly Arg Gly Thr Ala Ile Gly Thr
            370                 375                 380

Asp Ser Ser Leu Thr Leu Asn Ile Arg Ala Pro Leu Gln Phe Ser Gly
385                 390                 395                 400

Pro Ala Leu Thr Ala Ser Leu Gln Gly Ser Gly Pro Ile Thr Tyr Asn
                405                 410                 415

Ser Asn Asn Gly Thr Phe Gly Leu Ser Ile Gly Pro Gly Met Trp Val
            420                 425                 430

Asp Gln Asn Arg Leu Gln Val Asn Pro Gly Ala Gly Leu Val Phe Gln
            435                 440                 445

Gly Asn Asn Leu Val Pro Asn Leu Ala Asp Pro Leu Ala Ile Ser Asp
450                 455                 460

Ser Lys Ile Ser Leu Ser Leu Gly Pro Gly Leu Thr Gln Ala Ser Asn
465                 470                 475                 480

Ala Leu Thr Leu Ser Leu Gly Asn Gly Leu Glu Phe Ser Asn Gln Ala
                485                 490                 495

Val Ala Ile Lys Ala Gly Arg Gly Leu Arg Phe Glu Ser Ser Ser Gln
                500                 505                 510

Ala Leu Glu Ser Ser Leu Thr Val Gly Asn Gly Leu Thr Leu Thr Asp
            515                 520                 525

Thr Val Ile Arg Pro Asn Leu Gly Asp Gly Leu Glu Val Arg Asp Asn
    530                 535                 540

Lys Ile Ile Val Lys Leu Gly Ala Asn Leu Arg Phe Glu Asn Gly Ala
545                 550                 555                 560

Val Thr Ala Gly Thr Val Asn Pro Ser Ala Pro Glu Ala Pro Pro Thr
                565                 570                 575
```

```
Leu Thr Ala Glu Pro Pro Leu Arg Ala Ser Asn Ser His Leu Gln Leu
            580                 585                 590

Ser Leu Ser Glu Gly Leu Val His Asn Asn Ala Leu Ala Leu Gln
        595                 600                 605

Leu Gly Asp Gly Met Glu Val Asn Gln His Gly Leu Thr Leu Arg Val
610                 615                 620

Gly Ser Gly Leu Gln Met Arg Asp Gly Ile Leu Thr Val Thr Pro Ser
625                 630                 635                 640

Gly Thr Pro Ile Glu Pro Arg Leu Thr Ala Pro Leu Thr Gln Thr Glu
                645                 650                 655

Asn Gly Ile Gly Leu Ala Leu Gly Ala Gly Leu Glu Leu Asp Glu Ser
            660                 665                 670

Ala Leu Gln Val Lys Val Gly Pro Gly Met Arg Leu Asn Pro Val Glu
        675                 680                 685

Lys Tyr Val Thr Leu Leu Gly Pro Gly Leu Ser Phe Gly Gln Pro
690                 695                 700

Ala Asn Arg Thr Asn Tyr Asp Val Arg Val Ser Val Glu Pro Pro Met
705                 710                 715                 720

Val Phe Gly Gln Arg Gly Gln Leu Thr Phe Leu Val Gly His Gly Leu
                725                 730                 735

His Ile Gln Asn Ser Lys Leu Gln Leu Asn Leu Gly Gln Gly Leu Arg
            740                 745                 750

Thr Asp Pro Val Thr Asn Gln Leu Glu Val Pro Leu Gly Gln Gly Leu
        755                 760                 765

Glu Ile Ala Asp Glu Ser Gln Val Arg Val Lys Leu Gly Asp Gly Leu
770                 775                 780

Gln Phe Asp Ser Gln Ala Arg Ile Thr Thr Ala Pro Asn Met Val Thr
785                 790                 795                 800

Glu Thr Leu Trp Thr Gly Thr Gly Ser Asn Ala Asn Val Thr Trp Arg
                805                 810                 815

Gly Tyr Thr Ala Pro Gly Ser Lys Leu Phe Leu Ser Leu Thr Arg Phe
            820                 825                 830

Ser Thr Gly Leu Val Leu Gly Asn Met Thr Ile Asp Ser Asn Ala Ser
        835                 840                 845

Phe Gly Gln Tyr Ile Asn Ala Gly His Glu Gln Ile Glu Cys Phe Ile
850                 855                 860

Leu Leu Asp Asn Gln Gly Asn Leu Lys Glu Gly Ser Asn Leu Gln Gly
865                 870                 875                 880

Thr Trp Glu Val Lys Asn Asn Pro Ser Ala Ser Lys Ala Ala Phe Leu
                885                 890                 895

Pro Ser Thr Ala Leu Tyr Pro Ile Leu Asn Glu Ser Arg Gly Ser Leu
            900                 905                 910

Pro Gly Lys Asn Leu Val Gly Met Gln Ala Ile Leu Gly Gly Gly
        915                 920                 925

Thr Cys Thr Val Ile Ala Thr Leu Asn Gly Arg Arg Ser Asn Asn Tyr
930                 935                 940

Pro Ala Gly Gln Ser Ile Ile Phe Val Trp Gln Phe Asn Thr Ile
945                 950                 955                 960

Ala Arg Gln Pro Leu Asn His Ser Thr Leu Thr Phe Ser Tyr Trp Thr
                965                 970                 975

<210> SEQ ID NO 7
<211> LENGTH: 543
<212> TYPE: PRT
```

<213> ORGANISM: Ovine adenovirus 287

<400> SEQUENCE: 7

```
Met Lys Arg Ala Arg Trp Asp Pro Val Tyr Pro Phe Ser Glu Glu Arg
 1               5                  10                  15

Leu Val Pro Leu Pro Pro Phe Ile Glu Ala Gly Lys Gly Leu Lys Ser
            20                  25                  30

Glu Gly Leu Ile Leu Ser Leu Asn Phe Thr Asp Pro Ile Thr Ile Asn
        35                  40                  45

Gln Thr Gly Phe Leu Thr Val Lys Leu Gly Asp Gly Ile Phe Ile Asn
    50                  55                  60

Gly Glu Gly Gly Leu Ser Ser Thr Ala Pro Lys Val Lys Val Pro Leu
65                  70                  75                  80

Thr Val Ser Asp Glu Thr Leu Gln Leu Leu Ser Asn Ser Leu Thr
                85                  90                  95

Thr Glu Ser Asp Ser Leu Ala Leu Lys Gln Pro Gln Leu Pro Leu Lys
                100                 105                 110

Ile Asn Asp Glu Gly Ser Leu Val Leu Asn Leu Asn Thr Pro Leu Asn
            115                 120                 125

Leu Gln Asn Glu Arg Leu Ser Leu Asn Val Ser Asn Pro Leu Lys Ile
    130                 135                 140

Ala Ala Asp Ser Leu Thr Ile Asn Leu Lys Glu Pro Leu Gly Leu Gln
145                 150                 155                 160

Asn Glu Ser Leu Gly Leu Asn Leu Ser Asp Pro Met Asn Ile Thr Pro
                165                 170                 175

Glu Gly Asn Leu Gly Ile Lys Leu Lys Asn Pro Met Lys Val Glu Glu
            180                 185                 190

Ser Ser Leu Ala Leu Asn Tyr Lys Asn Pro Leu Ala Ile Ser Asn Asp
        195                 200                 205

Ala Leu Ser Ile Asn Ile Ala Asn Pro Leu Thr Val Asn Thr Ser Gly
    210                 215                 220

Ser Leu Gly Ile Ser Tyr Ser Thr Pro Leu Arg Ile Ser Asn Asn Ala
225                 230                 235                 240

Leu Ser Leu Phe Ile Gly Lys Pro Leu Gly Leu Gly Thr Asp Gly Ser
                245                 250                 255

Leu Thr Val Asn Leu Thr Arg Pro Leu Val Cys Arg Gln Asn Thr Leu
            260                 265                 270

Ala Ile Asn Tyr Ser Ala Pro Leu Val Ser Leu Gln Asp Asn Leu Thr
        275                 280                 285

Leu Ser Tyr Ala Gln Pro Leu Thr Val Ser Asp Asn Ser Leu Arg Leu
    290                 295                 300

Ser Leu Asn Ser Pro Leu Asn Thr Asn Ser Asp Gly Lys Leu Ser Val
305                 310                 315                 320

Asn Tyr Ser Asn Pro Leu Val Val Thr Asp Ser Asn Leu Thr Leu Ser
                325                 330                 335

Val Lys Lys Pro Val Met Ile Asn Asn Thr Gly Asn Val Asp Leu Ser
            340                 345                 350

Phe Thr Ala Pro Ile Lys Leu Asn Asp Ala Glu Gln Leu Thr Leu Glu
        355                 360                 365

Thr Thr Glu Pro Leu Glu Val Ala Asp Asn Ala Leu Lys Leu Lys Leu
    370                 375                 380

Gly Lys Gly Leu Thr Val Ser Asn Asn Ala Leu Thr Leu Asn Leu Gly
385                 390                 395                 400
```

```
Asn Gly Leu Thr Phe Gln Gln Gly Leu Leu Gln Ile Lys Thr Asn Ser
            405                 410                 415

Ser Leu Gly Phe Asn Ala Ser Gly Glu Leu Ser Thr Ala Thr Lys Gln
        420                 425                 430

Gly Thr Ile Thr Val Asn Phe Leu Ser Thr Thr Pro Ile Ala Phe Gly
            435                 440                 445

Trp Gln Ile Ile Pro Thr Thr Val Ala Phe Ile Tyr Ile Leu Ser Gly
    450                 455                 460

Thr Gln Phe Thr Pro Gln Ser Pro Val Thr Ser Leu Gly Phe Gln Pro
465                 470                 475                 480

Pro Gln Asp Phe Leu Asp Phe Val Leu Ser Pro Phe Val Thr Ser
                485                 490                 495

Val Thr Gln Ile Val Gly Asn Asp Val Lys Val Ile Gly Leu Thr Ile
            500                 505                 510

Ser Lys Asn Gln Ser Thr Ile Thr Met Lys Phe Thr Ser Pro Leu Ala
        515                 520                 525

Glu Asn Val Pro Val Ser Met Phe Thr Ala His Gln Phe Arg Gln
530                 535                 540
```

<210> SEQ ID NO 8
<211> LENGTH: 448
<212> TYPE: PRT
<213> ORGANISM: Porcine adenovirus 3

<400> SEQUENCE: 8

```
Met Gly Pro Lys Lys Gln Lys Arg Glu Leu Pro Glu Asp Phe Asp Pro
1               5                   10                  15

Val Tyr Pro Tyr Asp Val Pro Gln Leu Gln Ile Asn Pro Pro Phe Val
            20                  25                  30

Ser Gly Asp Gly Phe Asn Gln Ser Val Asp Gly Val Leu Ser Leu His
        35                  40                  45

Ile Ala Pro Pro Leu Val Phe Asp Asn Thr Arg Ala Leu Thr Leu Ala
    50                  55                  60

Phe Gly Gly Leu Gln Leu Ser Gly Lys Gln Leu Val Val Ala Thr
65                  70                  75                  80

Glu Gly Ser Gly Leu Thr Thr Asn Pro Asp Gly Lys Leu Val Leu Lys
                85                  90                  95

Val Lys Ser Pro Ile Thr Leu Thr Ala Glu Gly Ile Ser Leu Ser Leu
            100                 105                 110

Gly Pro Gly Leu Ser Asn Ser Glu Thr Gly Leu Ser Leu Gln Val Thr
        115                 120                 125

Ala Pro Leu Gln Phe Gln Gly Asn Ala Leu Thr Leu Pro Leu Ala Ala
    130                 135                 140

Gly Leu Gln Asn Thr Asp Gly Met Gly Val Lys Leu Gly Ser Gly
145                 150                 155                 160

Leu Thr Thr Asp Asn Ser Gln Ala Val Thr Val Gln Val Gly Asn Gly
                165                 170                 175

Leu Gln Leu Asn Gly Glu Gly Gln Leu Thr Val Pro Ala Thr Ala Pro
            180                 185                 190

Leu Val Ser Gly Ser Ala Gly Ile Ser Phe Asn Tyr Ser Ser Asn Asp
        195                 200                 205

Phe Val Leu Asp Asn Asp Ser Leu Ser Leu Arg Pro Lys Ala Ile Ser
    210                 215                 220

Val Thr Pro Pro Leu Gln Ser Thr Glu Asp Thr Ile Ser Leu Asn Tyr
225                 230                 235                 240
```

-continued

```
Ser Asn Asp Phe Ser Val Asp Asn Gly Ala Leu Thr Leu Ala Pro Thr
            245                 250                 255

Phe Lys Pro Tyr Thr Leu Trp Thr Gly Ala Ser Pro Thr Ala Asn Val
        260                 265                 270

Ile Leu Thr Asn Thr Thr Thr Pro Asn Gly Thr Phe Leu Cys Leu
    275                 280                 285

Thr Arg Val Gly Gly Leu Val Leu Gly Ser Phe Ala Leu Lys Ser Ser
290                 295                 300

Ile Asp Leu Thr Ser Met Thr Lys Lys Val Asn Phe Ile Phe Asp Gly
305                 310                 315                 320

Ala Gly Arg Leu Gln Ser Asp Ser Thr Tyr Lys Gly Arg Phe Gly Phe
                325                 330                 335

Arg Ser Asn Asp Ser Val Ile Glu Pro Thr Ala Ala Gly Leu Ser Pro
                340                 345                 350

Ala Trp Leu Met Pro Ser Thr Phe Ile Tyr Pro Arg Asn Thr Ser Gly
            355                 360                 365

Ser Ser Leu Thr Ser Phe Val Tyr Ile Asn Gln Thr Tyr Val His Val
    370                 375                 380

Asp Ile Lys Val Asn Thr Leu Ser Thr Asn Gly Tyr Ser Leu Glu Phe
385                 390                 395                 400

Asn Phe Gln Asn Met Ser Phe Ser Ala Pro Phe Ser Thr Ser Tyr Gly
                405                 410                 415

Thr Phe Cys Tyr Val Pro Arg Arg Thr Thr His Arg Pro Arg His Gly
            420                 425                 430

Pro Phe Ser Leu Arg Glu Arg His Leu Phe Gln Leu Leu Gln Gln
            435                 440                 445

<210> SEQ ID NO 9
<211> LENGTH: 542
<212> TYPE: PRT
<213> ORGANISM: Canine adenovirus 2

<400> SEQUENCE: 9

Met Lys Arg Thr Arg Arg Ala Leu Pro Ala Asn Tyr Asp Pro Val Tyr
1               5                   10                  15

Pro Tyr Asp Ala Pro Gly Ser Ser Thr Gln Pro Pro Phe Phe Asn Asn
            20                  25                  30

Lys Gln Gly Leu Thr Glu Ser Pro Pro Gly Thr Leu Ala Val Asn Val
        35                  40                  45

Ser Pro Pro Leu Thr Phe Ser Thr Leu Gly Ala Ile Lys Leu Ser Thr
    50                  55                  60

Gly Pro Gly Leu Thr Leu Asn Glu Gly Lys Leu Gln Ala Ser Leu Gly
65                  70                  75                  80

Pro Gly Leu Ile Thr Asn Thr Glu Gly Gln Ile Thr Val Glu Asn Val
                85                  90                  95

Asn Lys Val Leu Ser Phe Thr Ser Pro Leu His Lys Asn Glu Asn Thr
            100                 105                 110

Val Ser Leu Ala Leu Gly Asp Gly Leu Glu Asp Glu Asn Gly Thr Leu
        115                 120                 125

Lys Val Thr Phe Pro Thr Pro Pro Pro Leu Gln Phe Ser Pro Pro
    130                 135                 140

Leu Thr Lys Thr Gly Gly Thr Val Ser Leu Pro Leu Gln Asp Ser Met
145                 150                 155                 160

Gln Val Thr Asn Gly Lys Leu Gly Val Lys Pro Thr Thr Tyr Ala Pro
```

-continued

```
                165                 170                 175
Pro Leu Lys Lys Thr Asp Gln Val Ser Leu Gln Val Gly Ser Gly
            180                 185                 190

Leu Thr Val Ile Asn Glu Gln Leu Gln Ala Val Gln Pro Pro Ala Thr
            195                 200                 205

Thr Tyr Asn Glu Pro Leu Ser Lys Thr Asp Asn Ser Val Ser Leu Gln
            210                 215                 220

Val Gly Ala Gly Leu Ala Val Gln Ser Gly Ala Leu Val Ala Thr Pro
225                 230                 235                 240

Pro Pro Pro Leu Thr Phe Thr Ser Pro Leu Glu Lys Asn Glu Asn Thr
                245                 250                 255

Val Ser Leu Gln Val Gly Ala Gly Leu Ser Val Gln Asn Asn Ala Leu
                260                 265                 270

Val Ala Thr Pro Pro Pro Leu Thr Phe Ala Tyr Pro Leu Val Lys
                275                 280                 285

Asn Asp Asn His Val Ala Leu Ser Ala Gly Ser Gly Leu Arg Ile Ser
            290                 295                 300

Gly Gly Ser Leu Thr Val Ala Thr Gly Pro Gly Leu Ser His Gln Asn
305                 310                 315                 320

Gly Thr Ile Gly Ala Val Val Gly Ala Gly Leu Lys Phe Glu Asn Asn
                325                 330                 335

Ala Ile Leu Ala Lys Leu Gly Asn Gly Leu Thr Ile Arg Asp Gly Ala
                340                 345                 350

Ile Glu Ala Thr Gln Pro Pro Ala Ala Pro Ile Thr Leu Trp Thr Gly
            355                 360                 365

Pro Gly Pro Ser Ile Asn Gly Phe Ile Asn Asp Thr Pro Val Ile Arg
            370                 375                 380

Cys Phe Ile Cys Leu Thr Arg Asp Ser Asn Leu Val Thr Val Asn Ala
385                 390                 395                 400

Ser Phe Val Gly Glu Gly Gly Tyr Arg Ile Val Ser Pro Thr Gln Ser
                405                 410                 415

Gln Phe Ser Leu Ile Met Glu Phe Asp Gln Phe Gly Gln Leu Met Ser
                420                 425                 430

Thr Gly Asn Ile Asn Ser Thr Thr Thr Trp Gly Glu Lys Pro Trp Gly
            435                 440                 445

Asn Asn Thr Val Gln Pro Arg Pro Ser His Thr Trp Lys Leu Cys Met
450                 455                 460

Pro Asn Arg Glu Val Tyr Ser Thr Pro Ala Ala Thr Ile Ser Arg Cys
465                 470                 475                 480

Gly Leu Asp Ser Ile Ala Val Asp Gly Ala Pro Ser Arg Ser Ile Asp
                485                 490                 495

Cys Met Leu Ile Ile Asn Lys Pro Lys Gly Val Ala Thr Tyr Thr Leu
                500                 505                 510

Thr Phe Arg Phe Leu Asn Phe Asn Arg Leu Ser Gly Gly Thr Leu Phe
            515                 520                 525

Lys Thr Asp Val Leu Thr Phe Thr Tyr Val Gly Glu Asn Gln
530                 535                 540
```